US007851591B1

(12) United States Patent
Nadler et al.

(10) Patent No.: US 7,851,591 B1
(45) Date of Patent: Dec. 14, 2010

(54) CANCER IMMUNOTHERAPY AND DIAGNOSIS USING UNIVERSAL TUMOR ASSOCIATED ANTIGENS, INCLUDING HTERT

(75) Inventors: Lee M. Nadler, Newton, MA (US); William C. Hahn, Waltham, MA (US); Joachim L. Schultze, Brookline, MA (US); Robert H. Vonderheide, Brookline, MA (US)

(73) Assignee: Dana Farber Cancer Institute, Inc., Boston, MA (US)

( * ) Notice: Subject to any disclaimer, the term of this patent is extended or adjusted under 35 U.S.C. 154(b) by 113 days.

(21) Appl. No.: 09/830,400

(22) PCT Filed: Oct. 29, 1999

(86) PCT No.: PCT/US99/25438

§ 371 (c)(1),
(2), (4) Date: Jul. 20, 2001

(87) PCT Pub. No.: WO00/25813

PCT Pub. Date: May 11, 2000

Related U.S. Application Data

(60) Provisional application No. 60/106,106, filed on Oct. 29, 1998.

(51) Int. Cl.
| C07K 5/00 | (2006.01) |
| C07K 7/00 | (2006.01) |
| C07K 16/00 | (2006.01) |
| C07K 17/00 | (2006.01) |
| A61K 38/04 | (2006.01) |

(52) U.S. Cl. .................................................. 530/328
(58) Field of Classification Search ........................ None
See application file for complete search history.

(56) References Cited

U.S. PATENT DOCUMENTS

| 5,399,346 A | 3/1995 | Anderson et al. ........ 424/93.21 |
| 5,679,647 A | 10/1997 | Carson et al. |
| 5,747,317 A | 5/1998 | Cao |
| 5,770,422 A | 6/1998 | Collins |
| 6,475,789 B1 * | 11/2002 | Cech et al. .................. 435/366 |

FOREIGN PATENT DOCUMENTS

| WO | WO 98/04582 | 2/1998 |
| WO | WO 98/14593 | 4/1998 |
| WO | WO 98/37181 | 8/1998 |
| WO | WO 99/50392 | 10/1999 |
| WO | WO 00/02581 | 1/2000 |

OTHER PUBLICATIONS

Altuvia et al., 1997, Human Immunology, vol. 58: 1-11.*
Koopmann et al., 1997, Curr. Opin. Immunol. vol. 9: 80-88.*
Bohm et al., "Identification of HLA-A2-Restricted Epitopes of the Tumor-Associated Antigen MUC2 Recognized by Human Cytotoxic T Cells," *International J. of Cancer* 75:688-693 (1998).
Brunette et al., "Immunotherapy (Cancer): Tumor Antigen Specific Immunotherapy of Cancer: Peptide and Gene Based Modification of Dendritic Cells as Antigen Presenting Cells," *Cancer Biotechnology Weekly* p. 16 (1996).
Celis et al., "Identification of Potential CTL Epitopes of Tumor-Associated Antigen MAGE-1 for Five Common HLA-A Alleles," *Molecular Immunology* 31:1423-1430 (1994).
Herlyn et al., "Epitope- and Antigen-Specific Cancer Vaccines," *International Review of Immunology* 7:245-257 (1991).
Brossart, et al. (1998). "Her-2/neu-derived peptides are tumor-associated antigens expressed by human renal cell and colon carcinoma lines and are recognized by in vitro induced specific cytotoxic T lymphocytes." *Cancer Research*. 58(4):732-736.
Jensen, et al. (1998). "A europium fluoroimmunoassay for measuring peptide binding to MHC class I molecules." *Journal of Immunological Methods*. 215(1-2):71-80.
Kawashima, et al. (1998). "The multi-epitope approach for Immunotherapy for cancer: identification of several CTL epitopes from various tumor-associated antigens expressed on solid epithelial tumors." *Human Immunology*. 59(1):1-14.
Kim, at al. (1994). "Specific association of human telomerase activity with immortal cells and cancer." *Science*. 266:2011-2015.
Schultze, et al. (1997). "CD40-activated human B cells: an alternative source of highly efficient antigen presenting cells to generate autologous antigen-specific T cells for adoptive immunotherapy." *Journal of Clinical Investigation*. 100(11):2757-2765.
Schultze, et al. (1997). "Vaccination as immunotherapy for B cell lymphoma." *Hematological Oncology*. 15(3):129-139.
Vonderheide, et al. (1999). "Generation of telomerase-specific HLA-A3-restricted cytotoxic T lymphocytes from patient blood: implications for widely applicable anti-cancer immunotherapy." *Forty-first annual meeting of the American Society of Hematology;*, New Orleans. 94(10):677a.
Schultze et al., "Autologous adoptive T cell transfer for a patient with plasma cell leukemia: results of a pilot phase I trial", *Therapy of Chronic Lymphocytic Leukemia and Multiple Myeloma*, Abstract #446, p. 109a (1998).
Vonderheide et al., "The telomerase catalytic subunit is a widely expressed tumor-associated antigen recognized by Cytotoxic T lymphocytes", *Immunity*, 10:673-679 (1999).
Alexander et al., "Derivation of HLA-A11/K$^b$ transgenic Mice" *J. Immunol.*, 159:4753-4761 (1997).
Altman et al., "Phenotypic Analysis of Antigen-Specific T Lymphocytes", *Science*, 274:94-96 (1996).

(Continued)

*Primary Examiner*—Amy E Juedes
(74) *Attorney, Agent, or Firm*—Mintz Levin Cohn Ferris Glovsky and Popeo, P.C.; Ivor R. Elrifi; Cynthia A. Kozakiewicz

(57) ABSTRACT

The invention provides methods for conducting cancer immunotherapy and diagnosis using universal tumor associated antigens, such as the telomerase catalytic subunit (hTERT), and methods for identifying and characterizing universal tumor associated antigens.

1 Claim, 12 Drawing Sheets

OTHER PUBLICATIONS

Altschul et al., "Gapped BLAST and PSI-BLAST: a new generation of protein database search programs", *Nuc. Acids Res.*, 25(17):3389-3402 (1997).

Anderson et al., "Intracellular Transport of Class I MHC Molecules in Antigen Processing Mutant Cell Lines", *J. Immunol.*, 151(7):3407-3419 (1993).

Anderson, W.F., "Prospects for Human Gene Therapy", *Science*, 226:401-409 (1984).

Aruga et al., "Tumor-specific granulocyte/macrophage colony-stimulating factor and interferon γ secretion is associated with in vivo therapeutic efficacy of activated tumor-draining lymph node cells", *Cancer Immunol. Immunother.*, 41:317-324 (1995).

Ashley et al., "Bone marrow-generated dendritic cells pulsed with tumor extracts or tumor RNA induce antitumor immunity against central nervous system tumors",*J. Exp. Med.*, 186(7):1177-1182 (1997).

Blomer et al., "Highly Efficient and Sustained Gene Transfer in Adult Neurons with a Lentivirus Vector", *J. Virol.*, 71(9):6641-6649 (1997).

Boczkowski et al., "Dendritic Cells Pulsed with RNA are Potent Antigen-presenting Cells in Vitro and in Vivo", *J. Exp. Med.*, 184:465-472 (1996).

Bohlen et al., "Differentiation of cytotoxicity using target cells labeled with europium and samarium by electroporation", *J. Immunol. Meth.*, 173:55-62 (1994).

Boon et al., "Tumor anatigens recognized by T lymphocites",*Ann. Rev. Immunol.*, 12:337-365 (1994).

Brigham et al., "Rapid Communication: in vivo Transfection of Murine Lungs with a Functioning Prokaryotic Gene Using a Liposome Vehicle", *Am. J. Med. Sci.*, 298(4):278-281 (1989).

Broccoli et al., "Telomerase activity in normal and malignant hematopoietic cells",*Proc. Nat'l. Acad. Sci. U.S.A.*, 92:9082-9086 (1995).

Brodie et al., "In vivo migration and function of transferred HIV-1-specific cytotoxic T cells", *Nat. Med.*, 5(1):34-41 (1999).

Brossart et al., "Identification of HLA-A2_Restricted T-Cell Epitopes Derived From the MUCI Tumor Antigen for Broadly Applicable Vaccine Therapies", *Blood*, 93:4309-4317 (1999).

Brusic et al., "MHCPEP, a database of MHC-binding peptides: update 1997", *Nuc. Acids Res.*, 26(1):368-371 (1998).

Brusic et al., "Prediction of MHC class II-binding peptides using an evolutionary algorithm and artificial neural network", *Bioinformatics*, 14(2):121-130 (1998).

Bryan et al., "Evidence for an alternative mechanism for maintaining telomere length in human tumors and tumor-derived cell lines", *Nat. Med.*, 3(11):1271-1274 (1997).

Buchovich et al., "Telomerase Regulation during Entry into the Cell Cycle in Normal Human T Cells", *Mol. Bio. Cell*, 7:1443-1454 (1996).

Busch et al., "MHC Class I/Peptide Stability: Implications for Immunodominance, in Vitro Proliferation, and Diversity of Responding CTL",*J. Immunol.*, 160:4441-4448 (1998).

Callan et al., "Direct Visualization of Antigen-specific CD8+ T Cells during the Primary Immune Response to Epstein-Barr Virus in Vivo", *J. Exp. Med.*, 187:1395-1402 (1998).

Cayouette et al., "Adenovirus-Mediated Gene Transfer of Ciliary Neurotrophic Factor Can Prevent Photoreceptor Degeneration in the Retinal Degeneration (rd) Mouse", *Hum. Gene Ther.*, 8:423-430 (1997).

Cornetta et al., "Gene Transfer into Primates and Prospects for Gene Therapy in Humans",*Nucl. Acid Res. Mol. Biol.*, 36:311-322 (1987).

Cornette et al., "Periodic variation in side-chain polarities of T-cell antigenic peptides correlates with their structure and activity", *Proc. Nat'l. Acad. Sci. U.S.A.*, 92:8368-8372 (1995).

Counter et al., "Stabilization of Short Telomeres and Telomerase Activity Accompany Immortalization of Epstein-Barr Virus-Transformed Human B Lymphocytes",*J. Virol.*, 68:3410-3414 (1994).

Counter et al., "Telomerase activity is restored in human cells by ectopic expression of hTERT (hEST2), the catalityc submit of telomerase", *Oncogene.*, 16:1217-1222 (1998).

De Groot et al., "Prediction of Protein Conformational Freedom From Distance Constraints", *Proteins: Struct. Funct. Genet.*, 29:240-251 (1997).

DeLisi et al., "T-cell antigenic sites tend to be amphipathic structures", *Proc. Nat'l. Acad. Sci. U.S.A.*, 82:7048-7052 (1985).

Dunbar et al., "Direct isolation, phenotyping and cloning of low-frequency antigen-specific cytotoxic T lymphocytes from peripheral blood", *Curr. Biol.*, 8:413-416 (1998).

Eglitis et al., "Retroviral vectors for introduction of genes into mammalian cells",*BioTechniques*, 6(7):608-614 (1988).

Engelhard, Structure of peptides associated with class I and class II MHC molecules:,*Ann. Rev. Immunol.*, 12:181-207 (1994).

Evan et al., "Isolation of Monoclonal Antibodies Specific for Human c-*myc* Proto-Oncogene Product", *Mol. Cell Biol.*, 5(12):3610-3616 (1985).

Felgner et al., "Lipofection: A highly efficient, lipid-mediated DNA-transfection procedure", *Proc. Nat'l. Acad. Sci. U.S.A.*, 84:7413-7417(1987).

Feltkamp et al., "Efficient MHC Class I-Peptide Binding is Required but does not Ensure MHC Class I-Restricted Immunogenicity",*Mol. Immunol.*, 31(18):1391-1401 (1994).

Feng et al., "The RNA Component of Human Telomerase",*Science*, 269:1236-1241 (1995).

Ferrari et al., "Identification of Immunodominant T Cell Epitopes of the Hepatitis B Virus Nucleocapsid Antigen", *J. Clin. Invest.*, 88:214-222 (1991).

Friedman, T., "Progress Toward Human Gene Therapy", *Science*, 244:1275-1281 (1989).

Gallimore et al., "A protective cytotoxic T cell response to a subdominant epitope is influenced by the stability of the MHC class I/peptide complex and the overall spectrum of viral peptidesgenerated within infected cells", *Eur. J. Immunol.*, 28:3301-3311 (1998).

Gallimore et al., "Protective Immunity Does Not Correlate with the Hierarchy of Virusspecific Cytotoxic T Cell Responses to Naturally Processed Peptides", *J. Exp. Med.*, 187:1647-1657 (1998).

Genbank Accession No. AF018167.1, Aug. 28, 1997, 4 pages.

Gulukota et al., "Two Complementary Methods for Predicting Peptides Binding Major Histocompatibility Complex Molecules",*J. Mol. Biol.*, 267:1258-1267 (1997).

Gulukota et al., "HLA allele selction for designing peptide vaccines", *Genetic Analysis: Biomol. Engineering*, 13:81-86 (1996).

Hammer et al., "New methods to predict HMC-binding sequences within protein antigens", *Curr. Opin. Immunol.*, 7:263-269 (1995).

Hammer et al., "Precise Prediction of Major Histocompatibility Complex Class II-Peptide Interaction Based on Peptide Side Chain Scanning", *J. Exp. Med.*, 180:2353-2358 (1994).

Harle-Bachor et al., "Telomerase activity in the regenerative basal layer of the epidermis in human skin and in immortal and carcinoma-derived skin keratinocytes", *Proc. Natl. Acad. Sci. USA*, 93:6476-6481(1996).

Herr et al., "Detection and quantification of blood-derived CD8+ T lymphocytes secreting tumor necrosis factor α in response to HLA-A2.1-binding melanoma and viral peptide antigens",*J. Immunol. Meth.*, 191:131-142 (1996).

Herr et al., "The use of computer-assisted video image analysis for the quantification of CD8+ T lymphocytes producing tumor necrosis factor αspots in response to peptide antigens", *J. Immunol. Meth.*, 203:141-152 (1997).

Hiyama et al., "Activation of Telomerase in Human Lymphocytes and Hematopoietic Progenitor Cells", *J. Immunol.*, 155:3711-3715 (1995).

Hsu et al., "Tumor-Specific Idiotype Vaccines in the Treatment of Patients With B-Cell Lymphoma—Long-Term Results of a Clinical Trial", *Blood*, 89:3129-3135 (1997).

Igarashi et al., "Telomerase Activity is Induced in Human Peripheral B Lymphocytes by the Stimulation to Antigen Receptor", *Blood*, 89:1299-1307 (1997).

Jager et al., "Immunoselection in Vivo: Independent Loss of MHC Class I and Melanocyte Differentiation Antigen Expression in Metastatic Melanoma",*Int. J. Cancer*, 71:142-147 (1997).

Johnson, L.G., "Gene Therapy for Cystic Fibrosis", *Chest*, 107:77S-83S (1995).

Kammer et al., "Molecular Mimicry of Human Cytochrome P450 by Hepatitis C Virus at the Level of Cytotoxic T Cell Recognition", *J. Exp. Med.*, 190(2):169-176 (1999).
Kido et al., "Use of a retroviral vector with an internal opsin promoter to direct gene expression to retinal photoreceptor cells", *Curr. Eye Res.*, 15:833-844 (1996).
Kim et al., "Advances in quantification and characterization of telomerase activity by the telomeric repeat amplification protocol (TRAP)", *Nuc. Acids Res.*, 25(13):2595-2597 (1997).
Kiyono et al., "Both Rb/p16$^{INK4a}$ inactivation and telomerase activity are required to immortalize human epithelial cells", *Nature*, 396:84-88 (1998).
Klingelhutz et al., "Restoration of Telomeres in Human Papillomavirus-Immortalized Human Anogenital Epithelial Cells", *Mol. Cell. Biol.*, 14(2):961-969 (1994).
Klingelhutz et al., "Telomerase activation by the E6 gene product of human papillomavirus type 16", *Nature*, 380:79-82 (1996).
Kolquist et al., "Expression of *TERT* in early premalignant lesions and a subset of cells in normal tissues", *Nat. Genet.*, 19:182-186 (1998).
Kubo et al., "Definition of specific peptide motifs for four major HLA-A alleles", *J. Imunol.*, 152:3913-3924 (1994).
Kuska, B., "Cancer Genome Anatomy Project Set for Take-off", *J. Nat'l. Cancer Inst.*, 88(24):1801-1803 (1996).
Larvol et al., "In silico drug discovery: Tools for bridging the NCE gap",*Nat. Biotechnol.*, 16(Suppl.):33-34 (1998).
Le Gal La Salle et al., "An Adenovirus Vector for Gene Transfer into Neurons and Gilia in the Brain", *Science*, 259:988-990 (1993).
Lee et al., "Characterization of circulating T cells specific for tumor-associated antigens in melanoma patients", *Nat. Med.*, 5(6):677-685 (1999).
Madden, D.R., "The three-dimensional structure of peptide-MHC complexes", *Ann. Rev. Immunol.*, 13:587-622 (1995).
Malakoff, D., "Biocomputing: NIH Urged to Fund Centers to Merge Computing and Biology",*Science*, 284(5421):1742 (1999).
Mammi et al., Scientific Proceedings 89$^{th}$ Annual Meeting of the American Association for Cancer Research, New Orleans, LA, Mar. 28-Apr. 1, 1998, Abstract #62.
Man et al., "Definition of a human T cell epitope from influenza a non-structural protein I using HLA-A2.1 transgenic mice", *Int. Immunol.*, 7(4):597-605 (1995).
McMichael et al., "A New Look at T Cells", *J. Exp. Med.*, 187(9):1367-1371 (1998).
Meyerson et al., "hEST2, The Putative Human Telomerase Catalytic Subunit Gene, Is Up-Regulated in Tumor Cells and during Immortalization", *Cell*, 90:785-795 (1997).
Miller et al., "Improved Retroviral Vectors for Gene Transfer and Expression",*Biotech.*, 7(9):980-990 (1989).
Miller, A.D., "Retrovirus Packaging Cells", *Human Gene Ther.*, 1:5-14 (1990).
Miyoshi et al., "Stable and efficient gene transfer into the retina using an HIV-based lentiviral vector", *Proc. Nat'l. Acad. Sci. U.S.A.*, 94:10319-10323 (1997).
Moen, R.C., "Directions in Gene Therapy", *Blood Cells*, 17:407-416 (1991).
Molldrem et al., "Targeted T-cell therapy for human leukemia: cytotoxic T lymphocytes specific for a peptide derived from proteinase 3 preferentially lyse human myeloid leukemia cells",*Blood*, 88:2450-2457 (1996).
Morgenstern et al., "Advanced mammalian gene transfer: high titre retroviral vectors with multiple drug selection markers and a complementary helpe-free packaging cell line", *Nucl. Acids Res.*, 18(12):3587-3596 (1990).
Nair et al., "Induction of cytotoxic T cell responses and tumor immunity against unrelated tumors using telomerase reverse transcriptase RNA transfected dendritic cells", Nature Med., 6(8):1011-1017 (2000).
Nakamura et al., "Telomerase Catalytic Subunit Homologs from Fission Yeast and Human", *Science*, 277:955-959 (1997).
Naldini et al., "In Vivo Gene Delivery and Stable Transduction of Nondividing Cells by a Lentiviral Vector", *Science*, 272:263-267 (1996).

Nijman et al., "Identification of peptide sequences that potentially triggerHLA-A2.1-restricted cytotoxic T lymphocytes", *Eur. J. Immunol.*, 23:1215-1219 (1993).
Norrback et al., "Telomerase activation in normal B lymphoctyes and non-Hodgkin's lymphomas", *Blood*, 88:222-229 (1996).
Ono et al., "Plasmid DNAs directly injected into mouse brain with lipofectin can be incorporated and expressed by brain cells", *Neurosci. Lett.*, 117:259-263 (1990).
Pamer et al., "Mechanisms of MHC Class I-restricted antigen processing", *Ann. Rev. Immunol.*, 16:323-358 (1998).
Parker et al., "Peptide Binding to MHC Class I Molecules: Implications for Antigenic Peptide Prediction", *Immunol. Res.*, 14:34-57 (1995).
Parker et al., "Scheme for Ranking Potential HLA-A2 Binding Peptides Based on Independent Binding of Individual Peptide Side-Chains", *J. Immunol.*, 152:163-175 (1994).
Paul, W.E., "Antigen Processing and Presentation", in *Fundamental Immunol.*, 3$^{rd}$ Edition, Chapter 17, Raven Press, Ltd., New York, NY, pp. 629, 641-643 (1993).
Porgador et al., "Localization, Quantitation, and in Situ Detection of Specific Peptide-MHC Class I Complexes Using a Monoclonal Antibody",*Immunity*, 6:715-726 (1997).
Prowse et al., "Developmental and tissue-specific of mouse telomerase and telomere length",*Proc. Natl., Acad. Sci. USA*, 92:4818-4822 (1995).
Rammensee et al., "MHC ligands and peptide motifs: first listing",*Immunogenetics*, 41:178-228 (1995).
Rammensee et al., "Peptides naturally presented by MHC class I molecules",*Ann. Rev. Immunol.*, 11:213-244 (1993).
Riddell et al., "T-cell mediated rejection of gene-modified HIV-specific cytotoxic T lymphocytes in HIV-infected patients", *Nat. Med.*, 2(2):216-223 (1996).
Rock et al., "Degradation of cell proteins and the generation of MHC class I-presented peptides", *Ann Rev Immunol.*, 17:739-779 (1999).
Romero et al., "Ex Vivo Staining of Metastatic Lymph Nodes by Class I Major Histocompatibility Complex Tetramers Reveals High Numbers of Antigen-experienced Tumor-specific Cytolytic T Lymphocytes",*J. Exp. Med.*, 188(9):1641-1650 (1998).
Rosenberg et al., "Gene transfer into humans—immunotherapy of patients with advanced melanoma, using tumor-infiltrating lymphocytes modified by retroviral gene transduction",*N. Engl. J. Med.*, 323:570-578 (1990).
Rosenberg, S.A., "A New Era for Cancer Immunotherapy Based on the Genes that Encode Cancer Antigens", *Immunity*, 10:281-287 (1999).
Rosenberg, S.A., "Cancer vaccines based on the identification of genes encoding cancer regression antigens", *Immunol. Today*, 18(1):175-182 (1997).
Rosenberg et al., "Immunologic and therapeutic evaluation of a synthetic peptide vaccine for the treatment of patients with metastatic melanoma",*Nat. Med.*, 4(3):321-327 (1998).
Rothbard et al., "Interactions between immunogenic peptides and MHC proteins", *Ann. Rev. Immunol.*, 9:527-565 (1991).
Ruppert et al., "Prominent Role of Secondary Anchor Residues in Peptide Binding to HLA-A2.1 Molecules", *Cell*, 74:929-937 (1993).
Sahin et al., "Serological identification of human tumor antigens", *Curr. Opin. Immunol.*, 9:709-716 (1997).
Salter et al., "Impaired assembly and transport of HLA-A and -B antigens in a mutant TxB cell hybrid", *EMBO J.*, 5(5):943-949 (1986).
Sarma et al., "Cytotoxic T Lymphocytes to an Unmuated Tumor Rejection Antigen P1A: Normal Development but Restrained Effector Function in Vivo",*J. Exp. Med.*, 189(5):811-820 (1999).
Savage et al., "A Kinetic Basis for T Cell Receptor Repertoire Selection during an Immune Response", *Immunity*, 10:485-492 (1999).
Scheibenbogen et al., "A Sensitive ELISPOT Assay for Detection of CD8$^+$ T Lymphocytes Specific for HLA Class I-binding Peptide Epitopes Derived from Influenza Proteins in the Blood of Healthy Donors and Melanoma Patients", *Clin. Cancer Res.*, 3:221-226 (1997).
Scheibenbogen et al., "Analysis of the T Cell Response to Tumor and Viral Peptide Antigens by an IFNγ-ELISPOT Assay", *Int. J. Cancer*, 71:932-936 (1997).

Schmittel et al., "Evaluation of the interferon-γ ELISPOT-assay for quantification of peptide specific T lymphocytes from peripheral blood", *J. Immunol. Meth.*, 210:167-174 (1997).

Schonbach et al., "Fine Tuning of Peptide Binding to HLA-B*3501 Molecules by Nonanchor Residues", *J. Immunol.*, 154:5951-5958 (1995).

Schultze et al., "Human Non-Germinal Center B Cell Interleukin (IL)-12 Production is Primarily Regulated by t Cell Signals CD40 Ligand, Interferon γ, and IL-10: Role of B Cells in the Maintenance of T Cell Responses", *J. Exp. Med.*, 89(1):1-11 (1999).

Schumacher et al., "Direct Binding of Peptide to Empty MHC Class I Molecules on Intact Cells and in Vitro", *Cell*, 62:563-567 (1990).

Sette et al., "The Relationship Between Class I Binding Affinity and Immunogenicity of Potential Cytotoxic T Cell Epitopes", *J. Immunol.*, 153:5586-5592 (1994).

Sharp, D, "Gene Therapy", *Lancet*, 337:1277-1278 (1991).

Sidney et al., "Practical, biochemical and evolutionary implications of the discovery of HLA class I supermotifs", *Immunol. Today*, 17(6):261-266 (1996).

Stöppler et al., "The Human Papillomavirus Type 16 E6 and E7 Oncoproteins Dissociate Cellular Telomerase Activity from the Maintenance of Telomere Length", *J. Biol. Chem.*, 272(20):13332-13337 (1997).

Straubinger et al., "Liposomes as Carriers for Intracellular Delivery of Nucleic Acids", *Meth. Enz.*, 101:512-527 (1983).

Tolstoshev et al., "Gene expression using retroviral vectors", *Curr. Opin. Biotech.*, 1:55-61 (1990).

Tompkins et al., "A europium fluoroimmunoassay for measuring binding of antigen to class II MHC glycoproteins", *J. Immunol. Meth.*, 163:209-216 (1993).

Townsend et al., "Assembly of MHC Class I Molecules Analyzed in Vitro", *Cell*, 62:285-295 (1990).

Valmori et al., "An Antigen-targeted Approach to Adoptive Transfer Therapy of Cancer", *Cancer Res.*, 59:2167-2173 (1999).

Van den Eynde et al., "T cell defined tumor antigens", *Curr. Opin. Immunol.*, 9:684-693 (1997).

Van der Burg et al., "Immunogenicity of Peptides Bound to MHC Class I Molecules Depends on the MHC-Peptide Complex Stability", *J. Immunol.*, 156:3308-3314 (1996).

Van Pel et al., "Genes Coding for Tumor Antigens Recognized by Cytolytic T Lymphocytes", *Immunol. Rev.*, 145:229-250 (1995).

Weng et al., "Telomere lengthening and telomerase activation during human B cell differentiation", *Proc. Nat'l. Acad. Sci. U.S.A.*, 94:10827-10832 (1997).

Wentworth et al., "Identification of A2-restricted hepatitis C virus-specific cytotoxic T lymphocyte epitopes from conserved regions of the viral genome", *Int. Immunol.*, 8(5):651-659 (1996).

Wolff et al., "Direct Gene Transfer into Mouse Muscle in Vivo", *Science*, 247:1465-1468 (1990).

Wu et al., "Receptor-mediated Gene Delivery and Expression in Vivo" *J. Biol. Chem.*, 263(29):14621-14624 (1988).

Wu et al., "Targeting Genes: Delivery and Persistent Expression of a Foreign Gene Driven by Mammalian Regulatory Elements in Vivo", *J. Biol. Chem.*, 264(29):16985-16987 (1989).

Yasumoto et al., "Telomerase activity in normal human epithelial cells", *Oncogene*, 13:433-439 (1996).

Yee et al., "Isolation of High Avidity Melanoma-Reactive CTL from Heterogeneous Populations Using Peptide-MHC Tetramers", *J. Immunol.*, 162:2227-2234 (1999).

Letter dated Apr. 29, 2008, enclosing Form 1037, Re: European SApplication No. 99956777.9-2402/1126872, 5 pages (2008).

Priority Document for Patent Application No. 19983141, "Antigenic Peptides", Gaudernack et al., Norway, 40 pages (1999).

Priority Document dated Apr. 12, 1999, for U.S. Appl. No. 60/112,006, filed Mar. 31, 1998, PCT Application No. PCT/US99/06898, 29 pages.

Notice of Opposition to European Patent No. 1 126 872, in the name of Dana-Farber Cancer Institute, Inc. & Whitehead Institute for Biomedical Research, by Geron Corporation, dated Sep. 13, 2007, 22 pages.

Notice of Opposition to European Patent No. 1126872 in the name of Dana-Farber Cancer Institute, Inc. & Whitehead Institute for Biomedical Research, by Merck & Co., Inc., dated Sep. 13, 2007, 13 pages.

* cited by examiner

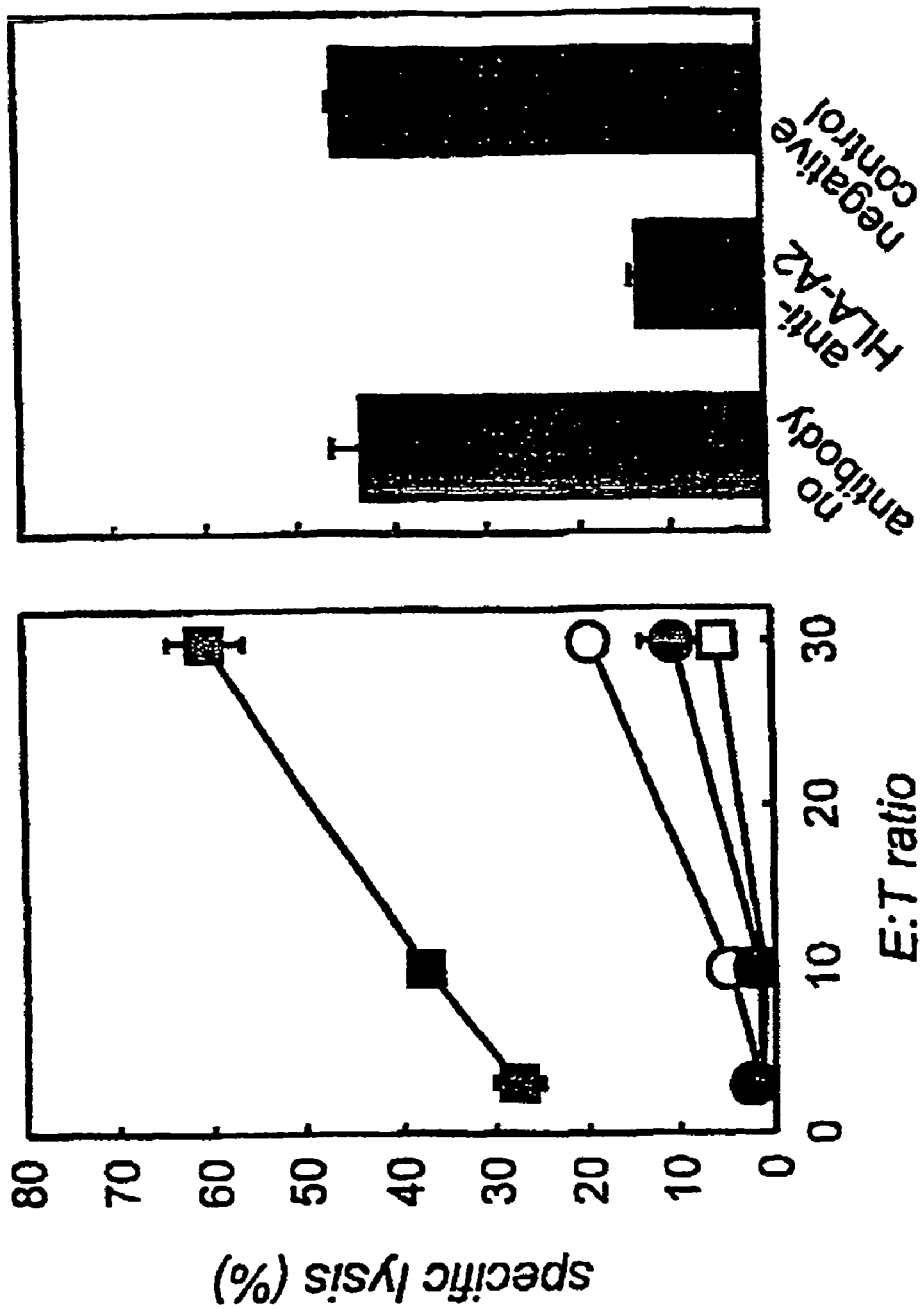
Fig. 2 (A-B)

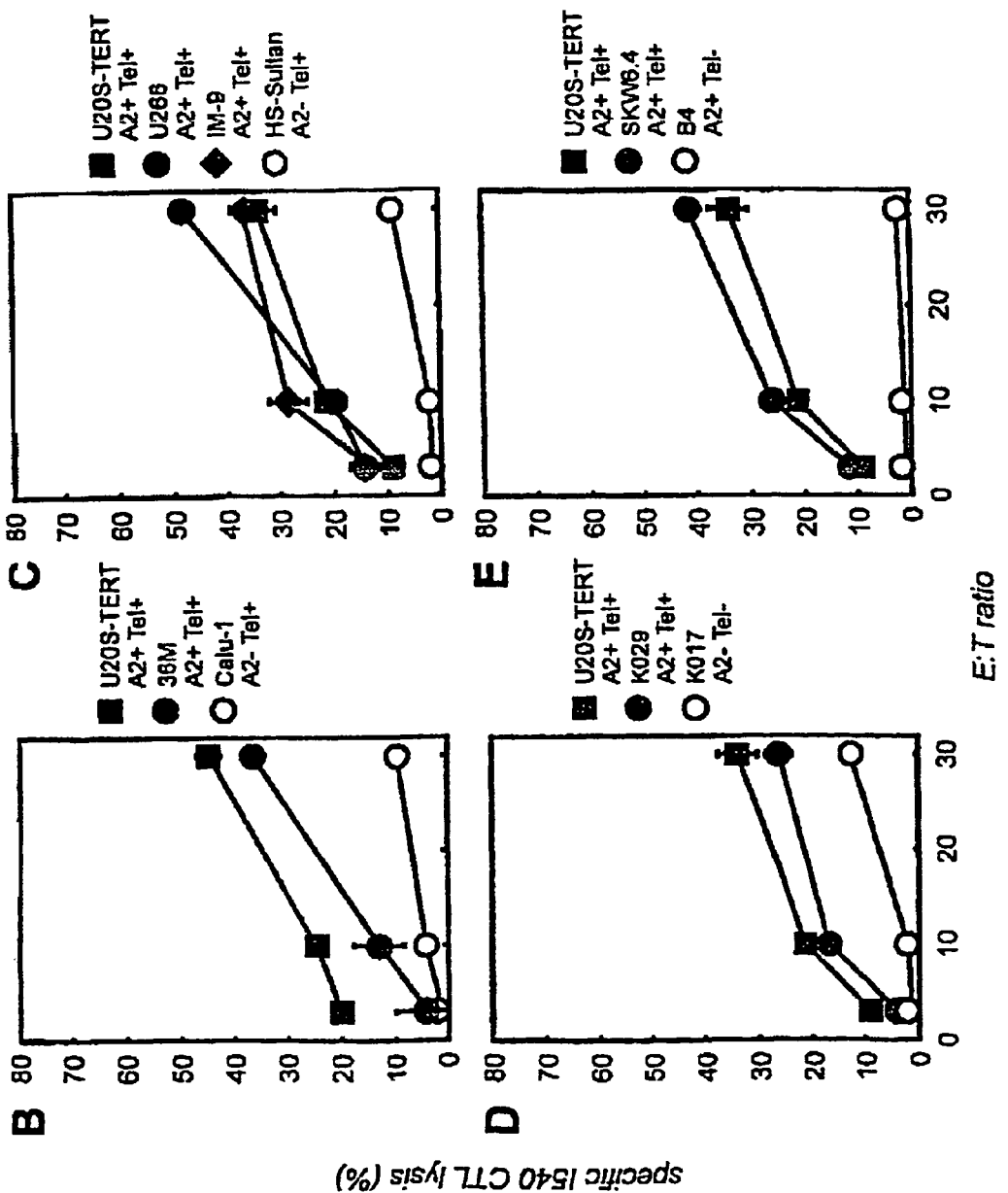
Fig. 3 (B-E)

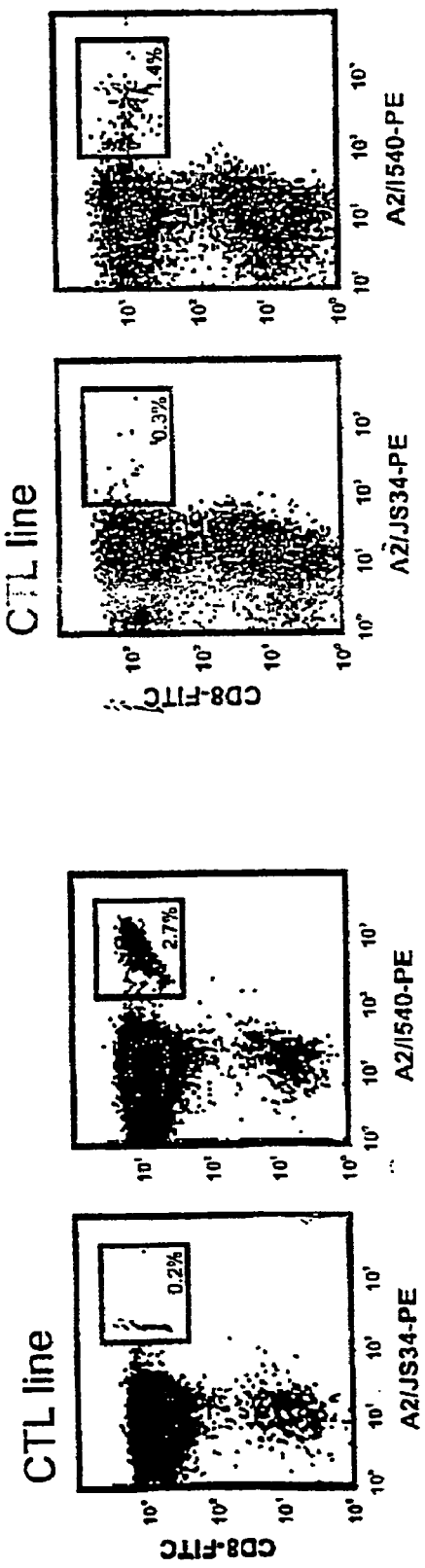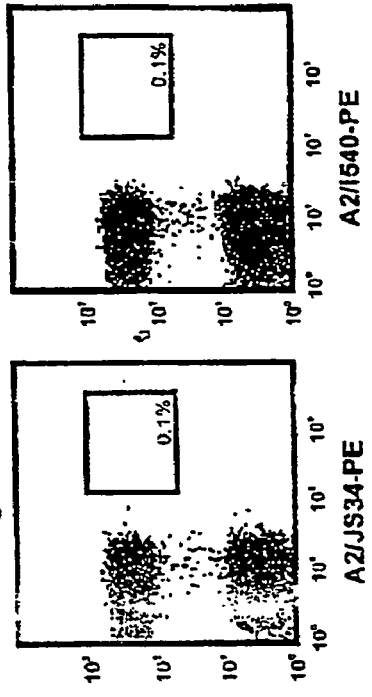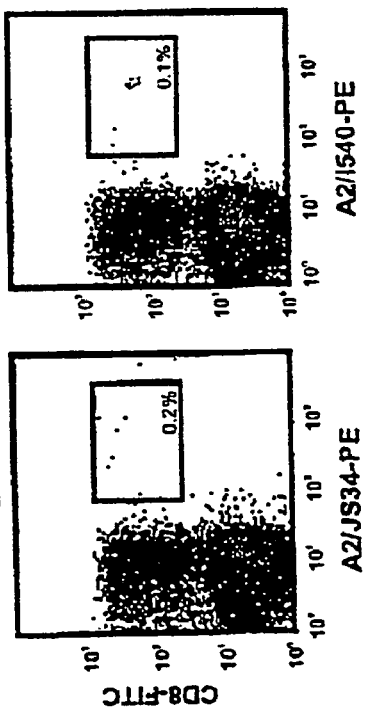
Fig. 9

CANCER IMMUNOTHERAPY AND DIAGNOSIS USING UNIVERSAL TUMOR ASSOCIATED ANTIGENS, INCLUDING HTERT

This application is the 371 national stage entry of PCT/US99/25438, filed Oct. 29, 1999, which claims priority to U.S. provisional application 60/106,106, filed Oct. 29, 1998.

BACKGROUND OF THE INVENTION

This invention relates to methods of identifying universal tumor associated antigens, and use of such antigens in the prevention, treatment, and diagnosis of cancer.

The paucity of clinically significant anti-tumor immune responses in cancer patients has long suggested that antigen-specific immunotherapy would not play a significant role in cancer treatment. However, pioneering studies in the early 1990s, using tumor-specific cytotoxic T lymphocytes (CTLs) from cancer patients, showed the existence of human tumor associated antigens (TAAs), suggesting that such antigens could be used to stimulate therapeutic anti-tumor immune responses in patients. Although these studies primarily focused on melanoma, TAAs have been subsequently characterized in several other malignancies, raising the hypothesis that most, if not all, tumors express antigens that can be used to induce CTL-mediated tumor destruction. Consequently, exciting clinical efforts are now underway to target these TAAs in strategies such as vaccination and adoptive T cell therapy to generate effective anti-tumor CTL responses in patients.

Unfortunately, most TAAs described thus far are expressed in only one or a few tumor types, and not all patients with a given tumor type express the associated TAA. As a result, progress in the field of cancer immunotherapy has been relatively slow, because it has not been possible to develop widely useful TAA-specific immunotherapeutic strategies. Not only has it been necessary to tailor such therapies to individual types of malignancies, in some cases (such as the immunoglobulin idiotypic antigen in B cell malignancies), it has been necessary to tailor these therapies to individual patients.

More than 85% of human cancers display telomerase activity (Kim et al., Science 266:2011-2015, 1994). Telomerase is a ribonucleoprotein complex that maintains the telomeric ends of linear chromosomes, thus protecting them from degradation and end-to-end fusion. The human telomerase complex contains a reverse transcriptase, known as hTERT, and an RNA component that is used as a template for telomere synthesis by hTERT. The hTERT subunit is the rate-limiting component of the complex, and its expression correlates best with telomerase activity. Most human cells do not express hTERT or display telomerase activity, and therefore lose telomeric DNA with each cell division. In contrast, more than 85% of human tumors express hTERT, exhibit strong telomerase activity, and maintain the length of their telomeres, suggesting that the activation of telomerase plays an important role in the development of human cancers.

SUMMARY OF THE INVENTION

The invention provides a method of treating a patient that has or is at risk of having a cell that expresses hTERT. This method involves administering to the patient a cytotoxic T lymphocyte (CTL) (autologous or allogeneic) that kills the cell in an hTERT-specific, major histocompatibility complex-restricted fashion. The CTL can be generated, for example, by activation with an antigen presenting cell that has been pulsed with hTERT, or a peptide of hTERT that binds to a major histocompatibility complex molecule.

The invention also includes a second method of treating a patient that has or is at risk of having a cell that expresses hTERT. This method involves administering to the patient an antigen presenting cell (APC) that activates in the patient a cytotoxic T lymphocyte that kills the cell in an hTERT-specific, major histocompatibility complex-restricted fashion. The APC can be pulsed with hTERT or a peptide of hTERT that binds to a major histocompatibility complex molecule.

Another method included in the invention is a third method of treating a patient that has or is at risk of having a cell that expresses hTERT. This method involves administering to the patient hTERT or a peptide of hTERT that binds to a major histocompatibility complex molecule, which is processed by an antigen presenting cell in the patient, which, in turn, activates a cytotoxic T lymphocyte in the patient to kill the cell that expresses hTERT in an hTERT-specific, major histocompatibility complex-restricted fashion. The hTERT or peptide of hTERT used in this method can be administered to the patient in association with an adjuvant.

The invention also includes a fourth method of treating a patient that has is at risk of having a cell that expresses hTERT. This method involves administering to the patient a nucleic acid molecule encoding hTERT or a peptide of hTERT that binds to a major histocompatibility complex molecule. The nucleic acid molecule is expressed in the patient so that it can be processed by an antigen presenting cell in the patient, which activates a cytotoxic T lymphocyte in the patient to kill the cell that expresses hTERT in an hTERT-specific, major histocompatibility complex-restricted fashion. The nucleic acid molecule encoding hTERT or a peptide of hTERT can be present in an expression vector.

In any of the methods described above, the patient can have a tumor containing cells that express hTERT. APCs used in these methods can be, for example, a dendritic cell or a CD40-activated B cell. The peptide of hTERT in these methods can bind to a class I or a class II major histocompatibility complex (MHC) molecule. In the case of a class I MHC molecule, the molecule can be an HLA-A2 molecule or an HLA-A3 molecule (also see below). In the case of an HLA-A2 molecule, the peptide of hTERT can include the amino acid sequence of SEQ ID NO:1. In the case of an HLA-A3 molecule, the peptide of hTERT can include the amino acid sequence of SEQ ID NO:2. Examples of other hTERT sequences that can be used in these methods are listed below.

The invention also includes a method of assessing the level of immunity of a patient to hTERT or a peptide of hTERT that binds to a major histocompatibility complex molecule. In this method, the level of cytotoxic T lymphocytes specific for hTERT or a peptide of hTERT is measured in a sample from the patient. The sample can be obtained from the patient before, during, or after a cancer treatment is administered to the patient. A sample can also be obtained, for example, before and after treatment.

The invention also includes an hTERT peptide that binds to a major histocompatibility complex molecule, for example, a peptide that consists essentially of the amino acid sequence set forth in SEQ ID NO:1 or SEQ ID NO:2 (also see below).

Also included in the invention is an ex vivo generated cytotoxic T lymphocyte that specifically kills a cell expressing hTERT in a specific, major histocompatibility complex-restricted fashion, and an ex vivo generated antigen presenting cell (e.g., a dendritic cell or a CD40-activated B cell) that presents a peptide of a hTERT in the context of a major histocompatibility complex molecule.

The invention also includes a method for identifying a universal tumor associated antigen. This method involves: (a) analyzing one or more databases to identify a gene that is: (i) expressed in more than one human tumor type, and (ii) expressed in at least one human tumor type at a level that is at least 3-fold (e.g., 5-fold or 10-fold) higher than the level at which it is expressed in a normal human cell; (b) using a computer-run algorithm to identify an amino acid sequence in the protein encoded by the gene that is predicted bind to a major histocompatibility complex molecule (e.g., a class I or class II major histocompatibility molecule); (c) synthesizing an immunogen that comprises the amino acid sequence identified in step (b), or a sequence that is predicted by a computer-run algorithm to bind to a major histocompatibility complex molecule with higher affinity than the sequence; and (d) testing the ability of the immunogen to stimulate a major histocompatibility complex-restricted cytotoxic T lymphocyte response that is specific for the protein.

The peptide, preferably, is predicted to bind to MHC with a probability of at least, e.g., 30%, 40%, 50%, 60%, 70%, 80%, 90%, or 100%. It also, preferably, binds to MHC with at least intermediate affinity (e.g., with an IC50 of about 51-500 nM), for example, with high affinity (e.g., with an IC50 of up to 50 nM).

This method can also include, after step (d), testing the ability of a major histocompatibility complex-restricted cytotoxic T lymphocyte that is specific for the universal tumor associated antigen and is generated in step (d) to kill a malignant cell expressing the universal tumor associated antigen and not a non-malignant cell.

Also, the method can include, after step (c) and prior to step (d), using a time-resolved, fluorometry-based assay to measure MHC binding and MHC/peptide complex stability of a peptide comprising the amino acid sequence identified in step (b).

The testing of the immunogen can be carried out by contacting a cytotoxic T lymphocyte with an antigen presenting cell (e.g., a dendritic cell or a CD40-activated B cell) that has been pulsed with the immunogen.

The methods of the invention described above with respect to hTERT can also be carried out with any universal tumor associated antigens or MHC-binding peptides thereof that are identified using the above-described method. Also, the invention includes a universal tumor-associated antigen or a peptide thereof that binds to a major histocompatibility complex molecule; an ex vivo generated cytotoxic T lymphocyte that specifically kills a cell expressing a universal tumor-associated antigen in a specific, major histocompatibility complex-restricted fashion; and an ex vivo generated antigen presenting cell that presents a peptide of a universal tumor-associated antigen in the context of a major histocompatibility complex molecule.

As is understood in the art, a "polypeptide" is a chain of amino acids linked to one another by peptide bonds. A "protein" can be made up of one or more polypeptides, while a "peptide" is generally understood to be (or include) a fragment of a polypeptide, and to consist of a chain of peptide bond-linked amino acids that is shorter in length than a full length polypeptide from which it may be derived.

A "tumor associated antigen" is an immunogenic molecule, such as a protein, that is, generally, expressed at a higher level in tumor cells than in non-tumor cells, in which, preferably, it may not be expressed at all, or only at low levels. A tumor associated antigen, or TAA, is said to be "universal" if it is expressed in tumors of different origins. For example, as is discussed above, the catalytic subunit of telomerase, hTERT, is expressed in more than 85% of human cancers, and thus is a universal tumor antigen. Other antigens qualifying as universal TAAs could be, for example, expressed in at least three, for example, four, five, six, seven, eight, or more different types of tumors.

A "tumor associated antigen polypeptide," or a "TAA polypeptide" is a full length, non-fragmented polypeptide of a tumor associated antigen, while a "tumor associated antigen peptide," or a "TAA peptide," is (or includes) a fragment of such a TAA polypeptide. TAA peptides can be of any length, up to just under the full length of a TAA polypeptide. However, preferably, for use in the invention, TAA peptides are of a relatively short length, such as, for example, eight, nine, ten, eleven, or twelve amino acids. Also, a TAA peptide may include sequences that are not present in a corresponding TAA polypeptide, provided that the TAA peptide also includes a stretch of at least, for example, eight, nine, ten, eleven, or twelve consecutive amino acids that have a sequence that is identical to a sequence of eight, nine, ten, eleven, or twelve consecutive amino acids in a TAA polypeptide.

Peptides including amino acid substitutions can also be considered as TAA peptides. For example, a TAA peptide can include a region of at least nine amino acids, of which any six or more are identical to the amino acids within a nine amino acid stretch in a given TAA. Preferably, at least seven, more preferably, at least eight, and, most preferably, all nine of the amino acids in a TAA peptide nine amino acid region are identical to a nine amino acid region in the TAA.

A TAA polypeptide corresponding to hTERT includes 1132 amino acids that are substantially identical (see below) to the amino acid sequence of hTERT, or such a polypeptide can include the amino acid sequence of hTERT, as well as additional sequences.

As is discussed further below, it is preferable that TAA polypeptides of the invention include regions that bind to major histocompatibility complex (MHC) antigens. Similarly, it is preferable that TAA peptides of the invention bind to MHC antigens.

By "hTERT" is meant the catalytic subunit of human telomerase (see, e.g., Genbank Accession No. AF018167). Preferred examples of hTERT peptides that are included in the invention are the peptides I540 (SEQ ID NO:1) and K973 (SEQ ID NO:2), as described herein. Additional hTERT peptides are described below, and still more hTERT peptides can be identified using methods described below.

A TAA (e.g., hTERT) peptide or polypeptide can be fused to amino acid sequences that do not naturally occur in the TAA. Moreover, a TAA peptide or polypeptide can be attached to the surface of a cell or to a molecule or a macromolecule (e.g., a histocompatibility antigen), or a TAA peptide or polypeptide can be conjugated to immunogens or adjuvants that are known to those of skill in this art, for example, keyhole limpet hemocyanin (KLH), for the purpose of eliciting a TAA-specific immune response. Preferred examples of hTERT peptides are the peptides I540 (SEQ ID NO:1) and K973 (SEQ ID NO:2), as described herein.

By "TAA nucleic acid molecule" is meant a DNA or RNA (e.g., mRNA) molecule that encodes a TAA peptide or TAA polypeptide, as are defined above.

By "TAA-expressing tumor cell" is meant a tumor cell that expresses a given TAA (e.g., hTERT). A TAA-expressing tumor cell can express a level of TAA that is equal to, or, preferably, greater than the level of TAA expressed by the normal cell type from which the TAA-expressing tumor cell has originated, or other non-tumor cells. Preferably, the tumor cell expresses at least 10% more TAA, more preferably, at least 25% more, still more preferably at least 50% more, and most preferably at least 150% more TAA than the normal cell type from which the TAA-expressing tumor cell has originated, or another non-tumor cell. TAA expression levels in a TAA-expressing tumor cell can be increased by, for example, increased transcription of the TAA gene, increased TAA mRNA stability or translation, increased TAA polypeptide stability, or increased TAA enzymatic activity. Increasing such TAA expression levels may be useful in the invention to increase the likelihood that a tumor cell will be recognized as a target of the immunotherapeutic methods described herein.

By "histocompatibility antigen" is meant a molecule, such as a major histocompatibility complex (MHC) class I, MHC class II, or minor histocompatibility antigen, that mediates interactions of cells of the immune system with each other and with other cell types. Examples of histocompatibility antigens include MHC class I antigens, such as HLA-A (e.g., A1, A2, A3, All, A24, A31, A33, and A38), -B, and -C, MHC class II antigens, such as HLA-DR, -DQ, -DX, -DO, -DZ, and -DP, and minor histocompatibility antigens, such as HA-1.

By "generating CTLs" is meant an in vivo, in vitro, or ex vivo process by which TAA (e.g., hTERT)-specific CTLs are activated (e.g., stimulated to grow and divide) and/or selected.

A peptide of a TAA, such as hTERT, is said to "specifically bind" to an MHC antigen if the peptide adheres to a histocompatibility antigen under physiological conditions. For example, such binding can be similar to that of a peptide antigen that is naturally processed and presented in the context of MHC in an antigen presenting cell.

A cytotoxic T lymphocyte (CU) or antibody is said to "specifically recognize" a TAA polypeptide (e.g., hTERT) or a TAA peptide if it binds to the polypeptide or peptide, but does not substantially bind to other, unrelated polypeptides or peptides.

A CTL is said to "specifically kill" a cell if it specifically recognizes and lyses a cell that expresses a TAA (e.g., hTERT) to which it has been activated, but does not substantially recognize or lyse cells not expressing the TAA. Such a CTL is designated as a "TAA-specific CTL" herein.

By "TAA-specific antibody" is meant an antibody that can specifically recognize and bind to a TAA (e.g., hTERT) peptide or polypeptide, and does not substantially recognize and bind to other, unrelated molecules.

A TAA (e.g., hTERT) is "presented" if a peptide of the TAA is displayed on the extracellular surface of a cell (e.g., an antigen presenting cell), such that it can result in the in vivo, ex vivo, or in vitro generation of TAA-specific CTLs or the lysis of a tumor cell by a TAA-specific CTL. Preferably, the displayed TAA peptide is bound to a histocompatibility antigen.

By "physiological conditions" is meant the in vivo environment in which TAA (e.g., hTERT)-specific CTLs are generated (activated and/or selected) and perform their biological functions (e.g., recognition of the TAA peptide and MHC-restricted lysis of TAA-expressing tumor cells), or an in vitro or ex vivo environment that allows TAA-specific CTLs to be generated and to perform their biological functions.

By "vaccination" is meant administration of an immunogenic preparation including one or more TAA (e.g., hTERT) peptides, TAA polypeptides, TAA nucleic acid molecules, fragments of any of these molecules, TAA-presenting cells (e.g., dendritic cells or CD40-activated B cells), or mixtures thereof. Vaccination is performed on a subject who has a tumor, has a history of having a tumor or tumors, or is likely to develop a tumor, or to a subject in which TAA-specific immune cells (such as CTLs) are to be generated for transfer into a patient. Vaccination stimulates a TAA-specific immune response within the subject. In subjects having tumors, the vaccination can result in partial or complete inhibition of tumor growth, or partial or complete tumor regression, provided that the patient's tumor expresses the TAA. In addition, vaccination can provide prophylaxis against the development of new TAA-expressing tumors.

A "vaccine," as used herein, is an immunogenic composition that can be administered in the vaccination method described above. Thus, a vaccine includes, for example, one or more TAA (e.g., hTERT) peptides, TAA polypeptides, TAA nucleic acid molecules, fragments of any of these molecules, TAA-presenting cells (e.g., dendritic cells or CD40-activated B cells), or mixtures thereof. Optionally, a vaccine composition can also include an adjuvant, which is a molecule that stimulates an immune response to the co-administered vaccine antigen. Examples of adjuvants that can be used in the invention are provided below.

By "immune cell" is meant any cell that plays a role in cell-mediated or humoral immunity, including CTLs and antigen-presenting cells, e.g., B cells, T helper cells, and dendritic cells.

By "sample" is meant a tumor or tissue biopsy, a lymph node biopsy, bone marrow, cells, blood, serum, urine, stool, sputum, saliva, or other specimen obtained from a patient. A sample can be analyzed to determine the level of TAA (e.g., hTERT)-specific CTLs, the level of TAA-specific antibodies, or the level of any other immune response indicator (e.g., cytokine level) in the patient from whom it was taken, by methods that are known in the art. For example, ELISA can be used to measure levels of TAA-specific antibodies, and ELISPOT can be used to measure cytokine levels. Also, $Cr^{51}$ release (T cell cytotoxicity) assays and assays that test the binding of CTLs to tetrameric TAA peptide/MHC complexes, as described herein, can be used to measure levels of TAA-specific CTLs.

By "reference sample" is meant a sample in which the levels of TAA (e.g., hTERT)-specific CTLs or the level of TAA-specific antibodies have been measured, and to which the level of TAA-specific CTLs or the level of TAA-specific antibodies in a test subject's sample are compared. Reference levels can be higher, lower, or the same as patient sample levels. Comparison of a test sample to a reference sample provides an assessment of the TAA-specific immune response in the test subject. In addition, comparison of a patient's sample levels to reference sample levels can allow a diagnosis of cancer and/or a prognosis of a cancer, in a patient having a tumor that comprises TAA-expressing cells.

By "cancer treatment" is meant any therapy (e.g., chemotherapy, radiation therapy, administration of TAA (e.g., hTERT)-specific CTLs, administration of an APC presenting a peptide of a TAA, or vaccination with a TAA, a nucleic acid molecule encoding a TAA, or a fragment thereof, to enhance an anti-tumor immune response) administered either alone or in combination with other therapies, that alleviates disease in at least some patients to which the treatment is administered. For example, a cancer treatment can reduce or inhibit tumor growth, or can induce partial or complete tumor regression. Furthermore, a cancer treatment can be prophylactic, in that it inhibits or prevents the development of new tumors in patients that are in remission from cancer, have metastatic cancer, or have a high risk of developing cancer.

By "inhibiting the development of a tumor" is meant administering a protective therapy (such as TAA (e.g., hTERT)-specific CTLs, TAA peptide presenting APCs, or a vaccine including, for example, one or more TAA peptides, TAA polypeptides, or TAA nucleic acid molecules, or a combination thereof) to a subject adjudged to have a higher than average risk of developing a tumor. Subjects with a relatively high risk of developing a tumor include those having a family history of cancer, those having one or more genetic mutations that are associated with a high risk for cancer (e.g., a mutation that inactivates a tumor suppressor gene), those having relatively high levels of TAA-specific CTLs or TAA-specific antibodies, those who have cancer or are in remission from cancer, and those who have been exposed to agents known or suspected to cause cancer.

By "pharmaceutically acceptable carrier" is meant a carrier that is physiologically acceptable to a treated patient, while retaining the therapeutic properties of the compound with which it is administered. One exemplary pharmaceutically acceptable carrier is physiological saline. Other physiologically acceptable carriers and their formulations are known to one skilled in the art, and described, for example, in *Remington's Pharmaceutical Sciences* (18$^{th}$ edition), ed. A. Gennaro, 1990, Mack Publishing Company, Easton, Pa.

By "substantially identical" is meant a polypeptide or nucleic acid molecules exhibiting at least 50%, preferably at least 85%, more preferably at least 90%, and most preferably at least 95% identity to a reference amino acid or nucleic acid sequence. For polypeptides, the length of comparison sequences is at least 16 amino acids, preferably at least 20 amino acids, more preferably at least 25 amino acids, and most preferably 35 amino acids. For nucleic acid molecules, the length of comparison sequences is at least 50 nucleotides, preferably at least 60 nucleotides, more preferably at least 75 nucleotides, and most preferably at least 110 nucleotides. Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). The TAA polypeptides, peptides, and nucleic acid molecules of the invention can be identical or substantially identical to naturally occurring molecules, and thus may or may not include non-wild type sequences.

By "substantially pure peptide" or "substantially pure polypeptide" is meant a peptide, polypeptide, or a fragment thereof, that has been separated from the components that naturally accompany it. Typically, the peptide or polypeptide is substantially pure when it is at least 60%, by weight, free from the proteins and naturally-occurring organic molecules with which it is naturally associated. Preferably, the peptide or polypeptide is a TAA (e.g., hTERT) peptide or polypeptide that is at least 75%, more preferably at least 90%, and most preferably at least 99%, by weight, pure. A substantially pure TAA peptide or polypeptide can be obtained, for example, by extraction from a natural source (e.g., a tumor cell), by expression of a recombinant nucleic acid molecule encoding a TAA (e.g., hTERT) peptide or polypeptide, or by chemically synthesizing the peptide or polypeptide. Purity can be measured by any appropriate method, e.g., by column chromatography, polyacrylamide gel electrophoresis, or HPLC analysis.

A protein is substantially free of naturally associated components when it is separated from those contaminants that accompany it in its natural state. Thus, a protein that is chemically synthesized or produced in a cellular system different from the cell from which it naturally originates is substantially free from its naturally associated components. Accordingly, substantially pure peptides and polypeptides not only include those derived from eukaryotic organisms but also those synthesized in *E. coli* or other prokaryotes.

By "substantially pure DNA" or "isolated DNA" is meant DNA that is free of the genes that, in the naturally-occurring genome of the organism from which the DNA is derived, flank the gene. The term thus includes, for example, a recombinant DNA that is incorporated into a vector; an autonomously replicating plasmid or virus; or the genomic DNA of a prokaryote or eukaryote; or DNA that exists as a separate molecule (e.g., a cDNA, or a genomic or cDNA fragment produced by PCR or restriction endonuclease digestion) independent of other sequences. It also includes a recombinant DNA that is part of a hybrid gene encoding additional polypeptide sequence.

By "transformation" is meant any method for introducing foreign molecules into a cell. Lipofection, DEAE-dextran-mediated transfection, microinjection, protoplast fusion, calcium phosphate precipitation, transduction (e.g., bacteriophage, adenoviral retroviral, or other viral delivery), electroporation, and biolistic transformation are just a few of the methods known to those skilled in the art which can be used in the invention.

By "transformed cell," "transfected cell," or "transduced cell," is meant a cell (or a descendent of a cell) into which a nucleic acid molecule (e.g., a DNA or RNA molecule) encoding a polypeptide of the invention has been introduced, by means of recombinant DNA techniques.

By "promoter" is meant a minimal sequence sufficient to direct transcription. Promoter elements that are sufficient to render promoter-dependent gene expression controllable for cell type-specific, tissue-specific, temporal-specific, or inducible by external signals or agents can also be used in the invention; such elements can be located in the 5' or 3' or intron sequence regions of the native gene.

By "operably linked" is meant that a gene and one or more regulatory sequences are connected in such a way as to permit gene expression when the appropriate molecules (e.g., transcriptional activator proteins) are bound to the regulatory sequences.

By "expression vector" is meant a genetically engineered plasmid or virus, derived from, for example, a bacteriophage, adenovirus, retrovirus, poxvirus, herpesvirus, or artificial chromosome, that is used to transfer a peptide or polypeptide coding sequence (e.g., a TAA (e.g., hTERT) peptide coding sequence), operably linked to a promoter, into a host cell, such that the encoded peptide or polypeptide is expressed within the host cell.

Other features and advantages of the invention will be apparent from the drawings, following detailed description, and the claims.

BRIEF DESCRIPTION OF THE DRAWINGS

FIGS. 2A and 2B are a pair of graphs showing hTERT-specific, HLA-restricted CTL-mediated lysis of U20S cells expressing hTERT, and inhibition, using an anti-HLA antibody, of hTERT-specific, HLA-restricted CTL-mediated lysis of U205 cells expressing hTERT.

FIGS. 3B-3E is a series of graphs showing hTERT-specific, HLA-restricted CTL-mediated lysis of carcinoma (3B), multiple myeloma (3C), malignant melanoma (3D), and EBV-transformed B cell (3E) cell lines.

FIG. 9 is a series of panels showing the results of tetramer analysis of donor and cancer patient samples for I540 CTLs.

DETAILED DESCRIPTION

Figure 1A:
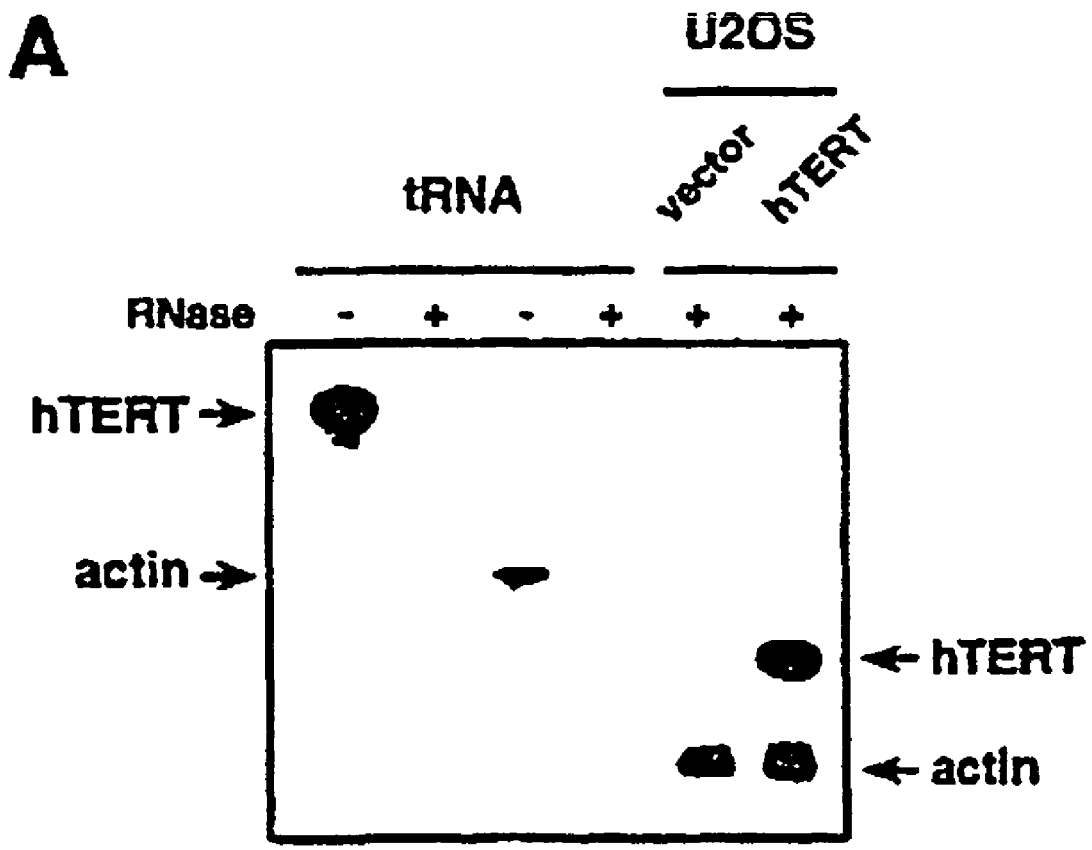
FIG. 1A is an autoradiogram of an RNase protection assay showing expression of hTERT in U20S osteosarcoma cells infected with a retroviral rector encoding hTERT.

We have discovered that the catalytic subunit of human telomerase, hTERT, includes peptides that bind HLA class I molecules. Antigen presenting cells (APCs) that present such peptides on their surfaces, in complexes with HLA, can activate cytotoxic T lymphocytes (CTLs) to specifically lyse cells expressing hTERT, in an MHC-restricted fashion. The invention thus provides methods for immunotherapeutic targeting of hTERT expressing cells, such as cancer cells.

The also invention provides (i) methods of identifying and characterizing universal tumor associated antigens (TAAs), (ii) methods of using such antigens (e.g., the telomerase catalytic subunit, hTERT), and MHC-binding peptides of these antigens, in the prevention or treatment of cancer and other conditions characterized by excessive cell proliferation, and (iii) methods of monitoring the efficacy of such prevention and treatment methods.

I. Methods of Identifying and Characterizing Universal Tumor Associated Antigens (TAAs)

As is mentioned above, there is now compelling evidence in murine model systems and in humans that immunotherapy can be used to induce immune responses against cancer. The role of major compartments of the immune system in such anti-tumor responses has been studied in great detail (Rosenberg, Immunity 10:281-287, 1999). Cellular and molecular interactions during the induction (priming), amplification (expansion), and effector phases of an anti-tumor immune response have been elucidated. The identification of genes encoding tumor associated antigens recognized by T and B cells has given cancer immunotherapy a molecular basis (Boon et al., Annual Review of Immunology 12:337-365, 1994; Sahin et al., Curr. Opin. Immunol. 9:709-716, 1997). Moreover, with the identification of the dendritic cell (DC) as the most prominent antigen presenting cell (APC), a novel cellular adjuvant has been introduced into the armamentarium of immunotherapy.

However, despite these developments, there have been several important obstacles in cancer immunotherapy, prior to the present invention. For example, prior to the present invention, TAAs have been identified by analyzing ongoing immune responses in cancer patients, yet the immune systems of such patients are unable to regress their tumors. Moreover, most TAA-derived peptides, prior to those identified in the present invention, bind with low affinity, at best, to major histocompatibility (MHC) molecules, and therapeutic strategies have thus required the design of derivatives with better binding characteristics. In addition, most TAAs known prior to the present invention are expressed heterogeneously, limited to one or a few tumor types and to a fraction of patients with these types of tumors (Rosenberg, Immunity 10:281-287, 1999). Due to these facts, clinical studies have been limited, as strategies have been tested one malignancy at a time, and, in some cases (such as the idiotype in lymphoma), patient by patient (Hsu et al., Blood 89:3129-35, 1997). Finally, as has already been demonstrated, targeting a single tumor antigen can lead to immunoselection of antigen loss variants (Jager et al., Int. J. Cancer 71:142-147, 1997). Similar to chemotherapy, single agent strategies in immunotherapy may be of limited value.

In light of these limitations, a central hypothesis of the present invention is that targeting a set of homogenously expressed universal tumor antigens that contain T cell epitopes with high affinity to MHC, such that clinically sufficient anti-tumor T cell responses are elicited by use of such antigens, will facilitate the development of widely applicable immunotherapy, circumventing immunological escape mechanisms. The methods of the present invention allow accomplishment of these goals.

The invention thus provides methods of identifying and characterizing universal tumor associated antigens (TAAs). Such antigens: (1) are expressed by the vast majority of human cancers, (2) include peptide sequences that bind strongly to MHC molecules, (3) are processed by tumor cells such that antigen-derived peptides are available for binding to MHC molecules, and (4) are recognized by the T cell repertoire in an MHC-restricted fashion, permitting the expansion of cytotoxic T cells (CTL) bearing specific T cell receptors. The present invention allows the identification and characterization of such tumor antigens by:

1. using bioinformatics tools to facilitate the identification of universal tumor antigens containing T cell epitopes with high binding affinity;

2. establishing a time-resolved fluorometry-based assay to simultaneously measure MHC class I binding affinity and MHC/peptide complex stability for a large set of peptides; and 3. using a T cell screening system to facilitate the simultaneous evaluation of a large set of peptides as candidate immunogenic T cell epitopes.

Using these methods, we have identified the catalytic subunit of human telomerase (hTERT) as being a universal tumor associated antigen (TAA). Characterization of hTERT is described further below, after a description of our general methods.

Use of Bioinformatic Tools in Immunology

There is clearly a very significant increase in the use of computers, bioinformatics, and large public genetic databases in basic biology. Yet, there remains a tremendous need to link computational sciences to other fields of biology (Malakoff, Science 284:1742, 1999); in particular, applied biological sciences, including immunology. Tumor immunology is currently disconnected from the fast development of publicly available genetic information, in the form of databases on the Internet, such as the Cancer Genome Anatomy Project (CGAP) (Kuska, J. Natl. Cancer Inst. 88:1801-1803, 1996). This is rather surprising, since immunological technologies used to identify TAAs are still very demanding (Boon et al., Annual Review of Immunology 12:337-365, 1994; Sahin et al., Cum Opin. Immunol. 9:709-716, 1997), and therefore the use of 'dry-lab' technologies that reduce 'wet-lab' time in tumor immunology would greatly benefit the field. As was demonstrated for drug development, the increase in computational power and the use of computer sciences can greatly reduce the time spent for 'wet-lab' experimentation, thereby reducing effort and cost (Larvol et al., Nat. Biotechnol. 16(Suppl.):33-34, 1998). We have developed methods to link tumor immunology with publicly available genetic information on cancer, thus facilitating identification of universal TAAs (e.g., hTERT; see below) and, in particular, MHC-binding peptides of such universal TAAs.

T Cell Mediated Anti-Tumor Immunity

There is considerable evidence that human T cells can specifically lyse tumor cells (Rosenberg, Immunity 10:281-287, 1999). Most attention has been focused on $CD8^+$ CTL as the principle effector cells of antigen-specific anti-tumor immunity. Chief among the recent discoveries that have helped propel clinical efforts has been the characterization of tumor associated antigens (TAAs) (Boon et al., Annual Review of Immunology 12:337-365, 1994). Pioneering studies in the early 1990s demonstrated the existence of human TAAs using patients' CTLs that recognized peptides derived from these antigens (Van Pel et al., Immunological Reviews 145:229-250, 1995; Rosenberg, Immunol. Today 18:175-182, 1997). Although these studies primarily focused on melanoma, TAAs have been subsequently characterized in several other malignancies (Van Pel et al., Immunological Reviews 145:229-250, 1995; Rosenberg, Immunol. Today 18:175-182, 1997; Van den Eynde et al., Curr. Opin. Immunol. 9:684-693, 1997), raising the hypothesis that most, if not all, tumors express antigens that CTL can potentially attack. The demonstration that TAA-specific immune responses can lead to tumor regression has been borne out extensively in animal models (Rosenberg, Immunity 10:281-287, 1999). Although the identification of TAAs using patients' CTLs has revitalized the field of T cell immunotherapy, the methodology prior to the present invention is slow, very expensive, and labor-intensive. Moreover, the strategy relies on the generation of tumor-specific T cell clones in vitro, suggesting that only a restricted set of TAAs will be identified by this method. With these limitations in mind, Pfreundschuh and colleagues developed an alternative approach, SEREX (serological identification of antigens by recombinant expression cloning), to identify TAAs (Sahin et al., Curr. Opin. Immunol. 9:709-716, 1997). SEREX makes use of patients' antibody responses to tumor-derived genes and this strategy has accelerated the identification of TAAs significantly. Although several T cell-defined TAAs, such as the MAGE genes, have also been identified by SEREX, there is no information available about CTL epitopes for the vast majority of genes in the SEREX database, and, of course, such epitopes are required to activate a CTL response.

Although there is no doubt that the identification of numerous TAAs by CTL-based approaches or SEREX reflects the existence of an anti-tumor immune response, it remains to be determined if these antigens play a role as tumor regression antigens (Sarma et al., J. Exp. Med. 189:811-820, 1999). As is mentioned above, most T cell epitopes in TAAs identified by patient CTLs have been demonstrated to be of low MHC binding affinity and/or low MHC/peptide complex stability. Clinical vaccination trials have circumvented this obstacle by utilizing altered peptides with higher MHC binding affinity and higher MHC/peptide complex stability (Rosenberg et al., Nat. Med. 4:321-327, 1998). This quality distinguishes TAA-derived peptides from viral peptides that are almost exclusively of high binding affinity and high MHC/peptide complex stability (Feltkamp et al., Mol. Immunol. 31:1391-1401, 1994; Sate et al., J. Immunol. 153:5586-5592, 1994). The low binding affinity of TAA-derived peptides is likely to be one of the reasons why natural CTL responses against such peptides are not successful for tumor eradication. This is in agreement with the finding that large numbers of TAA-specific CTLs co-exist with metastatic tumors in melanoma patients (Romero et al., J. Exp. Med. 188:1641-1650, 1998). A recent study has even demonstrated that despite expansion, such CTLs were hyporesponsive, showing reduced cytotoxic and cytokine responses (Lee et al., Nat. Med. 5:677-685, 1999).

To overcome these limitations of currently known TAAs, we have developed methods to identify more universal TAAs, and, in particular, those containing T cell epitopes with high MHC binding affinity and high MHC/peptide complex stability. Such TAAs and MHC-binding peptides thereof can trigger sufficient CTL responses against a broad range of tumor types. Rather than analyzing tumor-derived T cell clones or tumor-specific antibodies derived from patients, an alternative strategy was used, in which TAA and their CTL epitopes are deduced from genes known to be selectively expressed in tumors. By combining bioinformatics to predict peptides that bind to HLA with high affinity, peptide binding analysis, and a powerful in vitro T cell expansion system, the catalytic subunit of telomerase (hTERT) was identified (see below). This TAA contains at least one peptide epitope that (1) binds to HLA-A*0201 with high affinity and high MHC/peptide complex stability, (2) is naturally processed and presented by HLA-A*0201 molecules on the cell surface of a panel of tumor cell lines and fresh tumor samples, (3) elicits peptide-specific HLA-restricted CTL responses, and (4) is recognized by such CTL on a wide variety of different tumor histologies. hTERT also contains at least one peptide epitope that (1) binds to HLA-A3, (2) can be used to generate HLA-A3 restricted, hTERT-specific CTL from a cancer patient, and (3) lyses tumor cells in an HLA-A3 restricted and hTERT-specific fashion (see below). The identification of such CTL epitopes in hTERT demonstrates the feasibility of this approach, and provides valuable tools for tumor immunotherapy. Also, it is desirable to identify universal tumor antigens in addition to hTERT to be able to target multiple TAAs, thereby circumventing immune escape mechanisms. The invention provides methods to accomplish this.

Deducing CTL Epitopes in Tumor Associated Antigens (TAAS): Making Use of Genomics and Proteomics for Tumor Immunology Current developments in genomics and proteomics suggest that numerous TAA candidate genes can be identified. The Human Genome Project (HGP), the Human Cancer Gene Anatomy Project (CGAP), the SEREX database, and other databases, including literature databases such as PubMed, provide an enormous set of data that can be analyzed to identify genes that fulfill the criteria of universal tumor antigens, as are described above. It is clear that entering the post-genomic era, none of the classical approaches to characterize TAA, including T cell cloning and testing of T cell clones against expression libraries (Boon et al., Annual Review of Immunology 12:337-365, 1994), is suitable for the analysis of the ever-growing databases to identify a set of universal tumor antigens.

To overcome the limitations of prior methods in determining CTL epitopes, advances in bioinformatics can be applied. First, database mining and integration can be used to identify of universal tumor antigen candidates, which are genes that are expressed at a much higher level in tumor cells than in normal cells. Then, computational methods are used to predict peptides derived from these proteins for high-affinity binding to MHC molecules. The requirements for peptides to bind to class I HLA molecules and to elicit CTL responses have been studied extensively (Rammensee et al., Annual Review of Immunology 11:213-244, 1993; Sidney et al., Immunology Today 17:261-266, 1996). The strength of $CD8^+$ CTL responses depends upon the binding affinity of the target peptide to MHC, the peptide-MHC complex stability, and the avidity of T cell receptor (TCR) binding for the peptide complex (Sette et al., J. Immunol. 153:5586-5592, 1994; van der Burg et al., J. Immunol. 156:3308-3314, 1996; Savage et al., Immunity 10:485-492, 1999; Gallimore et Eur. J. Immunol. 28:3301-3311, 1998). These factors directly influence the efficiency of peptide loading and the number of peptides expressed on the cell surface (Gallimore et al., Eur. J. Immunol. 28:3301-3311, 1998). The vast majority of viral-derived immunodominant peptides are of high binding affinity and/or peptide-HLA complex stability (Feltkamp et al., Mol. Immunol. 31:1391-1401, 1994; Sette et al., J. Immunol. 153:5586-5592, 1994). Since only a very small portion of peptides can bind to MHC molecules, rapid and accurate methods to identify them, such as those used in the present invention, can expedite the search for CTL epitopes by orders of magnitude.

A great deal of effort has been expended on the development of computational methods to identify peptides that bind strongly to various MHC alleles. It began with the work of Rammensee and colleagues, who identified motifs in peptide sequences that serve as signatures of the MHC molecules to which they bind (Rammensee et al., Immunogenetics 41:178-228, 1995). Motif-based methods have recently been applied to the identification of CTL epitopes deduced from proteinase 3 (Molldrem et al., Blood 88:2450-2457, 1996), MAGE-3 (Nijman et al., Eur. J. Immunol. 23:1215-1219, 1993), MUC-1 (Brossart et al., Blood 93:4309-4317, 1999), and telomerase (see below). Typically, only 20% of peptides that carry the motif bind to the respective MHC molecule. The inclusion of "secondary anchor" positions (Ruppert et al., Cell 74:929-937, 1993), the so-called extended motif, significantly improves the specificity of motif-based methods, but they are available only for HLA-A*0201 (Ruppert et al., Cell 74:929-937, 1993) and HLA-B*3501 (Schönbach et al., J. Immunol. 154:5951-5958, 1995). Many other statistically-based computational methods have been developed (for reviews, see, e.g., Hammer, Curr. Opin. Immunol. 7:263-269, 1995; Parker et al., Immunol. Res. 14:34-57, 1995), including the polynomial method (Gulukota et al., J. Mol. Biol. 267:1258-1267, 1997), methods based on neural nets (Gulukota et al., J. Mol. Biol. 267:1258-1167, 1997; Brusic et al., Bioinformatics 14:121-130, 1998; Brusic et al., Nucleic Acids Res. 26:368-371, 1998), a method that assigns a score for each amino acid at each position as determined experimentally via single residue substitutions (Hammer et al., J. Exp. Med. 180:2353-2358, 1994), and a method developed by Parker et al. based on a database of the half-lives of bound β2-microglobulin (β2m) in MHC-peptide complexes (Parker et al., J. Immunol. 152:163-175, 1994). The method developed by Parker et al. assumes that the dissociation of β2m is rate-limited by the dissociation of peptide, so that variation in the microglobulin half-life reflects variation in the peptide half-life. The variation is, in turn, assumed to reflect the variation in the binding affinity of the peptide. A weight matrix is then determined to best reflect the half-lives, assuming that the contribution of one peptide position does not depend on its neighboring positions. Weng and colleagues have recently developed a new statistical method (implemented as a computer program named LPpep; Weng et al., http://bioinformatics.bu.edu/peptides.html) to predict strong HLA-A*0201-binding peptides. It determines the contributions for each of the 20 amino acids at each of the positions of a peptide using a linear programming algorithm. When tested on a data set of over 1000 peptides having known binding affinities, LPpep has a higher sensitivity (>0.75) and specificity (>0.9) than four other available methods.

High Volume Analysis of Peptide Mhc Affinity and MHC/Peptide Complex Stability

The basic principles of peptide binding to MHC molecules have been well established in the field (Rammensee et al., Annual Review of Immunology 11:213-244, 1993; Rothbard et al., Annual Review of Immunology 9:527-565, 1991; Engelhard, Annual Review of Immunology 12:181-207, 1994; Madden, Annual Review of Immunology 13:587-622, 1995; Pamer et al., Annual Review of Immunology 16:323-358, 1998; Rock et al., Annual Review of Immunology 17:739-779, 1999), and numerous assay systems have been developed to analyze the binding of any given peptide to MHC molecules. Binding has been analyzed using intact TAP-deficient cells (Salter et al., EMBO J. 5:943-949, 1986; Schumacher et al., Cell 62:563-567, 1990) and by in vitro assays utilizing purified HLA molecules (Ruppert et al., Cell 74:929-937, 1993; Schumacher et al., Cell 62:563-567, 1990; Townsend et al., Cell 62:285-295, 1990). While most assay systems have focused on the maximal binding affinity, it has recently been suggested that the dissociation rate of MHC and peptide (also measured as MHC/peptide complex stability) may be a more important determinant for characterizing a peptide as a dominant T cell epitope (van der Burg et al., J. Immunol. 156:3308-3314, 1996; Busch et al., J. Immunol. 160:4441-4448, 1998; Kammer et al., J. Exp. Med. 190:169-176, 1999). While cell-based assays are generally analyzed by flow cytometry, the standard in vitro assays are based on competition for MHC binding between a radioactive reference peptide and increasing concentrations of a peptide under study. Both approaches are not ideal for high-throughput screening. Only recently, a fluoroimmunoassay employing Europium-streptavidin and time-resolved fluorometry has been described to analyze peptide binding to murine H-2kD molecules (Jensen et al., J. Immunol. Methods 215:71-80, 1998). We use this assay for high volume, routine analysis of peptide binding to MHC.

In Vitro Analysis of CTL Responses

The generation of antigen-specific T cells in vitro is a classical immunological technique. Antigen-specific T cells can be generated relatively easily if the peptides used to make such cells are: (1) immunodominant, (2) of viral or other non-self origin, (3) expressed at a reasonably high copy number on the cell surface (Porgador et al., Immunity 6:715-726, 1997), and (4) of high affinity for, and of low dissociation rate (high MHC/peptide complex stability) from, MHC, and if the T cell pool under study has been exposed to the antigen in vivo prior to ex vivo analysis (recall response). The frequency analysis of peptide-specific T cells by tetramer technology (see below) revealed a significantly higher frequency than earlier assays based on in vitro expansion had suggested. It is therefore apparent that only a fraction of specific CTLs are expanded in classical in vitro systems utilizing unstimulated peripheral blood mononuclear cells (PBMC) as antigen presenting cells (McMichael et al., J. Exp. Med. 187:1367-1371, 1998). To circumvent these pitfalls, in vivo systems utilizing transgenic mice carrying human HLA genes have been introduced (Man et al., International Immunology 7:597-605, 1995; Wentworth et al., International Immunology 8:651-659, 1996; Alexander et al., J. Immunol. 159:4753-4761, 1997). However, these systems are expensive and are not suitable for screening multiple peptide epitopes simultaneously. Making use of new findings in basic immunology, it is possible to further optimize currently available in vitro culture technology. The use of an APC instead of PBMC as stimulators is only one example.

We have developed a system that utilizes dendritic cells (DC) for primary activation and CD40-activated B cells (CD40-B) for re-stimulation, thereby mimicking the physiological sequence of events between T cells and APCs during an ongoing immune response (Schultze et al., J. Exp. Med. 89:1-12, 1999; Schultze et al., J. Clin. Invest. 100:2757-2765, 1997). This system has been successfully used for the identification of T cell epitopes derived from hTERT (see below) and the clonal immunoglobulin in B cell malignancies (see below). From a single blood draw, professional APCs, including DCs and CD40-activated B cells, are generated, and the remaining PBMCs are enriched for $CD8^+$ T cells. T cells are primarily stimulated with peptide-pulsed DC, and repeatedly stimulated with peptide-pulsed CD40-B cells. Peptide-specificity and HLA-restriction is analyzed after a total of 2-5 stimulations, depending on the antigen under study. This system is not only very powerful in amplifying rare T cells against TAA-derived peptides, but has several other advantages: (1) it is relatively cheap compared to transgenic mice, (2) a single blood draw is sufficient to generate all cellular components necessary, and (3) the use of professional APCs for restimulation is superior to PBMC.

Classically, the function of CTLs in vitro has been defined by cytotoxicity assays using radioactive chromium. Clearly, cytotoxicity analysis is an important component of the characterization of a novel TAA, since tumor cell lysis is the ultimate goal of any TAA-directed immunotherapeutic intervention. However, such assays are not suitable to determine the frequency of peptide-specific CTLs. In addition, the sensitivity of cytotoxicity assays to identify very small numbers of specific CTLs is insufficient. To detect very low numbers of specific CTLs and to determine their frequency, two new technologies, namely the tetramer technology (Altman et al., Science 274:94-96, 1996) and cytokine ELISPOT analysis (Herr et al., J. Immunol. Methods 203:141-152, 1997), have been developed and applied to tumor immunology. In particular, tetramers have been suggested as a tool to enrich CTL lines for peptide-specific CTL (Dunbar et al., Curr. Biol. 8:413-416, 1998; Yee et al., J. Immunol. 162:2227-2234, 1999; Valmori et al., Cancer Res. 59:2167-2173, 1999). Currently, the tetramer technology is still technically demanding and it is not possible to generate numerous tetramers in small quantities to screen peptide-specific CTL responses against a larger set of unknown peptides. For this purpose, cytokine ELISPOT is more suitable (Herr et al., J. Immunol. Methods 203:141-152, 1997).

As is noted above, technology used prior to the present invention to identify tumor antigens and peptides of these antigens that are recognized by T cells is slow, labor-intensive, and not suited for screening the large and still expanding number of potential target antigens available from HGP, CGRP, NCBI, SEREX, and other databases. To apply the vast information from Genomics and Proteomics to immunotherapy, it is necessary to develop high-throughput screening systems by combining bioinformatics tools predicting immunodominant peptides, systems to efficiently screen for peptide binding, and fast and reliable T cell response analysis to screen for many potential targets simultaneously. The screening system described herein makes use of the vast genetic information available in public databases, and applies this information to the identification of a set of novel universal tumor associated antigens as targets for immunotherapy of cancer. A set of universal tumor associated antigens identified in this manner can be used in widely applicable cancer immunotherapy (see below), preventing the induction of immune escape mechanisms.

This screening system is not restricted to cancer, but can also be applied to infectious diseases. For example, the genetic information of a virus stored in a database can be analyzed for potential T cell epitopes, and these peptides can then be systematically tested in the system described here, and used in therapeutic methods, such as those described below. Moreover, the cellular system described here can form the technical platform for monitoring the full dynamics of such complex immune responses as the one against cancer.

The principle of the overall approach of this invention has been established as exemplified by a universal tumor-associated antigen, hTERT, and a more restricted tumor-associated antigen, the clonal immunoglobulin of malignant B cells, which are each described further below. These data demonstrate that it is possible to identify tumor antigens by combining: (1) bioinformatics for peptide prediction, (2) peptide binding analysis, and (3) a powerful in vitro T cell screening system (Schultze et al., Journal of Clinical Investigation 100: 2757-2765, 1997). Moreover, using the SEREX database that we have already established, it is possible to identify truly tumor-related antigens by data mining publicly available databases.

Further details of the universal TAA identification and characterization methods are provided as below, followed by a description of how these methods were used to identify and characterize hTERT and the clonal immunoglobulin of malignant B cells.

Peptide-Prediction on Genes in Tumor-Related Databases: Peptide Prediction for MHC Class I Molecules Using the SEREX database (http://www-ludwig.unil.ch/SEREX/), we assessed whether available information can be used to determine candidate genes for the proposed analysis. In July, 1999 the database contained 548 gene entries. Of these sequences, full protein information was available for 245 genes (44.7%), containing approximately 140,000 9-mers and 10-mers. These 254 genes were then analyzed for peptides predicted to bind to HLA-A*0201 using the algorithm available on the NIH Website (Parker, http://bimas.dcrtnih.gov/molbio/hla_bind/). Ninety-seven genes (17.7% of all sequences in the database) were identified, with at least one peptide of predicted half-life>16 hours. BLAST analyses (Altschul et al., Nucleic Acids Research 25:3389-3402, 1997) confirmed uniqueness of the sequence. Since we want to target only genes that are cancer-related, we limited the number of genes by data mining for information in literature databases that supported that the gene of interest was cancer-related. Twenty-seven of these genes (4.93% of all genes in the SEREX database) were already found to be associated with cancer. A total of 49 peptides were identified from these genes were predicted to bind with high affinity to HLA-A*0201. Conservatively calculated, the identification of 49 prime candidate peptides out of 140,000 is a over 2000-fold reduction of 'wet-lab' screening effort for these genes.

LPpep: Further Development of Peptide-Prediction for MHC Class I Binding

A statistical method, LPpep (Weng et al., http://bioinformatics.bu.edu/peptides.html), has been developed to predict the binding affinity of a peptide to HLA-A2, given the peptide sequence. The binding affinities are represented as log (IC50) values, where the IC50 of a ligand is the concentration required to displace 50% of a reference ligand from a receptor. The IC50 is inversely proportional to the equilibrium binding constant over a wide range of conditions. Like most other statistical methods, LPpep assumes that the contribution of a given peptide side chain to binding depends only on its position in the sequence, and is independent of its neighbors. The residue contributions to log(IC50) were obtained using a linear programming algorithm such that the cumulated absolute error between calculated and measured log (IC50) values was minimal. A database of 536 peptides (9-mers) and 457 peptides (10-mers) with their associated 1050 values (measured by Sette and colleagues) with respect to HLA-A2 were used during the analysis.

The ultimate goal was to select peptides that can elicit CTL responses. Even though a peptide must first bind to an MHC molecule to elicit a T cell response, the correlation between binding and stimulation is not perfect. Sette and colleagues have shown that most of the peptides that can elicit CTL responses have 1050<500 nM, with smaller IC50 correlated with higher immunogenicity (Ruppert et al., Cell 74:929-937, 1993). We therefore confined testing of our algorithm to the most relevant immunological range, testing performance by determining sensitivity and specificity for the selection of: (1) strong binders (IC50 50 nM), and (2) strong and intermediate binders (IC50 500 nM). Specifically, using 50 nM or 500 nM as cutoff, we calculated the sensitivities and specificities of LPpep and four other methods on the same data set: EM—the extended motif method (Ruppert et al., Cell 74:929-937, 1993), PAR—the method by Parker et al. (J. Immunol. 152: 163-175, 1994), PM—the polynomial method (Gulukota et al., J. Mol. Biol. 267:1258-1267, 1997), and NN—a neural network method (Gulukota et al., J. Mol. Biol. 267:1258-1267, 1997). For EM, PAR, and PM, we simply adopted the parameters developed by other groups and tested them on our database. For NN and LPpep, we developed the parameters on one part of the database and tested them on the other part using a jackknife technique.

The sensitivities and specificities of all five methods were determined for 9-mers and 10-mers. The coefficients for 10-mers are not available for PM, therefore, only four methods were tested for 10 mers. EM stands out as the method with the highest sensitivity and the lowest specificity. PM and PAR are at the other extreme: they have sensitivities close to zero and specificities close to one. LPpep and NN are the two best performers, with LPpep better than NN in terms of both sensitivities and specificities, for both cutoffs, and for both 9-mers and 10-mers.

When the 50 nM cutoff was used, LPpep has sensitivities of 0.58 (for 9-mers) and 0.71 (for 10-mers) and a specificity of 0.97. Although the sensitivities are not as high as those of EM, they are higher than all other methods. When the 500 nM cutoff was used, LPpep achieves the highest sensitivities among all methods (0.78 for 9-mers and 0.76 for 10-mers), while still maintaining competitively high specificities (0.89 for 9-mers and 0.92 for 10-mers). More interestingly, LPpep and NN seem to pick out somewhat different populations of binders. If we combine these two methods with a logical OR, i.e., a peptide is predicted to be a binder if it is predicted to be a binder by either LPpep, NN, or both, the sensitivities are substantially improved and the specificities are still high. The average absolute errors made by the three methods (PM, PAR, and LPpep) that predict log (IC50) have been compared, and LPpep has been found to have the smallest errors.

Binding of Peptides to HLA Molecules and Stability in Complexes with Peptides: Peptide-Binding to HLA-A*0201 Molecules Using TAP-Deficient T2 Cells To measure peptide binding of peptides to MHC class I molecules, as well as their stability in complexes with peptides, we employed a cellular assay using TAP-deficient T2 cells (see below). Briefly, T2 cells were incubated with peptide in serum-free medium for up to 18 hours, harvested, and subsequently stained with FITC-labeled anti-HLA-A2 mAb BB7.2 (maximum peptide binding). Increase in fluorescence intensity was determined as a function of peptide binding. For analysis of MHC/peptide complex stability, T2 cells were cultured for an additional 2, 4, 6, and 24 hours, and subsequently analyzed for HLA-A2 expression by flow cytometry. A MAGE-3-derived peptide that induced CTL responses in the majority of all normal donors demonstrated high binding affinity and high MHC/peptide complex stability. Our data support the concept that MHC/peptide complex stability may be a more important factor than binding affinity for the likelihood to generate peptide-specific CTL responses.

A Cell-Lysate Based ELISA to Determine Peptide-Binding to HLA-A*0201

Microtiter plate based non-radioactive assays are best suited to analyze a greater set of peptides simultaneously for MHC binding. Such an assay was adapted for the analysis of peptide-MHC binding and MHC/peptide complex stability. In addition, cellular MHC was used as a source of MHC molecules, since this circumvented the need for purification of multiple different MHC molecules. We have developed an ELISA that measures MHC/peptide complexes in cell lysates from T2 cells pre-incubated with peptides. MHC/peptide complexes were detected by a conformation specific anti-HLA-A2 mAb (BB7.2) that was coated onto ELISA plates. As capture antibody of this sandwich-ELISA, we used anti-132 microglobulin-HRP conjugates (see below). We have shown that it is possible to quantify the number of MHC/peptide complexes after addition of exogenous peptide. At dilutions of up to 1:16, cell lysates derived from T2 cells pulsed with either hTERT I540 or HTLV-tax demonstrated a 2-4 fold increase over background. These data are highly comparable with results obtained in classical T2 binding assays. This assay forms the platform for MHC binding and MHC/peptide complex stability assays described below.

Peptide-Binding to Other HLA Class I Molecules Using HLA-Transfected T2 Cells

To extend the use of this assay to other HLA-alleles, HLA-A*0301-transfected T2 cells were evaluated in binding assays using peptides well known to bind to HLA-A3, and the number of such complexes were quantified. Furthermore, cDNAs encoding for HLA-A*0101, A*2402 have been cloned from PBMC serotyped for HLA, and subcloned into retroviral vectors to be used in an assay to quantify the complexes.

Analysis of T Cell Responses In Vitro

Since radioactive chromium-release assays are not suitable for screening numerous CTL lines simultaneously, we have adapted several other techniques that are suitable as read out systems for T cell screening system. Some of the currently state-of-the-art assays include T cell analysis assays, including non-radioactive cytotoxicity assays, cytokine ELISPOT analysis, and tetramers.

Non-Radioactive Cytotoxicity Assay

Utilizing time-resolved fluorometry and Europium as fluorochrome, it has been demonstrated that chromium-release assays can be replaced by this non-radioactive assay (Bohlen et al., Journal of Immunological Methods 173:55-62, 1994). Briefly, instead of radioactively labeling target cells with chromium, the cells are labeled with a Europium ligand that is released similarly to chromium if the cells are lysed. Chelation of Europium by its ligand leads to light emission that can be detected by time-resolved fluorometry using a fluorometer.

We have evaluated this assay using a CTL line generated against the HLA-A3 restricted influenza A derived peptide NP265. Cytotoxicity determined by Europium in a 2 hour assay was found to be even superior to the standard 4 hour chromium release assay.

ELISPOT Assay

A better estimate of the frequency of functional antigen-specific T cells was established by the ELISPOT technique (Herr et al., J. Immunol. Methods 203:141-152, 1997). This assay analyses the peptide-specific CTL response against the influenza A matrix protein derived peptide GILGFVFTL in peripheral blood of normal HLA-A*0201 donors. Briefly, 96-well plates lined with polyvinylidene fluoride (PVDF) membranes were pre-coated with anti-IFN-γ mAbs to capture secreted cytokine. T cells and APC were cultured onto these plates in the presence of the peptide under study. The APCs took up and presented peptide to antigen specific T cells, inducing them to secrete IFN-γ. After 24 hours, plates were washed, incubated with matched biotinylated anti-IFN-γ mAbs, and an alkaline phosphatase colorimetric reaction was induced. Resulting "spots" represented areas of T cell IFN-γ secretion, while control wells (media alone or a control peptides derived from HTLV-1 (tax)) did not induce measurable "spots." An automated ELISPOT reader (ImmunoSpot, RTI, Inc.) was used for automated analysis.

MHC/Peptide Tetrameric Complexes

The tetramer technology has been demonstrated to be the most useful to directly enumerate peptide-specific CTL or to enrich peptide-specific CTL in ex vivo culture systems (Lee et al., Nat. Med. 5:677-685, 1999: Savage et al., Immunity 10:485-492, 1999; Altman et al., Science 274:94-96, 1996; Yee et al., J. Immunol. 162:2227-2234, 1999; Valmori et al., Cancer Res. 59:2167-2173, 1999). We have generated tetramers composed of recombinant HLA-A*0201, β2m, and a peptide derived from the HPV protein E7 or the HTLV-1 tax protein. Using these reagents, we have been able to detect a small fraction of E7-peptide specific T cells in a CTL line generated from peripheral blood T cells of a normal donor by primary in vitro stimulation using peptide-pulsed DC followed by two restimulations using peptide-pulsed CD40-B cells. We have used tetramers to demonstrate the expansion of hTERT-specific CTL in our I cell expansion system. These data further confirm the peptide-specificity as functionally determined by chromium release assays. These methods are described in further detail, as follows.

The overall aim of this invention is to develop a system that facilitates the identification of novel universal tumor antigens containing T cell epitopes of high binding affinity to MHC. By introducing bioinformatics tools, the enormous time that would be necessary to determine such genes by classical 'wet-lab' technology can be considerably shortened. Mining available public databases (e.g., HGP, SEREX, CGAP, and PubMed) candidate universal TAA genes are identified and screened for HLA-binding motifs using predictive computational algorithms. Peptide-prediction is followed by HLA-binding assays. To develop an HLA-binding assay with high-throughput capacity, several assay systems were compared using an array of peptides available in our laboratory. Using a set of peptides from TAA currently under study in the laboratory, our CTL screening system was further developed and optimized. As read-out systems for peptide-specific T cells generated in our T cell system, state-of-the-art T cell analysis tools were evaluated, including non-radioactive cytotoxicity assays, ELISPOT, and tetramer technology. To enable automation in the future, all assays involved in this system were developed in micro-titer plate format.

Bioinformatics Tools to Facilitate the Identification of Universal Tumor Antigens Containing T Cell Epitopes with High Binding Affinity: Identifying Tumor-Associated Antigens by Data Mining To identify tumor-associated antigens, databases including, but not limited to, the following can be mined: (1) CGAP (Cancer Genome Anatomy Project; http://www.ncbi.nlm.nih.gov/ncicgap/), which includes genes that are expressed only in tumors and that can be identified by comparison of the expression profiles of malignant tissue vs. normal tissue; (2) SEREX (http://www-ludwig_unil.ch/SEREX/), which is a repository of expressed genes against which antibodies in the serum, from cancer patients, show reactivity; (3) HGP at NCBI (http://www.ncbi.nlm.nih.gov/genome/guide/), which includes all available human genes and ESTs and their expression information; and (4) PubMed at NCBI (http://www.ncbi.nlm.nih.gov/PubMed/), which is a database of published articles. Computational algorithms are used to search CGAP, SEREX, and HGP regularly for tumor-related genes and/or gene variants, as well as their expression levels both in tumor cells and normal cells. A web-based in-house database (called TAADB) is used to store search results. Sometimes, newly discovered TAAs as reported in PubMed articles are not in CGAP, SEREX, or HGP. The appropriate information can be manually extracted from the articles and store it in TAADB. TAADB integrates information on the same gene from all databases, with cross-references to the appropriate source. All genes in TAADB can be ranked according to how exclusively they are expressed in tumor cells compared to normal cells, and a higher "exclusiveness score" indicates a better candidate for a universal tumor antigen.

Identifying TAA Peptides that Bind to Major Class I MHC Molecules

We focused on the most common alleles (Gulukota et al., Genet. Anal. 13:81-86, 1996)-A2, A1, A3, and A24. Moreover, HLA-A3 shares peptide specificities with A11, A31, A33, and A68, the so-called "HLA-A3 supertype" (Sidney et al., Immunology Today 17:261-266, 1996). The above four alleles combined can cover over 90% of the human population. Candidate TAAs identified above and stored in TAADB were subjected to currently available computational algorithms to predict peptides that can bind strongly to these four MHC alleles.

Peptide prediction methods, including, but not limited to, the following, can be used. The method developed by Parker et al. (J. Immunol. 152:163-175, 1994) is available via WWW (http://bimas.dcrt.nih.gov/molbio/hla_bind). This method is available for all four major HLA alleles, although we suspect the method to be the most accurate for A2, since more experimental data are available for peptides binding to this allele. In our previous analysis (hTERT and Ig of malignant B cells, see below), we have used a cellular binding assay to test peptides predicted by the Parker method and observed a statistically significant correlation between the prediction and experiment. Specifically, we found this method to have very high specificity, however relatively low sensitivity. We have established a local version of the Parker algorithm so that all TAA candidates in TAADB can be examined in minutes.

The second method is the LPpep method developed by Weng and her colleagues, currently available on the web (http://bioinformatics.bu.edu/peptides.html). This method has been shown by Weng and colleagues to perform better than the Parker method (Parker et al., J. Immunol. 152:163-175, 1994) on a set of 1000 peptides whose IC50s have been measured by Sette and colleagues. One obvious advantage of this method over the Parker method is its higher sensitivity and the other advantage being that we can further develop this method by incorporating new binding data generated using the methods described herein (see below). LPpep is currently available only for A2 and we can extend it for the other three common alleles A1, A3, and A24 (see below).

The third method is the neural network algorithm (NN) (Gulukota et al., J. Mol. Biol. 267:1258-1267, 1997). One advantage of NN over the Parker method and LPpep is that NN does not assume that neighboring peptide positions contribute independently to the binding. We discovered that the combination of NN and LPpep could result in some overall improvement. We can further develop this algorithm with new binding data generated in this project. NN is currently available for A2 and can be extended to the other three alleles (see below).

All of the above-described 3 methods were applied to the candidate TAAs identified, as is described above. There is a tradeoff between the number of peptides we wanted to test experimentally and the false negative rate we were willing to tolerate. For TAAs with high exclusiveness scores, we adjusted computational methods towards high sensitivity and sacrificed some specificity. Predicted peptides were examined by sequence alignment methods (such as BLAST (Altschul et al., Nucleic Acids Research 25:3389-3402, 1997)) to ensure that they were not related to any genes expressed in normal tissue. Peptides from multiple TAAs received high priority. Predicted peptides for all TAAs were also stored in TAADB with cross-references to the corresponding TAA. The most promising peptides were examined for MHC binding and CTL responses, as is described below. Finally, of course, other similar methods can be used to identify TAAs.

As is noted above, LPpep and NN can be expanded to the other 3 major HLA alleles: A1, A3, and A24. Sette and colleagues have measured the IC50s for a few hundred peptides binding to these 3 alleles (see, e.g., Kubo et al., Journal of Immunology 152:3913-3924, 1994) and this information can be used to develop residue contributions to the binding in LPpep and to train the neural network in NN. Also, two databases are publicly available that include peptide sequences known to bind MHC molecules: SYFPEITHI (Rammensee et al., "SYFPEITHI: An Internet Database for MHC Ligands and Peptide Motifs") and MHCPEP (Brusic et al., Nucleic Acids Res. 26:368-371, 1998). However, quantitative information is not available on binding affinities, and therefore they can only be used to develop NN. Our group has accumulated data from >60 peptides that have been analyzed for binding affinity, MHC/peptide complex stability, and immunogenicity using cellular assays. This pool of peptides is continuously increasing with a predicted set of 50-100 new peptides per year. The influx of binding data generated in this project can be used to further modify LPpep and NN, allowing us to restrict cellular analysis to those peptides that are most likely to be recognized by T cells. LPpep can be further modified by relaxing the assumption that neighboring peptide positions contribute independently to the binding. We have explicitly incorporated a set of contributions corresponding to combinations of amino acid types at neighboring positions. Our results show that the performance of LPpep can be changed by considering pairwise correlations between positions 1 and 3, 3 and 4, and 5 and 6.

Algorithms for Prediction of MHC/Peptide Complex Stability and Immunogenicity

A number of groups (van der Burg et al., J. Immunol. 156:3308-3314, 1996; Savage et al., Immunity 10:485-492, 1999; Gallimore et al., J. Exp. Med. 187:1647-1657, 1998) have shown that dissociation rate is a better predictor for immunodominance than binding affinity. Our results also support such finding. Currently, LPpep and NN are developed based on IC50s, which are very good estimates of equilibrium binding constants. Since using the methods described herein, we have accumulated binding affinity and dissociation rate measurements for up to 500 new peptides, and we can establish LPpep and NN to predict dissociation rates. Among peptides with similar binding affinities, the ones with slower dissociation rates are obviously better choices for CTL activation.

Development of Algorithms for Prediction of Immunogenicity

Moreover, according to the present invention, we have developed computational algorithms to predict the immunogenicity. This appears to be much more difficult than predicting binding affinities and dissociation rates, since numerous other variables account for immunogenicity including for example peptide processing, T cell repertoire, and co-stimulatory molecules. However, we believe that there are common characteristics for immunogenic peptides. For example, earlier studies indicated correlations between immunogenicity and periodicity in hydrophobic residues (DeLisi et al., Proc. Natl. Acad. Sci. USA 82:7048-7052, 1985; Cornette et al., Proc. Natl. Acad. Sci. USA 92:8368-8372, 1995; de Groot et al., Proteins 29:240-251, 1997). Algorithms such as neural network and hidden Markov model are ideal for recognizing subtle patterns. We have applied them to the immunogenicity information for the peptides that we have generated, as well as over 100 T cell epitopes in the "SYFPEITHI" database (Rammensee et al., "SYFPEITHI: An Internet Database for MHC Ligands and Peptide Motifs").

Establishing a Time-Resolved Fluorometry-Based Assay to Simultaneously Measure Mhc Class I Binding Affinity and MHC/Peptide Complex Stability of a Large Set of Peptides We describe here a: (1) time-resolved fluorometry-based, (2) micro-titer plate based, (3) relatively inexpensive, (4) but highly sensitive and specific, assay that facilitates the analysis of numerous peptides for MHC binding affinity and MHC/peptide complex stability. As has been shown for murine MHC class I and II molecules (Jensen et al., J. Immunol. Methods 215:71-80, 1998; Tompkins et al., J. Immunol. Methods 163:209-216, 1993), binding analysis based on time-resolved fluorometry using Europium as fluorochrome fulfills these criteria. Our assay system has allowed high throughput screening of MHC binding affinity and MHC/peptide complex stability. The assay system is characterized by using a panel of peptides already established and characterized in our laboratory. These peptides (n=60) are restricted to HLA-A2 and -A3 and were derived from hTERT, the clonal immunoglobulin of malignant B cells, MAGE-3, Influenza A, or HIV proteins. A panel of new peptides identified above can then be used in the system. We began with peptides identified from the SEREX database (n=49), followed by universal tumor antigens identified by data mining.

T2 Cellular Binding Assay as Reference Assay

The classical T2 cellular binding assay was used as a reference assay to compare previously generated data with the new assay systems. Briefly, T2 cells were incubated with peptide in the presence of $\beta 2m$ in serum free medium for 12-18 hours. T2 cells were subsequently washed and stained with the BB7.2 mAb directly conjugated to FITC to determine binding affinity. Binding was determined by the relative shift of the mean fluorescence intensity (MFI) described as fluorescence index FI={MFI(T2 cells plus peptide)/MFI(T2 cells without peptide)}−1. To measure MHC/peptide complex stability, T2 cells were washed and kept in serum free medium until staining with BB7.2 mAb. The analysis was performed 0, 2, 4, 6, and 24 hours after the removal of exogenous peptide. The dissociation rate (t(MFImax/2)) is described as the time with half-maximal MFI (MFI(t)/2).

Generation of T2 Assays Analyzing Other HLA-Alleles

To obtain broad population coverage, the T2-based assays were extended by transfecting additional HLA-types into these cells. Complementary DNAs encoding HLA-A*0101, A*2402 have been cloned into retroviral vectors and were used to transfect T2 cells. These HLA-types together cover greater 90% of the whole population. A retroviral vector, pMXpuro, harboring either of the HLA-A cDNAs was transfected into an amphotropic packaging cell line, 293GPG, by lipofection. After 3 days, the culture supernatant was harvested, passed through 0.45 μm filters, and then used as a replication-defective retrovirus stock. For infection, T2 cells were cultured with the retrovirus for 8-12 hours in the presence of 8 μg/ml of polybrene, and then fresh RPMI-1640 medium was supplemented with 10% FCS. Forty-eight hours after infection, 3 μg/ml of puromycin was added, and drug-resistant cell lines were selected and subcloned by FACS. The different T2-transfectants were standardized by the classical T2 assay procedure using HIV-derived peptides known to bind with high binding affinity to these HLA-types.

Direct Detection of MHC/Peptide Complexes by ELISA

An ELISA-based assay using T2 cell-derived cell lysates as source of HLA-A2 molecules was used to measure peptide/MHC affinity and MHC/peptide complex stability. This assay relies on the ability of exogenous peptide to stabilize empty HLA class I molecules in vitro (Schumacher et al., Cell 62:563-567, 1990). T2 cells were incubated in microtiter plates with 10 μg/ml specific or irrelevant peptide for 18 hours at 37° C. Cells were lysed at 4° C. and lysates subsequently warmed to 37° C. (1 hour) for further enrichment of correctly folded MHC/peptide complexes. Cell lysates were subsequently transferred to ELISA plates coated with BB7.2 mAb, an antibody that only recognizes HLA-A*0201 complexed with peptide. As a secondary reagent, anti-β2m-HRP conjugates were used. In this case, TMB was used as substrate for HRP and the reaction stopped with 1N HCL. Alternatively, a biotinylated anti-β2m mAb can be used as capture antibody. In this case, Europium-streptavidin can be used to detect MHC/peptide complexes on a time-resolved fluorometer (Wallac Victor2 multi-label reader). This read-out is more sensitive and with a higher signal-to-noise ratio (Jensen et al., J. Immunol. Methods 215:71-80, 1998).

T2-A3 cells can be used to demonstrate the applicability of this assay for other HLA-alleles. The GAP.A3 mAb is specific for peptide-complexed HLA-A3 and does not bind endogenous T2 HLA alleles -A2 or -B5. To determine MHC/peptide complex stability (MBAt=0/2), cell lysates are incubated at 37° C. in the absence of exogenous peptide for 2, 4, and 6 hours before the ELISA is performed.

Competition Assay to Detect MHC/Peptide Complexes by ELISA

To date, most data used for the generation of peptide-prediction algorithms have been generated with competition assays using a radioactive reference peptide and increasing concentrations of the peptide of interest (Ruppert et al., Cell 74:929-937, 1993). We have detected discrepancies between cellular T2 assays and published data based on competition assays. To be able to compare directly these assays and to provide most accurate data for the optimization of our peptide prediction algorithms, we used a non-radioactive competition assay and compared this assay with our cellular T2 assay and the direct binding assay. We used T2 cell-derived MHC and a biotinylated peptide derived from the Influenza A matrix protein (FLPSDCFPSV; SEQ ID NO: 73) as a reference peptide, which was already being used as reference peptide in a fluorochrome-based assay (Kammer et al., J. Exp. Med. 190:169-176, 1999). T2 cells were incubated in microtiter plates with 10 μg/ml biotinylated reference peptide and increasing concentrations of peptide under study for 20 hours at 37° C. Cell lysates were prepared as is described above and loaded onto ELISA plates coated with HLA-A2-specific mAb BB7.2. Europium-streptavidin was used to detect MHC/reference peptide complexes. A maximum fluorescence (MF) was reached with biotinylated reference peptide without competitor peptide and set to 0% inhibition. The IC50 was determined as half-maximum fluorescence (MF/2=IC50). Conditions without reference peptide were set to 100% inhibition. This allowed calculation of percentage of binding inhibition using the formula: {1−(MF competitor peptide−MF no peptide)/(MF reference peptide−MF no peptide)}×100%. Moreover, T2-A3 cells were tested with the biotinylated influenza A nuclear protein-derived peptide NP265 as reference peptide.

The Use of CD40-Activated B Cells for Peptide-Binding Analysis

Since the use of T2 cells is restricted to the HLA alleles expressed on these cells, the use of other APCs is advantageous. The use of primary APC in MHC binding assays allowed us to study basically any HLA type for its binding profile. Indeed, MHC binding assays have been described for EBV-LCL (Kammer et al., J. Exp. Med. 190:169-176, 1999). Therefore, we used CD40-B cells, since these cells can be generated more easily than EBV-LCL. The use of autologous CD40-B cells facilitates the analysis of any given peptide on any HLA-type, as long as conformation-specific mAbs for the HLA-type under study are available. Moreover, the use of primary APC allowed us to determine if differences in binding affinity between individual donors existed. To prepare APCs for MHC binding assays it was necessary to empty MHC class I molecules ("stripping"). HLA molecules were "stripped" of peptides by mild acid treatment for 90 seconds using ice-cold citric acid-Na2HPO4 buffer. Immediately thereafter, the eluted cells were buffered with cold IMDM, washed with IMDM, and resuspended at 5×10$^5$ cells in IMDM with 1 μg/ml β2m. A competition assay was performed with biotinylated reference peptides. The biotinylated peptide (150 nM) was incubated in the presence of different concentrations of the peptide of interest in 96-well V-bottom plates. 100 μl of mild acid-treated CD40-B cells were added to these wells. The mixture was incubated for 24 hours at 37° C. in the presence of Brefeldin A to prevent binding of endogenously processed peptides and washed twice thereafter with PBS. We compared flow cytometry of extracellular HLA-A2 molecules (following the procedure described under above) with ELISA-based time-resolved fluorometry (following the procedure described above).

Automation of MHC Binding Assays

The methods described herein can employ microtiter plate-based peptide-binding assays that can be automated using robotics. To facilitate such methods, we focus on the use of: (1) microtiter plates, (2) small volumes, and (3) fluorometric read-out systems (Jensen et al., J. Immunol. Methods 215:71-80, 1998). Using 384-well plates, it is possible to significantly reduce volume, reagents (and therefore cost/test), and to perform competition assays (6 conditions, duplicates) for more than 30 peptides on a single plate.

A T Cell Screening System to Facilitate the Simultaneous Evaluation of a Large Set of Peptides as Candidate Immunogenic T Cell Epitopes The following methods were used to, e.g., shorten necessary culture time (and therefore, cost and effort) by using more sensitive and specific readout systems and by establishing less labor-intensive culture conditions. This includes the use of micro-titer plates to screen for more peptides simultaneously. We have used these methods on a smaller set of peptides (n<100). It is possible to fully screen up to 50 peptides for peptide-specific CTL L using PBMC from a single leukopheresis.

Generation of Antigen Presenting Cells

We have developed a system that is based on the use of immature DC for primary stimulation and CD40-B cells for restimulation (Schultze et al., Journal of Clinical Investigation 100:2757-2765, 1997). This system was optimized by using assays to monitor efficiency of peptide pulsing on primary APC.

DC were generated from PBMC-derived monocytes. Monocyte-enriched fractions from PBMC were obtained after sheep red blood cell rosetting. This cell fraction was cultured for 6-8 days in the presence of IL-4 (1000 IU/ml) and GM-CSF (50 ng/ml) in IMDM supplemented with human serum or plasma, insulin, glutamine, and gentamicin. Further optimization was carried out by testing a combination of CD40L and IFN-$\gamma$.

CD40-activated B cells were generated as previously published (Schultze et al., Journal of Clinical Investigation 100: 2757-2765, 1997). Briefly, CD40-activated B cells were generated from unfractionated PBMC by culture on tCD40L cells in the presence of IL-4 (100 IU/ml) and CsA ($5.5 \times 10^{-7}$ M). Soluble CD40L was tested as a substitute for the transfectants. The use of soluble CD40L required depletion of adherent cells, since this cell population seemed to prevent the outgrowth of B cells from PBMC when stimulated with sCD40L, IL-4, and CsA.

Monitoring Peptide-Pulsing on Primary APC

Although peptide pulsing has been studied in great detail for TAP-deficient cell lines, there was little known about the biology of peptide-pulsing onto primary APC. To determine the best conditions for this procedure, biotinylated or fluorescence conjugates of the influenza peptide and a peptide from hTERT was synthesized. Using these reagents, we determined maximum MHC binding of peptide and their MHC/peptide complex stability by varying: (1) the time of peptide-pulsing, (2) the medium for peptide-pulsing, (3) the concentration of exogenous $\beta$2m, (4) the temperature during peptide-pulsing, (5) the pH during peptide-pulsing, (6) the concentration of protease-inhibitors, and (7) the concentration of reagents blocking intracellular protein transport (e.g., Brefeldin A). These experiments were performed with DC and CD40-B cells.

CTL Lines and Their Analysis

As exemplified for hTERT and Ig see below, peptide-specific CTL responses were evaluated after 4-5 in vitro stimulations by chromium release assay. Moreover, the currently employed system is limited to testing of 6-10 peptides per experiment and the format of the assay is not suitable for screening larger numbers of peptides simultaneously. This system functions as the standard for comparison of a micro titer plate based system and the use of other readouts including ELISPOT and tetramers. Especially ELISPOT and tetramer analysis were tested for their suitability to reduce necessary culture time to identify peptide-specific T cell responses in this in vitro system.

We analyzed CU lines by ELISPOT to determine the earliest time point allowing identification of peptide-specific T cells. The analysis was validated by cytotoxicity analysis. We expected the sensitivity of ELISPOT analysis to be higher than that of tetramers. Moreover, this assay is more suitable as readout of a screening system. Moreover, we determined whether tetramers can be used to shorten further the time of T cell expansion to assess peptide-specific CTL responses. For these studies, we focused on a small set of peptides, including the HIV gag-derived peptide SLYNTVATL, the Inf A matrix derived peptide GILGFVFTL, and the MAGE-3 derived peptide FLWGPRALV.

Non-Radioactive Cytotoxicity Assay

We substituted chromium release assays entirely by a nonradioactive Europium release assay using a Victor2 multilabel counter (Wallac). Two major issues were addressed. First, we established optimal conditions for all potential target cells of our tumor cell panel. In particular, different signal-to-noise ratios may be present for different sources of target cells, similar to chromium release assays. Therefore, signal-to-noise ratios for all available tumor cell lines were determined and a protocol established that covers the spectrum of all the different target cell lines. Second, we tested the value of this assay as a binary readout for our micro-titer plate bases peptide screening assay (see above). Briefly, target cells were incubated for 20-30 minutes with 10 µM BATDA ligand (which forms a fluorescent chelate with Europium; Wallac, Gaithersburg, Md.) in culture medium at room temperature. Cells were washed five times in culture medium. Labeling efficiency was tested before cells were subsequently cryopreserved until use as targets in cytotoxicity assays. The availability of a stock of cryopreserved BATDA-labeled tumor cells and CD40-B cells further decreases: (1) variability between different cytotoxicity assays, (2) cost, and (3) labor, and allows higher throughput of screening for cytotoxicity. After cryopreservation, cells were washed and resuspended in serum-free (SF) medium (Iscove's modified Dulbecco's medium (IMDM) supplemented with 5 mg/ml bovine serum albumin (BSA; Sigma), 2 mM L-glutamine, 1.25 mM sulfinpyrazone (Sigma), and 1% penicillin/streptomycin). Where indicated, peptides were pulsed with $\beta$2m in SF medium for 60-90 minutes at 37° C. Cells were washed twice in SF CTL medium, resuspended in CTL medium (5% fetal calf serum), and combined with the CTL in round bottom microliter plates. Plates were gently centrifuged at 100×g for 2 minutes and then incubated at 37° C. for 2 hours. Finally, plates were centrifuged at 300×g, and 10 µl/well was transferred to 100 µl of 0.3 M acetic acid, 60 mM sodium acetate, 7.5 µg/ml Europium (Aldrich, Milwaukee, Wis.). After incubation for 15 minutes at room temperature the plate was read on a Wallac Victor2 multi-label counter. The percentage of specific lysis was calculated with the following equation: 100× ((experimental−blank)−(spontaneous−blank))/((maximum−blank)−(spontaneous−blank)).

ELISPOT Assay

A recently established ELISPOT assay for the detection of influenza-specific IFN-$\gamma$ producing T cell in peripheral blood was adapted to analyze peptide-specific T cells in our T cell screening system. In particular, we tested the utility of autologous peptide-pulsed CD40-B cells as a standardized source of APC to be used in ELISPOT analysis. The ELISPOT assay for IFN-$\gamma$ was performed on Millipore 96-well plates with polyvinylidene fluoride (PVDF) membranes. Plates were prepared by overnight incubation with cytokine capture antibody at 4° C. Plates were then washed 6 times with PBS/1% (v/v) fetal calf serum. T cells and APC were plated in the presence of peptide at the appropriate concentration and placed overnight at 37° C. Plates were washed with PBS/0.05% (v/v) Tween to carefully remove all cells and debris before incubation with a matched biotinylated anti-IFN-γ mAb. Plates were then washed in PBS/0.05% (v/v) Tween, followed by incubation with streptavidin alkaline phosphatase in PBS. Spots corresponding to areas of secreted cytokine were visualized by incubation with 5-bromo-4-chloro-3-indolyl phosphate and nitroblue tetrazolium. Spots were quantified using an automated ELISPOT reader (ImmunoSpot™ from RTI, Inc.), and graphical and numerical data was stored in the TAADB database (see above).

MHC/Peptide Tetramers

Preliminary data suggest that between 0.5-4% of peptide-specific CTL are generated in our T cell screening system. With the use of tetramers we addressed the following questions: (1) At which time point during T cell expansion can we detect tetramer-positive cells (given a detection limit of 0.1%)? (2) Can we identify more favorable culture conditions for the expansion of peptide-specific CTL by monitoring the culture with tetramer? (3) What is the impact of different concentrations and timing of IL-2 on the expansion of tetramer-reactive T cells? (4) Can we expand tetramer-positive cells generated in our system after flow assisted cell sorting and what are the best antigen-independent culture conditions to expand these CTL?

For flow cytometric analysis of T cell populations, approximately 0.5 μg of tetramer was added to T cells for 15 minutes at room temperature in PBS/3% FCS. The cells were washed twice with cold PBS/1% FCS and once with cold PBS, and then analyzed by flow cytometry. We primarily studied HLA-A2 tetramers, however, tetramers including other HLA-alleles can be studied as well.

Development of a Micro Titer Plate-Based Assay System

To screen more peptides simultaneously, an assay based on 96-well plates was used. CD8$^+$ T cells were isolated from PBMC and primarily stimulated with autologous peptide-pulsed DC (ratio T:DC=20:1), followed by stimulation with peptide-pulsed CD40-B cells (ratio T:CD40-B=4-10:1). While IL-7 was added during every re-stimulation, IL-2 was started after 8 days of culture, and every 2-3 days thereafter. Cultures were started with at least $2.5 \times 10^5$ CD8$^+$ T cells/well and a minimum of 12 wells/condition. A start population of $3\text{-}4 \times 10^6$ CD8$^+$ T cells was sufficient to perform the analysis described here. Every 7 days the cultures were monitored for expansion by determining CD8$^+$ T cells using a Coulter counter and phenotypic analysis for CD8 expression. The number of peptide-specific T cells was monitored by ELISPOT analysis. For this purpose, for every given time point, 3 wells were harvested and placed on PVDF membrane plates, and screened for IFN-γ specific CTL, as is described above. Alternatively, if tetramers are available, phenotypic analysis can be performed for a small set of peptides. If ELISPOT or tetramer analysis demonstrated peptide-specific CTL until day 21, an initial cytotoxicity screen using peptide-pulsed CD40-B cells is initiated on day 25. We perform a single E:T ratio in the range of effector:target cells=10-30:1. If a positive result is obtained in this screen, a second screen is initiated to test if peptide-specific CTL can kill tumor cell lines from the tumor cell panel described below.

Tumor Cell Screening Panel

We have established a panel of tumor cell lines that allows us to determine if peptide-specific CTL recognize tumor cells of different histological origin indicating natural expression and presentation by MHC class I molecules. Furthermore, these cell lines are used to confirm HLA-restriction.

One of the goals of the tumor cell panel is to be able to screen CTL responses to most tumor histologies on the most widely expressed HLA types. The current panel allows the screening for HLA-A2 restricted CTL responses in a wide variety of tumor histologies. To broaden the applicability of the system to other HLA-types, the tumor cell line panel can be genetically characterized for complete HLA expression.

Since we can identify genes by publicly available information, data is available for every new tumor antigen identified using our method, stating the expression of the gene of interest by tumor cells. However, to use the tumor cell line panel as a screening tool for CTL, it is necessary to determine the expression of tumor antigens under study to be able to interpret results from cytotoxicity assays or cytokine release analyses.

The expression of a gene of interest can be examined on protein level. We used an already prepared bank of snap frozen samples (stored at –80° C.) of all cell lines. To measure the protein of interest, cell lysates were prepared using appropriate conditions. For screening purposes, Western blots were performed on mini gels. Alternatively, if monoclonal antibodies against the protein of interest are already available, an ELISA is performed on cellular lysates. The expression analysis on the tumor cell line panel establishes the method of choice that is used to screen primary tumor samples for expression.

If qualitative protein analysis is not feasible due to the lack of appropriate reagents or due to low-level expression of the protein (e.g., hTERT; see below), expression is analyzed on the RNA level. RT-PCR using gene-specific primers is performed using standard techniques. For this purpose, we prepared cDNA from all tumor cell lines in the panel. We established the complete cDNA screening process using gene-specific primers for MAGE-3 and MUC-1. We validated the system by screening two to three genes identified, as is described above. The setup of the RT-PCR screen facilitates automation of this method.

As is noted above, the methods described above for identifying universal TAAs including peptides that bind MHC have been carried out in the identification of the catalytic subunit of telomerase, hTERT. As proof of principle, these methods have also been used to identify MHC-binding peptides within the clonal immunoglobulin of malignant B cells, which is a tumor antigen specific for malignant B cells (i.e., it is not a universal TAA). These studies are described in further detail below.

Framework Derived Peptides from Clonal Immunoglobulin of Malignant B Cells

Most B cell malignancies are characterized by the clonal expansion of a single B cell. Since each Id is patient specific, classical approaches (Boon et al., Annual Review of Immunology 12:337-365, 1994) to determine Id-derived peptides recognized by a patient's T cells are extremely difficult to apply to this particular tumor antigen, and would require investigation in every patient. To overcome this limitation, we applied the approach described above. A large database of Ig sequences from patients with B cell malignancies was screened for peptides binding to HLA-A*0201 using peptide prediction software (Parker, http://bimas.dcrt.nih.gov/molbio/hla_bind). Samples from 192 patients with B cell malignancies were analyzed. The tumor-specific Ig heavy chain rearrangement was PCR amplified and directly sequenced in 128 of these patients (67%). In 35 of these patients, tumorrearranged light chain sequences were also obtained. The 1631 g heavy and light chain rearrangements were translated to their deduced amino-acid sequences. From these sequences 794 peptides were identified with a predicted half-life of β2m-dissociation greater than one minute. From these 794 peptides, 229 (28.8%) were derived from the complementarity determining (CDR) regions of the Ig sequences. The remaining 565 peptides (71.2%) were derived from framework region (FR) motifs. Among the 565 FR-derived peptides, many were shared such that only 272 different peptide sequences were identified. Among these 272 peptides, 29.5% were shared by at least two patients. Peptide binding of a total of 35 peptides, including all peptides with a predicted half-life of binding greater than 2 hours, was performed. Overall, we found a correlation (Spearman rho=0.61, p=0.0001) between the predicted half-life and the ability of the peptides to bind to HLA-A*0201 as determined by the T2 binding assay. Utilizing our current T cell screening system, we identified ten peptides that induced peptide-specific CTL. Sixty-seven percent of the HLA-A2+ patients (42/63) expressed at least one of the common nine FR-derived epitopes in their malignant clonal Ig, showing that a single Ig-derived peptide could be a relevant target in a great number of patients with B cell malignancies. CTL generated against FR-3, FR-4, FR-9, FR-11, and FR-12 demonstrated specific recognition of the parent CLL cells, but not CLL cells that did not express the FR motifs. These results show that the CLL cells were capable of processing and presenting Ig-derived peptides. Specific lysis of target cells was inhibited by anti-HLA-A2 mAb, demonstrating HLA-A2 restriction. CTL generated against peptide FR-12 killed CD40-B pulsed with the corresponding peptide and tumor cells from three patients with CLL expressing this peptide, but not unpulsed CD40-B cells. There was increased killing of CLL cells when they were pulsed with the relevant peptide. Similar results were obtained for peptide FR-11. CD40 activation of the CLL cells also resulted in increased efficiency of killing by the CTL.

Identification of hTERT Peptides Capable of Binding to HLA Class I Antigens hTERT (Genbank Accession No. AF018167) is expressed in more than 85% of human cancers. To begin evaluating the potential usefulness of hTERT as a TAA for cancer immunotherapy, we first analyzed its sequence for peptides that could potentially bind to HLA class I molecules using a peptide-motif scoring system (http://bimas.dcrtnih.gov:80/cgi-bin/molbio/ken_parker_comboform). Starting with the most common HLA subtype, HLA-A*0201, we identified and tested three candidate nonapeptides (Table 1). Each has a unique coding sequence within the currently available human genome sequence. Peptides were synthesized by Genosys Biotechnologies, Inc. (The Woodlands, Tex.).

TABLE 1

Binding of hTERT peptides and controls to human HLA-A*0201

| Name | Sequence | Protein | Position | Score* | Fluorescence Index+ |
|---|---|---|---|---|---|
| I540 | ILAKFLHWL (SEQ ID NO: 1) | hTERT | aa540 | 1746 | 3.1 |
| E555 | ELLRSFFYV (SEQ ID NO: 3) | hTERT | aa555 | 1670 | 2.2 |
| R865 | RLVDDFLLV (SEQ ID NO: 4) | hTERT | aa865 | 542 | 2.2 |

TABLE 1-continued

Binding of hTERT peptides and controls to human HLA-A*0201

| Name | Sequence | Protein | Position | Score* | Fluorescence Index+ |
|---|---|---|---|---|---|
| F271 | FLWGPRALV (SEQ ID NO: 5) (positive control) | MAGE-3 | aa271 | 2655 | 2.7 |
| I540-S | HFLLWKLIA (SEQ ID NO: 6) (negative control) | hTERT | scrambled | 0 | 0.2 |
| A98-Id± | AHTKDGFNF (SEQ ID NO: 7) (negative control) | Idiotype | aa98 | 0 | 0.0 |

*Calculated score in arbitrary units.
+(Mean fluorescence with peptide - mean fluorescence without peptide)/(mean fluorescence without peptide). Results representative of two experiments.
±Peptide sequence obtained from the idiotypic sequence of a patient with plasma cell leukemia and predicted to bind to HLA-B38.

To test the relative binding of each peptide to HLA-A*0201, 50 μg/ml of each peptide plus 5 μg/ml of β2-microglobulin were pulsed onto HLA-A*0201+ TAP-deficient T2 hybridoma cells (ATCC, Rockville, Md.) in serum-free RPMI medium for 18 hours at 37° C. Expression of HLA-A*0201 was then measured by flow cytometry using mAb BB7.2 (ATCC) followed by incubation with FITC-conjugated F(ab')2 goat anti-mouse Ig (Zymed, South San Francisco, Calif.; Nijman et al., Eur. J. Immunol. 23:1215-1219, 1993). Based on significantly increased expression of HLA-A*0201 on pulsed T2 cells, each peptide was found to bind strongly to HLA-A*0201 (Table 1). A positive control peptide derived from the tumor antigen MAGE-3 also bound strongly, but two negative control peptides did not.

Generation of hTERT-Specific CTLs

We then generated CD3+CD8+ CTLs specific for the hTERT peptides and tested them for their ability to kill tumor cells in an hTERT-dependent fashion. These CD3+ CD8+ CTLs were generated as follows. Informed consent was obtained from volunteer blood donors, their peripheral blood mononuclear cells (PBMC) were isolated by leukopheresis and Ficoll-density centrifugation, and dendritic cells (DC), CD40-activated B cells, and CD8-enriched T cells were prepared from PBMC of normal HLA-A*0201 donors, as previously described (Schultze et al., 3. Clin. Invest. 100:2757, 1997).

DC were prepared from PBMC depleted of T, B, and natural killer cells using IL4 and GM-CSF; >80% of these cells were CD83+ CD14−. B cells from PBMC were activated via CD40 and cultured; >80% of these cells were CD19+CD3−. CD8-enriched T cells (>89% CD8+, >95% CD3+, <0.5% CD4+, and <5% CD56+) were prepared from PBMC. Flow cytometry was performed as described in Schultze, supra.

DC were harvested after 7 days in culture, pulsed with peptide (40 μg/ml) and β2-microglobulin (3 μg/ml) for 4 hours at 37° C., irradiated (33 Gy), and added to autologous CD8-enriched T cells at a T:DC ratio of 20:1 in RPMI media with 10% human AB serum, 2 mM glutamine, 15 μg/ml gentamicin, 20 mM HEPES, and 10 ng/ml IL7 (Sigma, Saint Louis, Mo.). At day 7 and weekly thereafter, T cell cultures were harvested and restimulated with irradiated (33 Gy), peptide-pulsed autologous CD40-activated B cells as described in Schultze, supra. IL2 (50 U/ml; Collaborative Biomedical Products, Bedford, Mass.) was introduced on day 8 and replenished as needed every 3-4 days. After three restimulations, 88-90% of cells in each culture were CD3+ lymphocytes, of which 88-90% were CD8$^+$ and 0.3-3.6% were CD4$^+$. Cultures were <0.4% CD14$^+$ and 3.0-3.9% CD56$^+$.

To create target cells in which hTERT was processed naturally, we used amphotropic retroviruses to infect the hTERT-negative, HLA-A*0201$^+$ osteosarcoma line U2OS with either the full coding sequence of hTERT (U2OS-TERT cells) or with retroviral vector alone (U2OS-pB cells). Briefly, the EcoRI-SalI fragment containing the hTERT-HA cDNA was subcloned from plasmid pCI-Neo-hTERT-HA (Counter et al., Oncogene 16:1217, 1998) into the EcoRI-SalI site of pBabe-puro (Morgenstern et al., Nucleic Acids Res. 18:3587, 1990). The carboxyl-terminal HA tag in this construct was deleted by PCR amplification of an hTERT EcoRV-SalI fragment with a primer that deleted the nucleotides encoding the HA tag. U2OS cells were infected with pBabe-puro (negative control) or pBabe-puro-hTERT retroviruses and selected in 0.5 μg/ml of puromycin. Total RNA (40 μg) was isolated from the resulting polyclonal populations and assayed for hTERT expression by an RNase protection assay (FIG. 1A), as described in Counter et al., supra. FIG. 1A shows that U2OS-TERT cells expressed hTERT mRNA, whereas U2OS-pB control cells did not. Input anti-sense probes are shown on the left of FIG. 1A, and RNase-resistant, protected fragments representing hTERT and human β-actin are shown on the right.

Figure 1B:
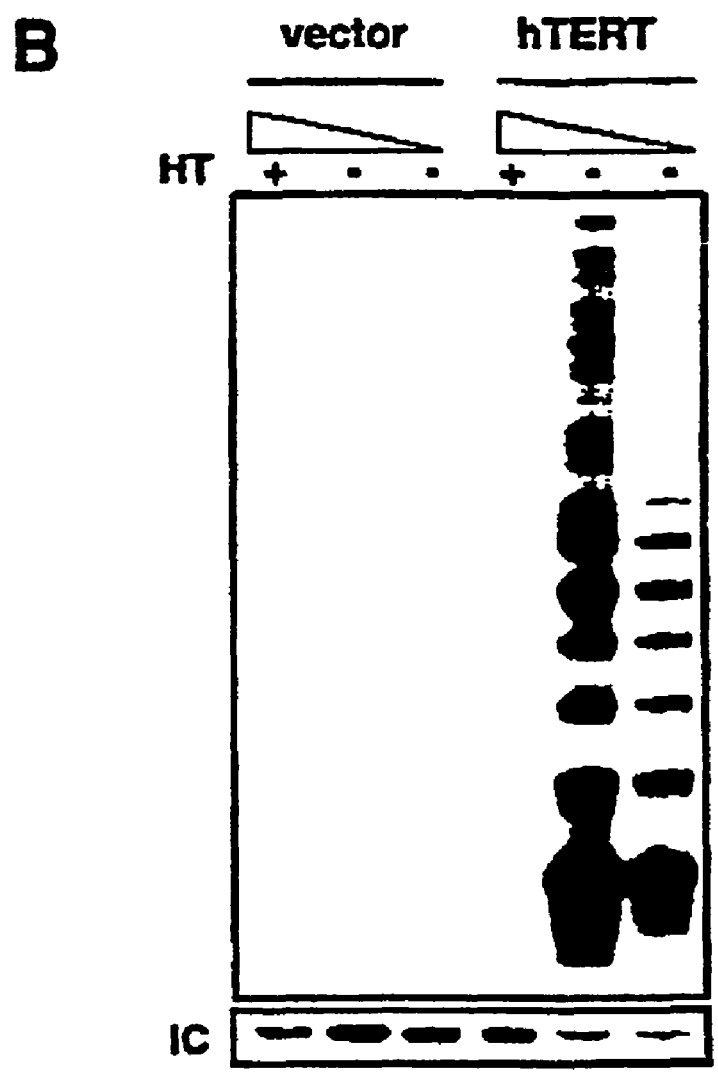
FIG. 1B is an autoradiogram showing telomerase activity in U20S cells expressing hTERT.

FIG. 1B shows that U2OS-TERT cells demonstrated telomerase activity, whereas U2OS-pB cells did not. In this experiment, 0.2 μg or 0.02 μg of cytosolic cellular extracts prepared from the vector- or hTERT-infected cells was assayed for telomerase activity using a PCR-based telomerase repeat amplification protocol (TRAP; Kim et al., Nucleic Acids Res. 25:2595, 1997). As a negative control, 2 μg of each extract was heat treated (HT) to inactivate telomerase prior to assay.

U2OS-TERT and U2OS-pB cells expressed similar levels of HLA-A*0201 and CD58, and lacked MHC class II, CD54, and CD80.

FIG. 2A shows that CTLs generated by stimulation with the hTERT peptide I540 lysed only hTERT-positive cells. U2OS-TERT cells (solid symbols) and U2OS-pB cells (open symbols) were labeled with Cr$^{51}$ and used as targets for I540-stimulated CTLs (squares) or MAGE-3-stimulated CTLs (circles). Standard 4-hour Cr$^{51}$-release assays after the third or fourth restimulation were performed to measure cytotoxicity. Assays were done in triplicate per condition using 5×10$^3$ labeled target cells per well in a 96-well plate, and percent specific lysis was calculated from cpm of (experimental result–spontaneous release)/(maximum release–spontaneous release). The mean results (±1 S.D.) of one experiment, representative of three performed, are shown. I540-stimulated CTLs killed only U2OS-TERT cells. In contrast, CTL cultures generated by stimulation with the other two candidate hTERT peptides or with the MAGE-3 peptide did not lyse either U2OS-TERT cells or U2OS-pB cells (FIG. 2A).

FIG. 2B shows that the lysis of hTERT-positive cells by I540-specific CTLs is HLA class I-restricted. I540-specific cytotoxicity against U2OS-TERT cells was tested at an effector:target ratio of 30:1. Consistent with HLA-restricted cytotoxicity, lysis of U2OS-TERT cells by I540-specific CTLs was inhibited by the anti-HLA-A2 mAb BB7.2, but not with media or the anti-B5 control mAb. The results shown in FIGS. 2A and 2B strongly suggest that the I540 hTERT peptide fulfills the requirements for a TAA capable of triggering CTL responses: the peptide is naturally processed by tumor cells, presented in an MHC-restricted fashion, and permits expansion of hTERT-specific CTLs.

I540-Specific CTLs Recognize Tumor Cell Lines that Express hTERT

To test whether I540-specific CTLs can recognize hTERT in a broad range of tumors, cytotoxicity was evaluated against a panel of tumor cells with diverse histologic origins. The 36M ovarian carcinoma cell line generated from patient ascites was a gift of Dr. Stephen Cannistra, Dana-Farber Cancer Institute. The EBV-transformed B cell line B4 (Counter et al., J. Virol. 68:3410, 1994) was provided by Dr. Chris Counter, Duke University. The transformed kidney cell line 293, the lung carcinoma line Calu-1, the multiple myeloma cell lines U266, IM9, and HS-Sultan, and the EBV-transformed B cell line SKW6.4 were obtained from the ATCC (Rockville, Md.). The malignant melanoma cell lines K029 and K017, generated from biopsy specimens, were a gift of Dr. Glenn Dranoff, Dana-Farber Cancer Institute.

Figure 3A:
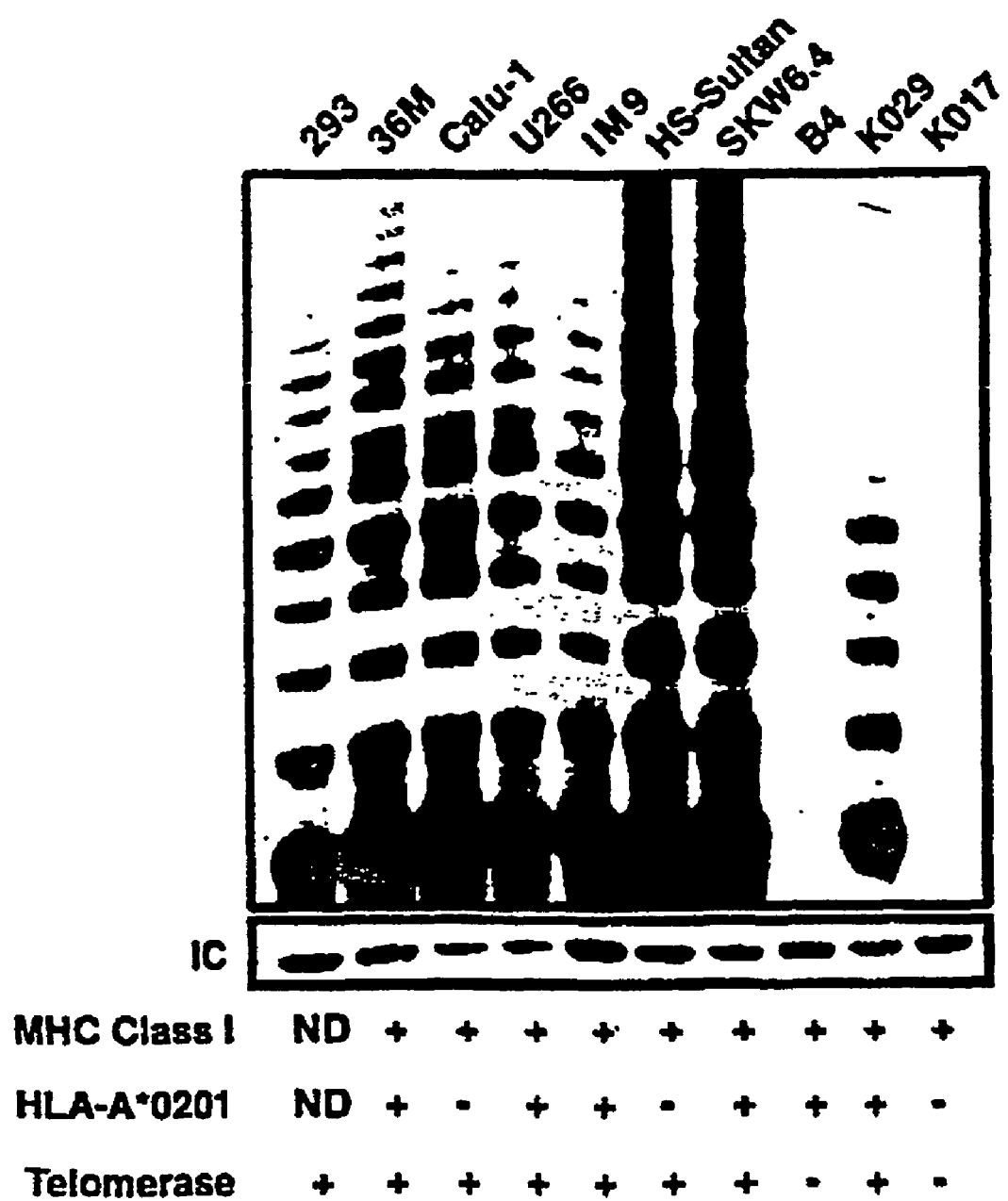
FIG. 3A is an autoradiogram showing telomerase activity in tumor cell lines.

Cytosolic extracts were prepared from each cell line and assayed for telomerase activity as described for the experiment shown in FIG. 1B. For Calu-1, B4, K029, and K017, 1 μg of extract was used in the assay. For each other cell line, 200 ng of cytosolic extract was used, except 293 cells (positive control), for which 30 ng was used. Telomerase activity was observed in all tumors except one melanoma cell line (FIG. 3A). The TRAP internal control (IC) is shown for each extract. HLA class I expression was determined for each cell type shown in FIG. 3A by flow cytometry as described (Schultze et al., J. Clin. Invest. 100:2757, 1997); each tumor cell type expressed nearly equal amounts of surface MHC class I. HLA-A*0201 typing was evaluated by serology and confirmed by PCR amplification in our institute's clinical laboratory.

FIGS. 3B-3E are graphs showing that I540-specific CTLs lyse tumor cells from a wide variety of histologic origins in an HLA-A*0201-restricted and telomerase-dependent fashion. FIGS. 3B-3E show the cytotoxicity of I540-specific CTLs against carcinoma (FIG. 3B), multiple myeloma (FIG. 3C), malignant melanoma (FIG. 3D), and EBV-transformed B cell lines (FIG. 3E). Experiments were performed as described for FIG. 2. The mean results of one experiment, representative of two experiments performed, are shown ±1 S.D. Lysis of U2OS-TERT cells is shown for comparison in each graph. HLA-A*0201 (A2) and telomerase (Tel) phenotypes for each target cell type are summarized in FIG. 3A.

The I540-specific CTLs lysed an HLA-A*0201$^+$ carcinoma line, but not an HLA-A*0201-negative carcinoma line (FIG. 3B); in contrast, CTLs generated using the MAGE-3 peptide did not lyse either carcinoma line. Similarly, the I540-specific CTLs lysed two HLA-A*0201$^+$ multiple myeloma cell lines but not an HLA-A*0201-negative myeloma line (FIG. 3C), and also lysed an HLA-A*0201+ malignant melanoma line but not an HLA-A*0201-negative, telomerase-negative melanoma line (FIG. 3D).

Finally, we tested I540-specific CTLs against Epstein Barr virus (EBV)-transformed B cell lines as a model of EBV-related lymphoproliferative disorders. Each of these lines expressed HLA-A*0201, but only the line SKW6.4 was telomerase-positive; B4 is a mortal, pre-crisis line and therefore telomerase-negative (FIG. 3A) (Counter, et al., J. Virol. 68:3410, 1994). I540-specific CTLs lysed SKW6.4 but not B4 (FIG. 3E), further demonstrating hTERT specificity of the cytotoxic response. The results shown in FIGS. 3A-3E demonstrate that in a wide range of tumors and transformed cells, endogenous hTERT is naturally processed, presented in the context of HLA-A*0201, and serves as a target for antigen-specific CTLs.

Figure 4A:
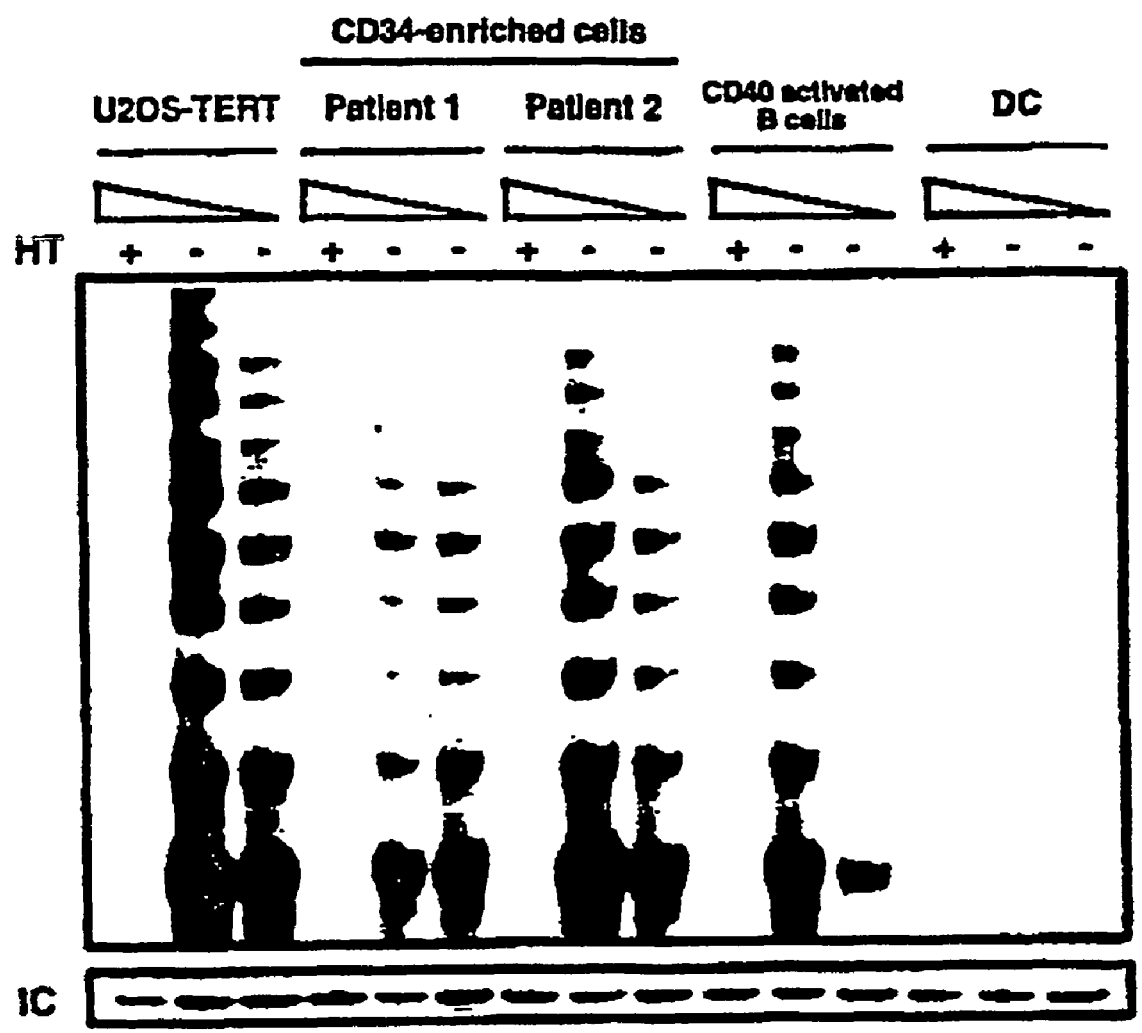
FIG. 4A is an autoradiogram showing the level of telomerase activity in U2OS-TERT cells, NHL from two patients, and AML from one patient.
Figure 4B:
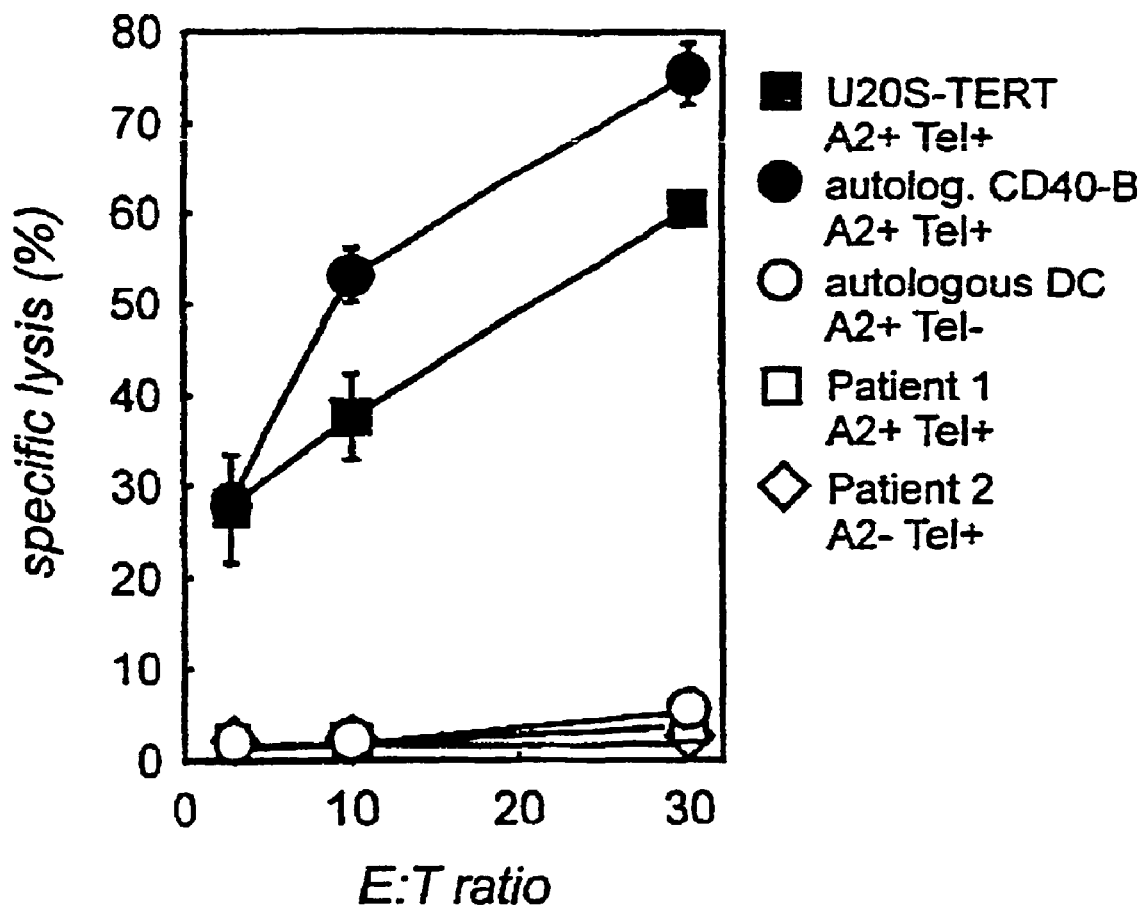
FIG. 4B is a graph showing that I540-specific CTL lysed NHL and AML cells in an HLA-A*201-restricted fashion

To investigate the possibility that I540-specific cytotoxicity was restricted to immortalized cell lines, we then studied CTL lysis of freshly isolated, primary tumor cells. Acute myelogenous leukemia (AML) cells were obtained by bone marrow aspiration from an HLA-A*0201 patient at the time of clinical presentation, and non-Hodgkin's lymphoma (NHL) cells from two patients were obtained after biopsy of markedly involved lymph nodes. One NHL patient expressed HLA-A*0201 (patient 1) whereas the other patient was HLA-A*0201 negative but MHC class I-positive (patient 2). Each primary tumor tested was telomerase-positive (FIG. 4A). As is shown in FIG. 4B, I540-specific CTL lysed the HLA-A*0201 AML and NHL cells, but not the HLA-A*0201 negative NHL cells. These results demonstrate that in a range of primary tumors and transformed cell lines, endogenous hTERT is naturally processed, presented in the context of HLA-A*0201, and serves as a target for antigen-specific CTL.

To evaluate the relative efficiency of I540 recognition by the CTL populations tested and hence to assess the significance of the level of cytotoxicity obtained against telomerase positive cells, we compared cytotoxicity of I540 CTL with MAGE-3 F271 CTL against the same target. The K029 melanoma cell line was used as the target because it endogenously expresses both hTERT and MAGE-3. Two pairs of I540-specific and F271-specific CTL were generated (including one pair form the same donor), and were directly compared. Over a range of E:T ratios, I540-specific and F271-specific cytotoxicity against K029 was similar (e.g., 46.1% versus 32.0%, respectively, for one pair of CTL, and 87.0% versus 64.7% for a second pair of CTL generated from the same donor, tested at an E:T ratio of 30:1). Although this finding suggests that CTLs recognizing I540 and F271 have similar cytotoxic efficiencies for tumor cells expressing these antigens, we are currently generating a panel of T cell clones form healthy donors and cancer patients to answer this question definitively.

Testing for hTERT Autoimmunity

Because the vast majority of human cancers have high levels of telomerase activity, immunotherapeutic strategies aimed at this antigen potentially have broad clinical applications. The major concern of such approaches would be cytolysis of the few normal cell types in which telomerase is detected. Telomerase activity has not been detected in adult cardiac, renal hepatic, pulmonary, neural, skeletal, and adipose tissues; however, hematopoietic stem cells and progenitors (Broccoli et al., Proc. Natl. Acad. Sci. U.S.A. 92:9082, 1995; Hiyama et al., J. Immunol. 155:3711, 1995; Buchovich et al., Mol. Bio. Cell 7:1443, 1996), germinal center cells, basal keratinocytes, gonadal cells, and in some studies, certain proliferating epithelial cells (Igarashi et al., Blood 89:1299, 1997; Norrback et al., Blood 88:222, 1996; Harle-Bachor et al., Proc. Natl. Acad. Sci. U.S.A. 93:6476, 1996; Yasumoto et al., Oncogene 13:433, 1996; Weng et al., Proc. Natl. Acad. Sci. U.S.A. 94: 10827, 1997; Kolquist et al., Nat. Genet. 19:182, 1998) have measurable telomerase activity. We therefore examined I540-specific CTL lysis of normal cells, starting with peripheral blood CD34$^+$ cells as important potential targets. CD34-enriched cells from two patients with lung cancer were studied (patient cells were obtained for these experiments from excess material with the permission of our institution's Internal Review Board). These patients had undergone stem cell mobilization with chemotherapy in preparation for autologous stem cell transplantation. Cells from Patient 1 were HLA-A*0201$^+$ and 45% CD34$^+$CD45$^+$, and cells from Patient 2 were HLA-A*0201$^-$ (but Class I$^+$) and 76% CD34$^+$CD45$^+$.

FIGS. 4A and 4B show an evaluation of I540-specific CTL cytotoxicity against normal hematopoietic cells. In FIG. 4A, telomerase activity is shown for U2OS-TERT cells, CD34$^+$-enriched peripheral blood cells from Patients 1 and 2, CD40-activated B cells, and DC. For U2OS-TERT cells, 300 ng or 100 ng of cytosolic extract were used; for the other cells, 1 µg or 300 ng were used. As a negative control, 2 µg of each extract was heat treated (HT) to inactivate telomerase prior to assay. The TRAP internal control (IC) is shown for each reaction.

In FIG. 4B, I540-specific CTLs were tested for cytotoxicity against CD34-enriched cells, autologous DC, and autologous CD40-activated B cells. Lysis of U2OS-TERT cells is shown for comparison. HLA-A*0201 (A2) and telomerase (Tel) phenotypes are summarized for each target. Experiments were performed as in FIG. 2. The mean results of one experiment, representative of two performed, are shown ±1 S.D.

Although the CD34-enriched cells of each patient had telomerase activity (FIG. 4A), no lysis by I540-specific CTLs was observed (FIG. 4B), suggesting that hTERT does not readily function as an autoantigen on hematopoietic precursor cells. This finding can reflect a level of hTERT=expression on CD34-enriched cells that is insufficient for CTL activation, but still sufficient for detection by the PCR-based telomerase assay (quantitative differences in hTERT expression between cell types cannot be determined by the PCR telomerase assay, although qualitative differences such as the presence or absence of signal are meaningful (Prowse et al., Proc. Natl. Acad. Sci. U.S.A. 92:4818, 1995).

Assuming that hTERT expression in stem cells and progenitors is not rate-limiting for CTL activation, we hypothesized that these cells might not be recognized as hTERT-specific CTL targets because of an hTERT processing defect that limits or prohibits the presentation of hTERT peptides in the groove of MHC Class I. We therefore examined the ability of I540-specific CTLs to lyse professional antigen presenting cells in which any such defect would be less likely to be present. Autologous DC prepared from peripheral blood lacked telomerase activity and were not lysed by I540-specific CTL (FIGS. 4A and 4B). Resting peripheral B cells also lack telomerase activity, but after prolonged stimulation in vitro with CD40 ligand, display detectable telomerase activity (FIG. 4A). CD40-activated B cells are excellent antigen presenting cells (Schultze et al., J. Clin Invest. 100:2757, 1997) and parallel germinal center B cells in many ways, including their telomerase activity. As shown in FIG. 4B, autologous CD40-activated B cells were lysed by I540-specific CTL. Therefore, it is theoretically possible that hTERT-specific CTLs could, if given therapeutically, kill germinal center B cells and other activated B cells. However, our observation that DCs lack telomerase activity suggests that DCs could maintain primary antigen-specific T cell activation even if exposed to hTERT-specific CTLs.

Figure 5A:
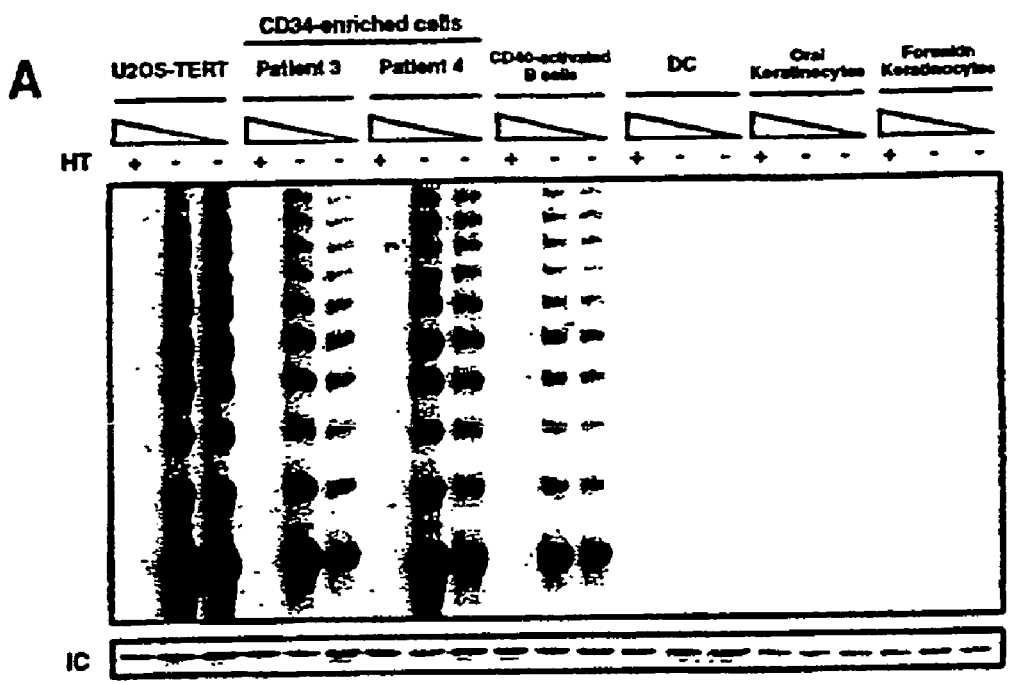
FIG. 5A is an autoradiogram showing the level of telomerase activity in U2OS-hTERT cells, patient-derived, CD34-enriched, peripheral blood cells, CD40-activated B cells, and dendritic cells.
Figure 5B:
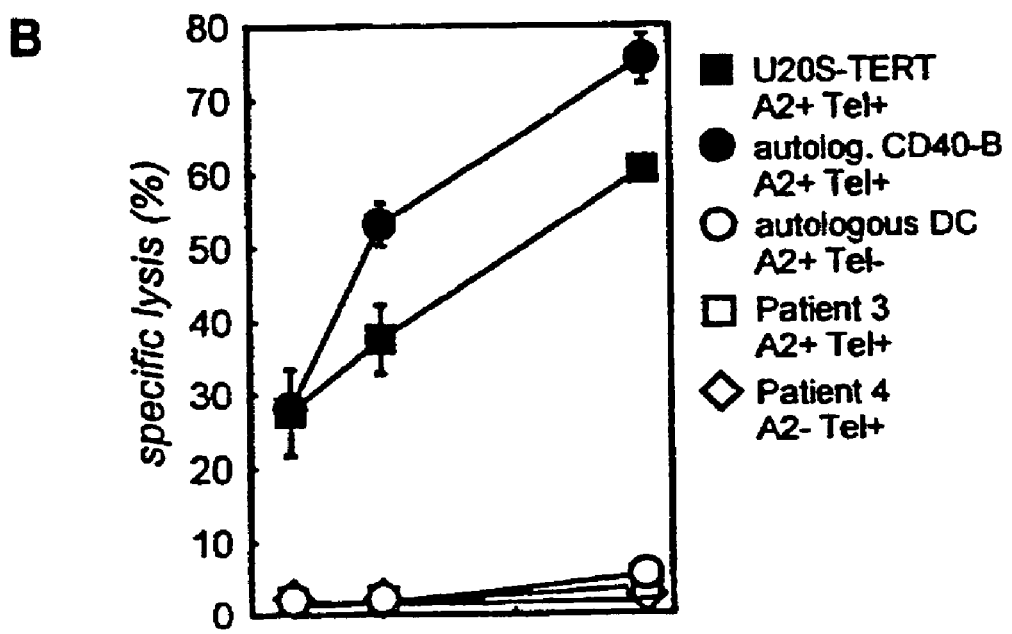
FIG. 5B is a graph showing that certain normal hTERT-expressing cells are not lysed by I540-specific CTLs.

In an attempt to test whether other normal telomerase-positive cells are susceptible to hTERT-specific lysis, we obtained freshly isolated human foreskin keratinocytes and human oral keratinocytes and tested them for telomerase activity. Consistent with other reports (Klingelhutz et al., Mol. Cell. Biol. 14:961-969, 1994; Klingelhutz et al., Nature 380:79-82, 1996; Stoppler et al., J. Biol. Chem. 272:13332-13337, 1997; Kiyono et al., Nature 396:84-88, 1998), we did not find that freshly isolated keratinocytes express detectable telomerase activity (FIG. 5A). In a report that identifies telomerase-positive keratinocytes (Harle-Bachor et al., Proc. Natl. Acad. Sci. USA 93:6476-6481, 1996), the authors were only able to isolate telomerase-positive cells through a time-sensitive, trypsin fractionation protocol from whole epidermis. This protocol produced enough cells to perform the PCR-based TRAP assay but insufficient to perform chromium-release assays. Likewise, we have been unable to establish a primary epithelial cell culture that expresses endogenous telomerase. Consequently, extensive in vitro evaluation as to whether hTERT specific CTL would lyse normal telomerase positive cells requires the ability to first obtain such cells in sufficient quantity for the appropriate assays. Clinical attempts to target hTERT as a tumor antigen in cancer patients also offers major insights into this question.

In summary, we demonstrate that a peptide derived from the catalytic subunit of human telomerase can be naturally processed by tumor cells, presented in an HLA-A*0201-restricted fashion, and serve as a target for antigen specific CTL. Furthermore, cytotoxicity can be directed against target cells from a wide variety of histologic origins including carcinoma, sarcoma, multiple myeloma, malignant melanoma, acute leukemia, Non-Hodgkin's Lymphoma, and EBV-transformed B cells. These findings, together with the identification of telomerase in the vast majority of human cancers, suggest that hTERT represents the most commonly-expressed TAA yet described.

We did not observe cytotoxicity against telomerase-positive, $CD34^+$ (telomerase-positive) peripheral blood cells. Given that more than 85% of all cancers contain hTERT-expressing tumor cells, and that nearly 50% of the population expresses the HLA-A*0201 allele, almost half of all cancer patients can benefit from immunotherapeutic strategies employing the I540 hTERT peptide. The percentage of cancer patients benefiting from hTERT-specific immunotherapies can be further increased by use of additional hTERT peptides that bind to other HLA alleles.

Identification of TAA Peptides that Bind to Histocompatibility Molecules

For the full characterization of hTERT as a widely expressed tumor antigen, additional CTL epitopes derived from hTERT can be pursued. It is important in the design of hTERT-specific immunotherapies to identify multiple hTERT epitopes restricted to HLA-A*0201, as well as multiple epitopes restricted to other HLA alleles. In the case of hTERT, tumor progression is characterized by increased expression and activity of telomerase (Kolquist et al., Nat. Genet. 19:182-186, 1998). Nevertheless, mutations within a single epitope that do not disrupt function are at least hypothetically possible and could facilitate tumor resistance to clinical strategies based on a single epitope.

Numerous previous investigations have identified T cell epitopes based on the reactivity of patient-derived, tumor specific clones. An alternative strategy, as is described above, is to deduce CTL epitopes from the known sequences of genes that encode candidate tumor antigens, such as hTERT. Our hypothesis behind this strategy contends that CTL epitopes can be predicted by comparing candidate protein sequences with amino acid motifs thought to be important for MHC/peptide binding. For certain HLA alleles, and in particular HLA-A*0201, a great deal of empiric data on MHC/peptide binding has been utilized to delineate these motifs, leading to highly specific and moderately sensitive prediction algorithms for MI-IC/peptide affinities (Parker et al., J. Immunol. 152:163, 1994). Binding to HLA-A*0201, for example, is favored by Leu or Met residues at anchor position 2 and by Leu and Val residues at anchor position 9. Glu, Asp, or Lys residues at position 4 also favor binding to this allele.

A computer-assisted peptide-binding prediction program is available on the Internet bimas.dcrt.nih.gov:80/cgi-bin/molbio/ken_parker_comboform), which, for a given allele, scores candidate peptides for their estimated dissociation half life (in minutes). Numerous hTERT-derived 9mers and 10mers are predicted to bind to HLA-A*0201, and these peptides represent candidate CTL epitopes with high affinity for this allele (Table 2). Furthermore, this type of analysis also predicts binding of several other hTERT-derived peptides to non-HLA-A*0201 alleles (Table 3). It has become evident that the threshold of scores that predict binding varies for each HLA allele and will be determined by analyzing scores of peptides previously shown to bind (i.e., "positive controls" in Tables 2 and 3). For example, scores above 500 predict high-affinity binding to HLA-A*0201 whereas scores above 80 and 90 predict binding to HLA-A3. For each hTERT peptide listed in Tables 2 and 3, initial BLAST searches indicate a unique coding sequence within the currently available genomic database. For any given patient, therefore, it is possible to assemble a panel of hTERT peptides, rather than a single epitope potentially prone to mutation, suitable for targeting in immunotherapeutic approaches.

With respect to hTERT, potentially useful TAA peptides will have scores greater than 150, preferably, greater than 300, more preferably, greater than 500, even more preferably, greater than 1000, still more preferably, greater than 1500, and most preferably, greater than 1700. In the case of hTERT, although peptides from any portion of the hTERT amino acid sequence can be used as a peptide in the methods of the invention, preferred hTERT peptides are from the amino acid region that spans amino acid 350 through amino acid 1000; this amino acid region contains conserved telomerase-specific and RT motifs, and, hence, tumors that express hTERT are less likely to acquire mutations in this region, thereby evading an hTERT-specific immune response. Although 8-mer TAA peptides can be used in the methods of the invention, 9-mer and 10-mer peptides are preferred.

Peptide motif scoring systems can also be used to identify useful 9-mer and 10-mer TAA peptides that contain substitutions at up to three amino acid positions. Any substituted peptide that displays a score greater than 150, as is described above, can be used in the methods of the invention. Table 3 shows examples of various 9-mer and 10-mer hTERT peptides that can be useful in the methods of the invention, their HLA class I binding partners, and their relative scores (i.e., estimated half time of dissociation from an HLA molecule of a molecule containing the hTERT peptide sequence) according to the "HLA Peptide Binding Predictions" program.

Other methods for identifying peptides that bind to a histocompatibility antigen of interest are known to those of skill in the art (see, e.g., Paul *Fundamental Immunology* 3$^{rd}$ Edn. Chpt. 17, pages 641-643, 1993, and references cited therein).

To evaluate these candidate peptides as potential CTL epitopes, the following strategy is used. Each peptide is synthesized and tested for binding to the restricted HLA allele. If binding is established, CTL are generated from normal donors, and those cultures able to be expanded are screened for antigen reactivity using peptide-pulsed DC. If antigen-specific CTL are generated, cytotoxicity is tested against a panel of tumor cell lines with diverse histologies. For each peptide, these studies establish whether the peptide (1) binds to the appropriate MHC Class I molecule, (2) is processed by tumor cells such that antigen-derived peptides are available for binding to MHC molecules, and (3) is recognized by the T cell repertoire in an MHC-restricted fashion such that naive CTL precursors bearing specific T cell receptors can be expanded.

Peptides are synthesized by, for example, Fmoc methods (Sigma Genosys). Binding to HLA-A*0201 is measured using the TAP-deficient T2 hybridoma cell line, whose limited HLA-A*0201 expression is markedly upregulated by incubation with peptides that bind to HLA-A*0201. In this assay, TAP-deficient T2 cells (ATCC) are pulsed with 50 µg/ml of β2-microglobulin (Sigma) for 18 hours at 37° C. HLA-A*0201 expression is then measured by flow cytometry using mAb BB7.2 (ATCC), followed by incubation with FITC-conjugated F(ab')$_2$ goat anti-mouse Ig (Zymed).

To assess peptide binding to other HLA alleles, T2 transfectant cells expressing other Class I molecules are used along with antibodies specific for these particular alleles.

TABLE 2

Candidate hTERT peptides predicted to bind to HLA-A*0201

| HLA | hTERT | Sequence | Score* |
|---|---|---|---|
| A*0201 | K1081 | KLTRHRVTYV (SEQ ID NO: 8) | 3079 |
|  | L933 | LLLDTRTLEV (SEQ ID NO: 9) | 1794 |
|  | F544 | FLHWLMSVYV (SEQ ID NO: 10) | 1760 |
|  | F1078 | FLLKLTRHRV (SEQ ID NO: 11) | 1184 |
|  | W547 | WLMSVYVVEL (SEQ ID NO: 12) | 836 |
|  | G804 | GLFDVFLRFM (SEQ ID NO: 13) | 725 |
|  | L152 | LLARCALFV (SEQ ID NO: 14) | 650 |
|  | W1072 | WLCHQAFLL (SEQ ID NO: 15) | 570 |
|  | V554 | VELLRSFFYV (SEQ ID NO: 16) | 516 |
| Positive Control |  |  |  |
|  | MAGE-3 271-79 | FLWGPRALV (SEQ ID NO: 17) | 2655 |
|  | HTLV-1 tax 11-19 | LLFGYPVYV (SEQ ID NO: 18) | 2406 |
|  | Hbv cAg 18-27 | FLWGPRALV (SEQ ID NO: 19) | 2310 |
|  | Inf MP 58-66 | GILGFVFTL (SEQ ID NO: 20) | 551 |

*Calculated score is a predicted estimate of dissociation half-time (minutes) for the peptide binding to HLA. For any particular allele, the threshold for scores predictive of peptide binding is determined by evaluating the scores of viral- or tumor-derived positive control peptides known to bind to the allele (http://www.uni-tuebingen.de/uni/kxi/class1.htm). Additional candidate HLA-2 binding, hTERT peptides are presented in Table 4, below.

TABLE 3

Candidate hTERT peptides predicted to bind to non-HLA-A2 alleles

| HLA | hTERT peptide | Sequence | Score* |
|---|---|---|---|
| A1 | Y325 | YAETKHFLY (SEQ ID NO: 21) | 225 |
|  | V553 | VVELLRSFFY (SEQ ID NO: 22) | 225 |
|  | I1036 | ISDTASLCY (SEQ ID NO: 23) | 187 |
| Positive Controls |  |  |  |
|  | MAGE-3 168-76 | EVDPIGHLY (SEQ ID NO: 24) | 250 |
|  | Inf. A NP 44-52 | CTELKLSDY (SEQ ID NO: 25) | 112 |
| A3 | G804 | GLFDVFLRF (SEQ ID NO: 26) | 270 |
|  | K973 | KLFGVLRLK (SEQ ID NO: 2) | 101 |
|  | R535 | RLREEILAK (SEQ ID NO: 27) | 90 |
| Positive Controls |  |  |  |
|  | Inf. A. NP 265-73 | ILRGSVAHK (SEQ ID NO: 28) | 90 |
| A11 | Y562 | YVTETTFQK (SEQ ID NO: 29) | 6.0 |
|  | Q995 | QTVCTNIYK (SEQ ID NO: 30) | 3.0 |
|  | K881 | KTFLRTLVR (SEQ ID NO: 31) | 2.4 |
|  | R535 | RLREEILAK (SEQ ID NO: 32) | 2.4 |
| Positive Controls |  |  |  |
|  | HIV-1 p24 349-59 | GVGGPGGHK (SEQ ID NO: 33) | 6.0 |
|  | EBNA-4 416-24 | IVTDFSVIK (SEQ ID NO: 34) | 2.0 |
| A24 | T1088 | TYVPLLGSL (SEQ ID NO: 35) | 432 |
|  | C845 | CYGDMENKL (SEQ ID NO: 36) | 316 |
|  | F575 | FYRKSVWSKL (SEQ ID NO: 37) | 308 |
|  | A165 | AYQVCGPPL (SEQ ID NO: 38) | 300 |
| Positive Controls |  |  |  |
|  | HIV-1 gp41 583-91 | RYLKDQQLL (SEQ ID NO: 39) | 720 |
|  | P15/mel Ag 10-18 | AYGLDFYIL (SEQ ID NO: 40) | 240 |

*Calculated score is a predicted estimate of dissociation half-time (minutes) for the peptide binding to HLA. For any particular allele, the threshold for scores predictive of peptide binding is determined by evaluating the scores of viral- or tumor-derived positive control peptides known to bind to the allele (http://www.uni-tuebingen.de/uni/lkxi/class1.htm).

TABLE 4

Additional Candidate HLA-2 binding, hTERT peptides

| R572 | RLFFYRKSV (SEQ ID NO: 41) |
| L1017 | LQLPGHQQV (SEQ ID NO: 42) |
| R30 | RLGPQGWRL (SEQ ID NO: 43) |
| S504 | SLQELTWKM (SEQ ID NO: 44) |
| N95 | NVLAFGFAL (SEQ ID NO: 45) |
| V407 | VLLKTHCPL (SEQ ID NO: 46) |
| F870 | FLLVTPHLT (SEQ ID NO: 47) |
| T765 | TLTDLQPYM (SEQ ID NO: 48) |
| I836 | ILSTLLCSL (SEQ ID NO: 49) |
| L548 | LMSVYVVEL (SEQ ID NO: 50) |
| F986 | FLDLQVNSL (SEQ ID NO: 51) |
| L675 | LLGASVLGL (SEQ ID NO: 52) |
| C76 | CLKELVARV (SEQ ID NO: 53) |
| L934 | LLDTRTLEV (SEQ ID NO: 54) |
| G932 | GLLLDTRTL (SEQ ID NO: 55) |
| F88 | FLRTLVRGV (SEQ ID NO: 56) |

TABLE 4-continued

Additional Candidate HLA-2 binding, hTERT peptides

| | |
|---|---|
| Y772 | YMRQFVAHL (SEQ ID NO: 57) |
| R724 | RLTEVIASI (SEQ ID NO: 58) |
| Q1024 | QVWKNPTFFL (SEQ ID NO: 59) |
| V1016 | VLQLPFHQQV (SEQ ID NO: 60) |
| F345 | FLLSSLRPSL (SEQ ID NO: 61) |
| L862 | LLLRLVDDFL (SEQ ID NO: 62) |
| K511 | KMSVRGCAWL (SEQ ID NO: 63) |
| R87 | RLCERGAKNV (SEQ ID NO: 64) |
| L139 | LLLRRVGDDV (SEQ ID NO: 65) |
| G674 | GLLGASVLGL (SEQ ID NO: 66) |
| L1005 | LLLQAYRFHA (SEQ ID NO: 67) |
| K1106 | KLPGTTLTAL (SEQ ID NO: 68) |
| V1070 | VQWLCHQAFL (SEQ ID NO: 69) |
| A49 | ALVAQCLVCV (SEQ ID NO: 70) |
| R865 | RLVDDFLLVT (SEQ ID NO: 71) |
| S835 | SILSTLLCSL (SEQ ID NO: 72) |

This assay can also be applied to other non-HLA-A2 alleles. T2 cells are transfected with genes from additional class I alleles and selected for stable expression using techniques as described (Anderson et al., J. Immunol. 151:3407-3419, 1993). Importantly, the generation of only a few types of T2 HLA transfectants (e.g., a panel including A*0101, A*0301, A*1101, and A*2401 transfectants in addition to wild-type T2 cells) allows determination of epitopes relevant to more than 95% of cancer patients.

CTL are generated from normal donors according to a protocol of DC/CD40-B cell activation we have previously described (Schultze et al., J. Clin. Invest. 100:2757-2765, 1997; see above). In this system, DC are prepared from peripheral blood using IL4 and GM-CSF. B cells are activated and cultured via CD40, as described (Schultze et al., J. Clin. Invest. 100:2757-2765, 1997). After 7 days in culture, DC are harvested, pulsed with peptide (40 μg/ml) and β2-microglobulin (3 μg/ml) for 4 hours at 37° C., irradiated (33 Gy), and added to autologous CD8-enriched T cells at a T:DC ratio of 20:1 in RPMI media with 10% human AB serum, 2 mM glutamine, 15 μg/ml gentamicin, 20 mM HEPES, and 10 ng/ml IL7 (Endogen). At day 7 and weekly thereafter, T cell cultures are harvested and restimulated with irradiated (33Gy), peptide-pulsed autologous CD40-activated B cells, as described (Schultze et al., J. Clin. Invest__ 100:2757-2765, 1997). IL2 (50 U/ml; Collaborative Biomedical Products) is introduced on day 8 and replenished as needed every 3-4 days. Cultures are evaluated for cell surface expression of CD3, CD4, CD8, CD56, CD19, and CD20 after the third or fourth restimulation and subsequently analyzed for cytotoxicity in standard chromium release assays.

For the initial screen of CTL specificity, autologous peptide-pulsed DC are used as screening targets. DC are telomerase-negative, whereas other screening targets (e.g., activated B cells or T2 cells) are telomerase-positive and cannot be used in peptide pulsing experiments (see below). DC pulsed with control peptides are used as a negative screening target. Four-hour $Cr^{51}$-release assays are performed in triplicate per condition using $5 \times 10^3$ labeled target cells per well in a 96-well plate. Percent specific lysis is calculated from cpm of (experimental result−spontaneous release)/(maximum release−spontaneous release).

In addition, for hTERT peptides predicted to bind to HLA-A*0201, CTL cytotoxicity is reevaluated using as screening targets the osteosarcoma cell line U2OS, previously infected with hTERT or retroviral vector alone (see below). Wild-type U2OS is a rare tumor cell line that is telomerase-negative (Bryan et al., Nat. Med. 3:1271, 1997). HTERT-specific lysis is reflected by lysis of the hTERT-infected U2OS cells in the absence of lysis of vector-only infected U2OS cells. Finally, as CTL specific for hTERT peptides are generated, they are tested for cytotoxicity against a panel of wild-type tumor cell lines from a wide range of histologies. Such a panel was used to characterize the I540 hTERT peptide, and includes combinations of carcinoma, melanoma, myeloma, and EBV-transformed B cell lines that control for MHC-restriction and hTERT-specificity. These experiments are important not only to evaluate whether the additional hTERT epitopes identified are naturally processed and presented by tumor cells, but also to test the "universality" of each epitope in a range of histologies.

Finally, CTL elaboration of cytokines is also measured following CTL exposure to hTERT peptides and MHC. This exposure can be achieved using peptide-pulsed DC, or, in the case of HLA-A*0201, the infected and control U2OS cells. Assays to measure INFγ and TNF follow previously described methods (Schultze et al., J. Ciin. Invest. 100:2757-2765, 1997). It is important to compare hTERT-specific CTL cytotoxicity with cytokine release, as some studies have suggested that cytokine elaboration of specific CTL has a greater correlation with clinical effect than cytotoxicity responses (see, e.g., Aruga et al., Cancer Immunol. Immunother. 41:317-324, 1995).

In choosing which hTERT peptides to test initially, the first criterion is the efficiency of binding to MHC, as reflected by the relative fluorescence shift in the T2 assay. Secondary criteria include where in the hTERT sequence the peptide is located. Higher priority is placed on peptides found within or near either the "telomerase-specific" motif (residues 556 to 565) or one of the six reverse-transcriptase motifs (starting at residues 621, 631, 704, 823, 862, and 895) (Meyerson et al., Cell 90:643-651, 1997; Nakumura et al., Science 277:955-959, 1997). The reason for this priority is the hypothesis that mutations within these regions, although potentially resulting in resistance to CTL lysis, might disrupt the functional activity of telomerase. Interruption of telomerase activity in wild-type telomerase-positive tumors can be a lethal development (Feng et al., Science 269:1236-1241, 1995).

Higher priority for testing is also assigned to peptides found within regions that contain clusters of other predicted peptides. For example, initial review of hTERT indicates that numerous candidate epitopes for multiple alleles localize to a 50mer stretch of hTERT starting at residue 535. Notably, the I540 peptide previously identified is found within this 50mer. In addition, several candidate epitopes are also identified in a 25mer stretch of hTERT starting at residue 1072, including three potential HLA-A*0201-binding peptides relatively short regions of hTERT found to contain multiple CTL epitopes for multiple alleles can be evaluated for immunogenicity both in vitro and in vivo. Furthermore, such peptides can be analyzed for the simultaneous inclusion of hTERT-specific T helper cell epitopes restricted to MHC Class II, as has been done for other CTL antigens such as hepatitis B nucleocapsid (Ferrari et al., J. Clin. Invest. 88:214-222, 19911). A short polypeptide containing multiple hTERT-specific Class I and Class II epitopes would be inordinately useful in the design of hTERT-specific immunotherapies.

Evaluation of hTERT-Specific CTL Generation from the Peripheral Blood of Cancer Patients Compared with Normal Donors Prevailing hypotheses emphasize the relative inadequacy of the immune system in cancer patients. Thus, prior to the present invention it was not clear whether vaccination with tumor antigens, for example, can consistently trigger clinically effective CTL in the tumor-bearing patient. Likewise, the ability to generate antigen-specific CTL ex vivo may be compromised when precursor cells for CTL expansion are obtained from cancer patients.

Cancer patients were HLA-typed and underwent leukopheresis to obtain sufficient numbers of peripheral blood mononuclear cells (PBMC). A hTERT peptide (K973 KLFGVLRLK; SEQ ID NO:2) was used to generate specific CTL from CD8-purified cells based on the same DC/CD40-activated B cell system described above.

Figure 6:
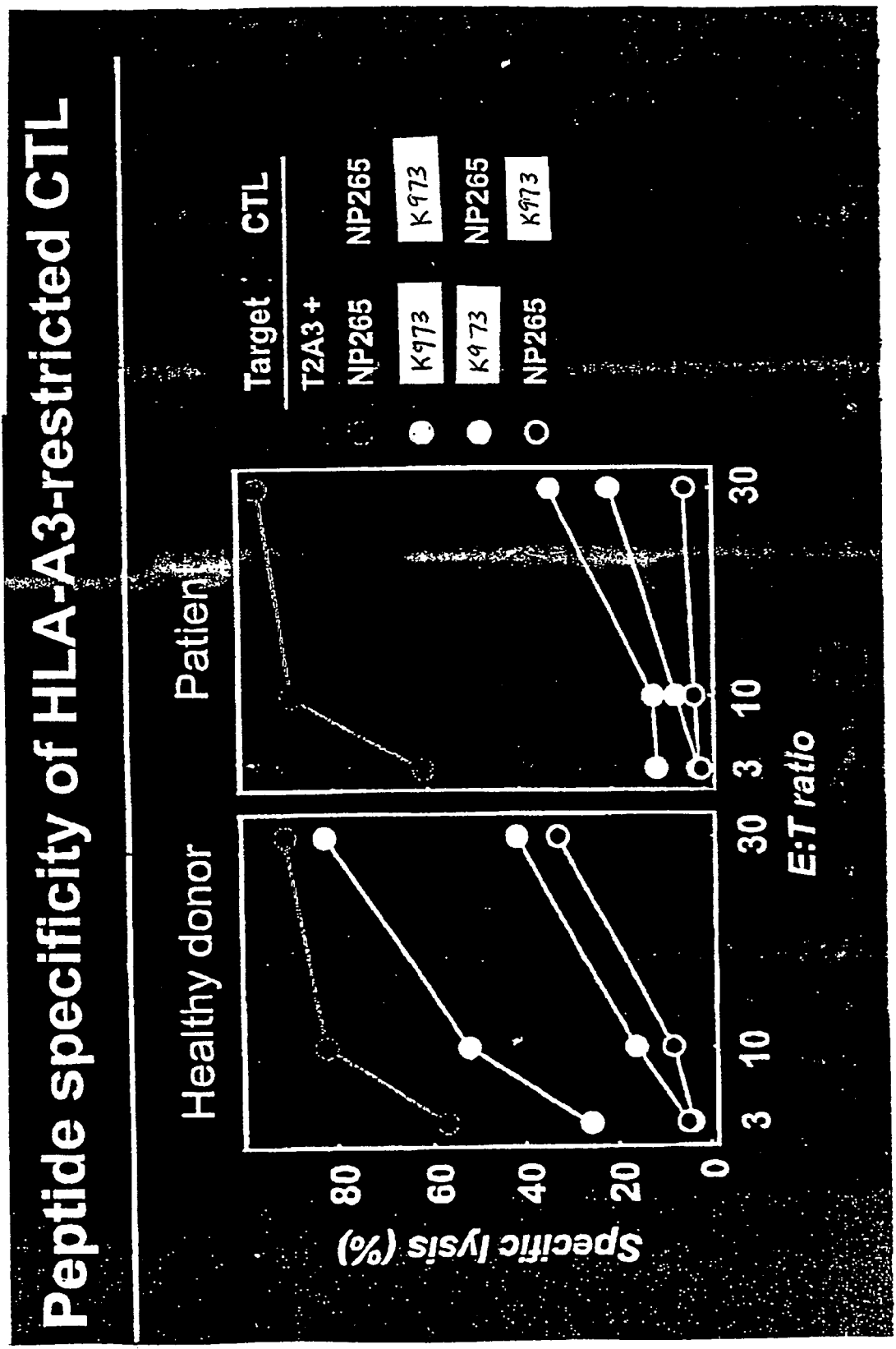
FIG. 6 are graphs showing peptide specificity of HLA-A3 restricted CTL.
Figure 7:
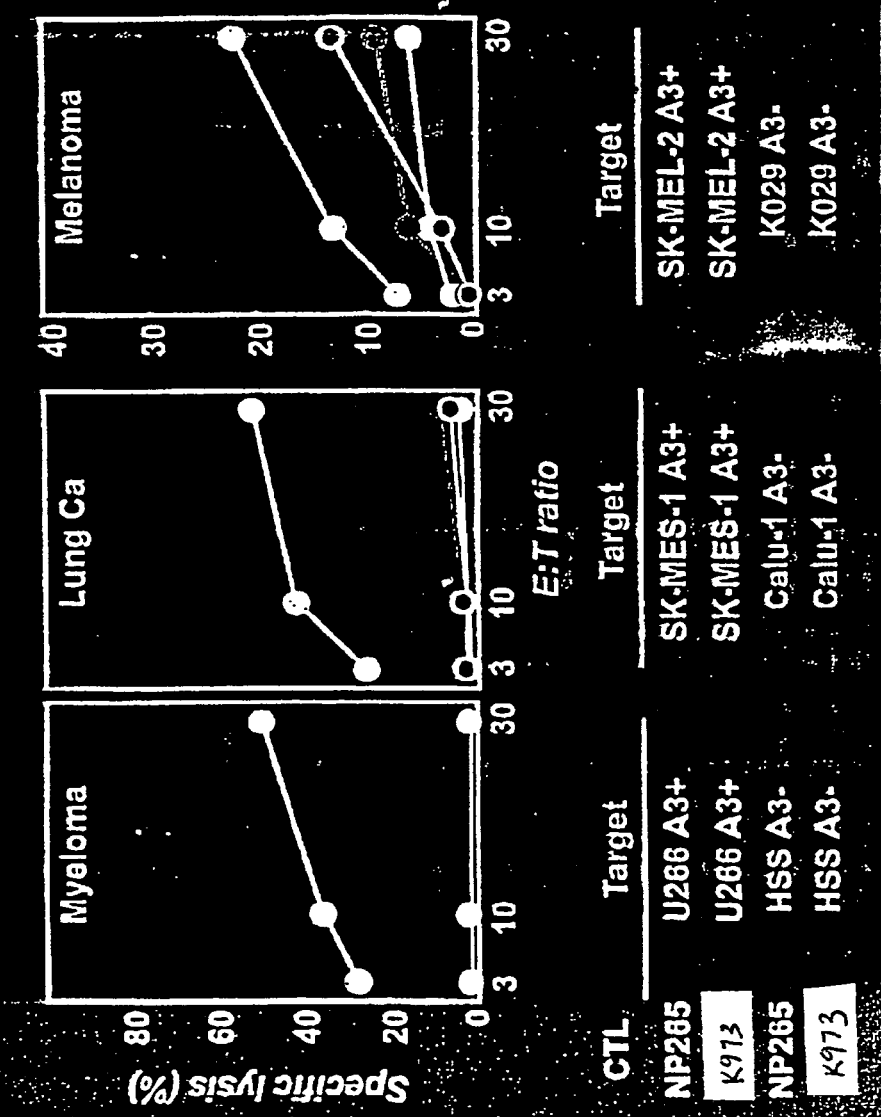
FIG. 7 are graphs showing that K973 CTL kill hTERT$^+$ tumors in an HLA-A3-restricted fashion.
Figure 8:
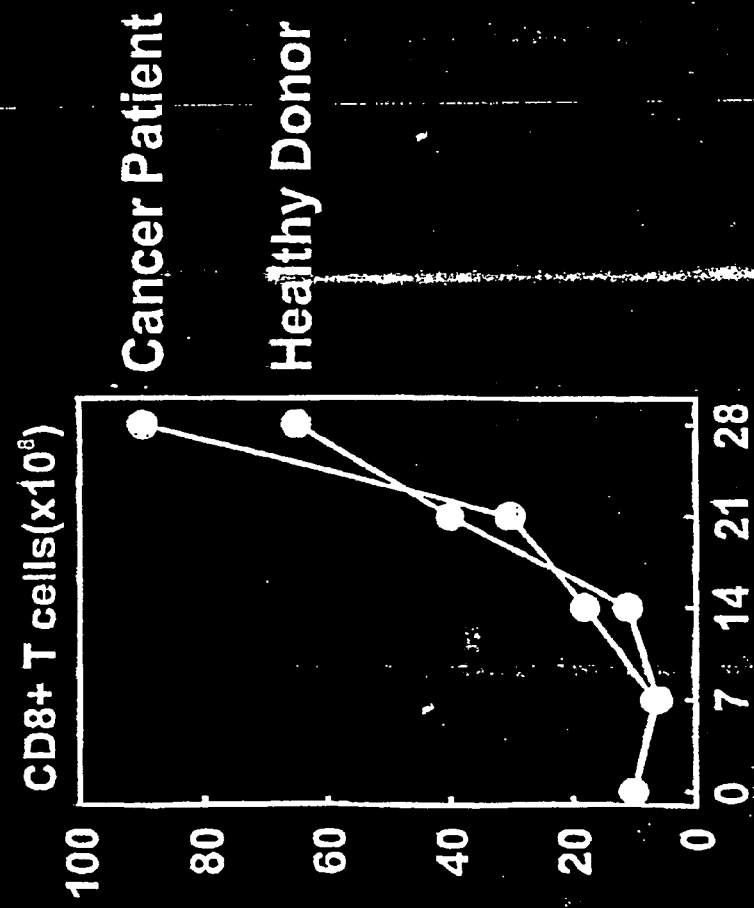
FIG. 8 is a graph showing ex vivo expansion of I540 CTL from a cancer patient and a healthy donor.

The hTERT-derived peptide K973 (KLFGVLRLK; SEQ ID NO:2) was used to generate K973-specific CTL from a healthy donor and a melanoma patient. Cytotoxicity against peptide pulsed T2 cells transduced with the HLA-A3 gene (T2A3) were used to demonstrate K973 killing, as compared to a NP265 (influenza)-specific CTL from the same donors (FIG. 6). The K973-specific CTL from patient blood killed hTERT$^+$ tumors from multiple histologies, in an HLA-A3 restricted fashion, demonstrating that K973 hTERT peptide is naturally processed and presented by tumor cells (FIG. 7). Also, expansion of hTERT (I540)-specific CTL from patients is as efficient as expansion from normal donors (FIG. 8).

CTL clones can also be obtained from patients specific for hTERT and generation of such clones compared to generation of clones from normal donors. The efficiency of expanding precursor CTL cells as clones are compared to that of expanding bulk CTL cultures containing specific cells. Clones are generated similarly to methods previously described (Brodie et al., Nat. Med. 5:34-58, 1999). CD8$^+$ cells are isolated, primed with peptide-pulsed autologous DC, and re-stimulated once with peptide-pulsed CD40-activated B cells. Culture aliquots are replated at limiting dilution (0.5 to 3 cells/well) with IL2 and irradiated allogeneic PBMC in 96-well plates previously incubated with anti-CD3 mAb. After 14 days, growing colonies are expanded using IL2, anti-CD3 mAb, and irradiated allogeneic PBMC, and tested for hTERT specificity. Expansion efficiency of clones is compared to expansion of bulk CTL cultures. Antigen-specificity of clones is evaluated using the cytotoxic and cytokines studies described above. Finally, expansion efficiency and antigen reactivity of patient-derived clones is compared to that of clones from normal donors.

We have also demonstrated I540-specific CTL from normal donors and patients, using tetramer technology (see above; FIG. 9). CTL lines were stained with tetramers specific for the I540 peptide, showing that between 1% and 4% of CD8$^+$ cells are telomerase specific. Tetramers specific for an irrelevant HLA-A2 binding peptide, JS34, was used as a negative control. The frequency of telomerase specific cells in peripheral blood is less than the limit of tetramer detection for both normal donors and patients.

II. Use of Universal Tumor Associated Antigens in Therapeutic Methods

As is discussed above, the invention provides methods for identifying universal tumor associated antigens (TAAs) that contain peptides that bind to MHC and are recognized by cytotoxic T lymphocytes in an MHC-restricted fashion. These antigens, and in particular the MHC-binding peptides within them, as well as nucleic acid molecules that encode the antigens and peptides, can be used in a variety of methods for preventing or treating conditions associated with excessive cell proliferation and expression of a universal TAA, such as cancer.

Examples of conditions that can be prevented or treated using the methods of the invention, include, for example, all cancers, e.g., melanoma, lymphoma, carcinoma, sarcoma, multiple myeloma, leukemia, lung cancer, ovarian cancer, uterine cancer, cervical cancer, prostate cancer, liver cancer, colon cancer, pancreatic cancer, and brain cancer. Pre-cancerous and non-cancerous conditions characterized by excessive cell proliferation, and expression of a universal tumor associated antigen, can be treated using the methods of the invention as well. For example, all carcinomas in situ, e.g., ductal carcinoma in situ, lobular carcinoma in situ, and cervical carcinoma in situ, as well as adenoma and benign polyps can be treated using the methods of the invention.

Patients that can be treated using the methods of the invention include those whose conditions are at early, intermediate, or advanced stages of development. Patients can receive treatment according to the invention before, during, or after other types of treatment, such as chemotherapy, radiation, or surgery, or can receive the treatment of the invention in the absence of any other type of treatment. The methods of the invention can also be used as general prophylactic measures; to prevent conditions from arising in patients that are at risk, or have early signs, of developing a condition associated with excessive cellular proliferation, such as cancer, or to prevent recurrence of such a condition. Additional persons that can be treated, in particular, using vaccination methods of the invention (see below), are those who are to donate cells, such as cytotoxic T lymphocytes, for use in the treatment of another (see below).

Central to the prophylactic and therapeutic methods of the invention is the pathway of cell-mediated immunity involving cytotoxic T lymphocytes (CTLs). In this pathway, an antigen is taken up and processed by an antigen presenting cell, so that a peptide of the antigen is presented on the surface of the cell, in the context of MHC. Such antigen presenting cells then activate cytotoxic T lymphocytes, in an MHC-restricted fashion, to proliferate and kill target cells that express the antigen.

The prophylactic and therapeutic methods of the invention intervene in this pathway at different levels. For example, in one of these methods, an antigen is administered to a patient, in whom the antigen is taken up by antigen presenting cells, which in turn activate CTLs. In another of these methods, an antigen presenting cell is contacted with an antigen ex vivo, where it takes up, processes, and presents the antigen, in the context of MHC. Such ex vivo stimulated APCs are then administered to a patient, in whom they specifically activate CTLs. In yet another of these methods, CTLs are activated ex vivo with APCs presenting tumor associated antigen peptides, and the activated CTLs are then administered to a patient. These methods, each of which includes numerous variations, are described in further detail below.

As is noted above, the prophylactic and therapeutic methods of the invention include one in which a universal TAA, or a fragment thereof that binds to MHC, is administered to a patient, in whom the antigen or fragment is taken up by and processed within an antigen presenting cell, which in turn activates a cytotoxic T cell in the patient. This vaccination method can be carried out using one or more universal TAAs (e.g., hTERT), one or more MHC-binding peptides of a single TAA, one or more MHC-binding peptides of more than one universal TAA, or a combination thereof. Optionally, the antigen can be administered in combination with an adjuvant to enhance the anti-TAA immune response, or the antigen can be packaged into a delivery system (see below).

Any reagent including a universal TAA (e.g., hTERT) or MHC-binding peptide thereof can be used for vaccination. These include, without limitation, full length universal TAA, MHC-binding fragments of universal TAAs, as well as fusion proteins including universal TAAs and MHC-binding fragments thereof. Peptides or polypeptides including TAA peptides and polypeptides can include 8, 9, 10, 11, 12, or more amino acid stretches having sequence identity with a region of a reference TAA, such as hTERT. For example, the peptides can include nine amino acid stretches, in which seven, eight, or all nine of the amino acids in the TAA peptide nine amino acid sequence are identical to a region of nine amino acids in TAA. In addition, in the case of hTERT, a TAA peptide or polypeptide can include up to 1132 amino acids that are identical to an amino acid sequence found in hTERT, for example, 9-20, 20-40, 40-80, 80-200, 200-500, 500-1131, or 1131-1132 amino acids that are identical to an amino acid sequence found in hTERT. Polypeptides containing TAA (e.g., hTERT) peptides can contain additional amino acid stretches that do not correspond to the amino acid sequence of the TAA.

To vaccinate a patient to elicit a universal TAA (e.g., hTERT)-specific immune response in the patient, it is necessary to obtain large amounts of the universal TAA protein or peptide, and this can be accomplished by numerous standard methods, for example, chemical synthesis (e.g., Fmoc methods (Sigma Genosys); see above) or expression in eukaryotic or prokaryotic cells. (These methods can also be used to produce universal TAAs or MHC-binding peptides thereof for use in pulsing antigen presenting cells; see below.)

Recombinant TAA peptides, such as hTERT peptides, can be overexpressed in vivo by introducing coding sequences of the peptide into various types of cells, or in vitro, using cell-free expression systems that are known in the art. The peptide products can then purified for generating TAA-specific CTLs ex vivo and for vaccine production. Purified TAA peptides are also useful for diagnostic assays that measure the presence of TAA-specific CTLs in a test sample. For example, the presence (or increased levels) of TAA-specific CTLs in a sample from a subject who has received an anti-TAA vaccination, relative to the level of TAA-specific CTLs in a reference sample (such as a pre-vaccination sample from the patient), indicates that the patient has mounted a TAA-specific immune response.

TAA peptides, such as hTERT peptides, can be produced by chemical synthesis (e.g., by the methods described in *Solid Phase Peptide Synthesis,* 2nd ed., 1984, The Pierce Chemical Co., Rockford, Ill., or by other methods known to those skilled in the art of peptide synthesis).

A wide variety of expression systems can be used to produce recombinant TAA peptides, polypeptides, fragments, fusion proteins, and amino acid sequence variants. TAA peptides can be produced in prokaryotic hosts (e.g., *E. coli*) or in eukaryotic hosts (e.g., *S. cerevisiae*, insect cells, such as Sf9 cells, or mammalian cells, such as COS-1, NIH 3T3, or HeLa cells). These cells are commercially available from, for example, the American Type Culture Collection, Rockville, Md. (also see, e.g., Ausubel et al., *Current Protocols in Molecular Biology*, John Wiley & Sons, New York, N.Y., 1998). The method of transformation and the choice of expression vehicle (e.g., expression vector) depends on the host system selected. Transformation and transfection methods are described, e.g., by Ausubel et al., supra, and expression vehicles can be chosen from the numerous examples that are known in this field.

First, a nucleic acid molecule encoding a TAA peptide, such as an hTERT peptide, is introduced into a plasmid or other vector, which is then used to transform living cells. Constructs in which a cDNA containing the entire TAA coding sequence, a fragment of the TAA coding sequence, amino acid variations of the TAA coding sequence, or fusion proteins of the aforementioned, inserted in the correct orientation into an expression plasmid, can be used for protein expression. Prokaryotic and eukaryotic expression systems allow various immunogenic domains of TAA peptides or polypeptides to be recovered as fusion proteins, and then used for the generation of TAA-specific CTLs. In some cases, for example, when a TAA peptide is to be expressed directly within a patient's cells, it may be desirable to express the TAA peptide under the control of an inducible or tissue-specific promoter.

Typical expression vectors contain promoters that direct the synthesis of large amounts of mRNA corresponding to the inserted TAA peptide-encoding nucleic acid molecule in the plasmid-bearing cells. They can also include eukaryotic or prokaryotic "origin of replication" sequences, which allow for their autonomous replication within the host organism, sequences that encode genetic traits that allow vector-containing cells to be selected in the presence of otherwise toxic drugs (such as antibiotics), and sequences that increase the efficiency with which the synthesized mRNA is translated. Stable, long-term vectors can be maintained as freely replicating entities within cells by using regulatory elements of, for example, viruses (e.g., the OriP sequences from the Epstein Barr Virus genome). Cell lines can also be produced that have the vector integrated into genomic DNA, and, in this manner, the gene product is produced on a continuous basis.

Expression of foreign sequences in bacteria such as *Escherichia coli* requires insertion of a nucleic acid molecule encoding a polypeptide into a bacterial expression vector. Plasmid vectors in this category contain several elements required for propagation of the plasmid in bacteria and expression of inserted DNA of the plasmid by the plasmid-carrying bacteria. Propagation of only plasmid-bearing bacteria is achieved by introducing into the plasmid selectable marker-encoding sequences that allow plasmid-bearing bacteria to grow in the presence of otherwise toxic drugs (e.g., antibiotics). The plasmid also includes a transcriptional promoter that capable of producing large amounts of mRNA from the cloned gene. Such promoters may or may not be inducible promoters. The plasmid also, preferably, contains a polylinker to simplify insertion of the gene in the correct orientation within the vector. For example, in a simple *E. coli* expression vector utilizing the lac promoter, the expression vector plasmid contains a fragment of the *E. coli* chromosome containing the lac promoter and the neighboring lacZ gene. In the presence of the lactose analog IPTG, RNA polymerase normally transcribes the lacZ gene, producing lacZ mRNA, which is translated into the encoded protein, β-galactosidase. The lacZ gene can be cut out of the expression vector with restriction endonucleases and replaced by a TAA (e.g., hTERT) peptide gene sequence, or a fragment, fusion, or mutant thereof. When the resulting plasmid is transfected into *E. coli*, addition of IPTG and subsequent transcription from the lac promoter produces mRNA encoding the polypeptide of interest, which is then translated into a polypeptide.

Once the appropriate expression vector containing a TAA (e.g., hTERT) gene is constructed, it is introduced into an appropriate host cell by transformation, transfection, or transduction techniques that are known in the art, including calcium chloride transformation, calcium phosphate transfection, DEAE-dextran transfection, electroporation, microinjection, protoplast fusion, and liposome-mediated transfection. The host cells that are transformed with the vectors of this invention can include (but are not limited to) *E. coli* or other bacteria, yeast, fungi, insect cells (using, for example, baculoviral vectors for expression), human, mouse, or other animal cells. Mammalian cells can also be used to express TAA peptides using a vaccinia virus expression system, as is described by Ausubel et al., supra.

In vitro expression of TAA (e.g., hTERT) peptides, proteins, fusions, polypeptide fragments, or mutated versions thereof encoded by cloned DNA is also possible using the T7 late promoter expression system. Plasmid vectors containing late promoters and the corresponding RNA polymerases from related bacteriophages such as T3, T5, and SP6 can also be used for in vitro production of proteins from cloned DNA. *E. coli* can also be used for expression using an M13 phage such as mGPI-2. Furthermore, vectors that contain phage lambda regulatory sequences, or vectors that direct the expression of fusion proteins, for example, a maltose-binding protein fusion protein or a glutathione-S-transferase fusion protein, also can be used for expression in *E. coli*.

Eukaryotic expression systems permit appropriate post-translational modifications to expressed proteins. Transient transfection of a eukaryotic expression plasmid allows the transient production of TAA peptides by a transfected host cell. TAA peptides can also be produced by a stably-transfected mammalian cell line. A number of vectors suitable for stable transfection of mammalian cells are available to the public (e.g.; see Pouwels et al., *Cloning Vectors: A Laboratory Manual*, 1985, Supp. 1987), as are methods for constructing such cell lines (see, e.g., Ausubel et al., supra). In one example, cDNA encoding a TAA (e.g., hTERT) peptide, protein, fragment, mutant, or fusion protein is cloned into an expression vector that includes the dihydrofolate reductase (DHFR) gene. Integration of the plasmid and, therefore, integration of the TAA peptide-encoding gene into the host cell chromosome is selected by inclusion of 0.01-300 µM methotrexate in the cell culture medium (as is described by Ausubel et al., supra). This dominant selection can be accomplished in most cell types. Recombinant protein expression can be increased by DHFR-mediated amplification of the transfected gene. Methods for selecting cell lines bearing gene amplifications are described by Ausubel et al., supra. These methods generally involve extended culture in medium containing gradually increasing levels of methotrexate. The most commonly used DHFR-containing expression vectors are pCVSEII-DHFR and pAdD26SV(A) (described by Ausubel et al., supra. The host cells described above or, preferably, a DHFR-deficient CHO cell line (e.g., CHO DHFR$^-$ cells, ATCC Accession No. CRL 9096) are among those most preferred for DHFR selection of a stably-transfected cell line or DHFR-mediated gene amplification. Other drug markers can be analogously used.

Expression of proteins, such as those containing TAA (e.g., hTERT) peptides, in eukaryotic cells allows the production of large amounts of normal or mutant proteins for isolation and purification, and the use of cells expressing a TAA peptide-containing protein provides a functional assay system for antibodies generated against the TAA peptide of interest.

Another preferred eukaryotic expression system is the baculovirus system using, for example, the vector pBacPAK9, which is available from Clontech (Palo Alto, Calif.). If desired, this system can be used in conjunction with other protein expression techniques, for example, the myc tag approach described by Evan et al. (Mol. Cell. Biol. 5:3610-3616, 1985).

Once a recombinant protein is expressed, it can be isolated from the expressing cells by cell lysis followed by protein purification techniques, such as affinity chromatography. In this example, an anti-TAA peptide antibody, which can be produced by methods that are well-known in the art, can be attached to a column and used to isolate recombinant TAA peptide-containing proteins. Lysis and fractionation of TAA peptide-harboring cells prior to affinity chromatography can be performed by standard methods (see, e.g., Ausubel et al., supra). Once isolated, the recombinant protein can, if desired, be purified further, e.g., by high performance liquid chromatography (HPLC; e.g., see Fisher, *Laboratory Techniques in Biochemistry and Molecular Biology*, Work and Burdon, Eds., Elsevier, 1980).

Preferably, the universal TAA antigen or MHC-binding peptide thereof is administered to a patient in association with an adjuvant. For example, a chemical antigen (e.g., Freund's incomplete adjuvant cytoxan; an aluminum compound, such as aluminum hydroxide, aluminum phosphate, or aluminum hydroxyphosphate; liposomes; ISCOMS; microspheres; protein chochleates; vesicles consisting of nonionic surfactants; cationic amphiphilic dispersions in water, oil/water emulsions; muramidyldipeptide (MDP) and its derivatives such as glucosyl muramidyldipeptide (GMDP), threonyl-MDP, murametide and murapalmitin; and QuilA and its subfractions; as well as various other compounds such as monophosphoryl-lipid A (MPLA); gamma-inulin; calcitriol; and loxoribine) can be used.

A biological response modifier, which is a soluble mediator that affects induction of an immune response, can also be used as an adjuvant. For example, cytokines (e.g., IL-2 and GM-CSF), chemokines, co-stimulatory molecules (e.g., B7, ICAM, class I monoclonal antibodies, stem cell factor, and stimulated T cells) can be used. Also, bacterial products, such as toxins or, preferably, subunits or fragments thereof that have reduced (if any) toxicity, but maintained adjuvant activity.

Additional types of adjuvant molecules that can be used in the invention include, for example, biological modifiers of the death response (e.g., apoptosis sensitizers) and compounds or treatment that increases the susceptibility of the target cell to treatment, such as radiation and chemotherapy. Also, increasing expression of the universal TAA in the cell can increase susceptibility of the cell to treatment according to the invention.

Finally, cellular adjuvants can be used in the immunization methods of the invention. For example, a universal TAA peptide can be administered to a patient on the surface of an antigen presenting cell, in the context of MHC. In additional to professional antigen presenting cells, e.g., dendritic cells, CD40-activated B cells, irradiated tumor cells (e.g., in association with GM-CSF), alternative antigen presenting cells, synthetic antigen presenting cells (e.g., lipid mycels and artificial APC-like scaffolds), and fusions of any of the above-listed cells can be used.

As an alternative to vaccination with a universal TAA protein or peptide, vaccination with a nucleic acid molecule that encodes such a protein or peptide can be used for vaccination. Such nucleic acid molecules can be administered as "naked" DNA molecules, present in a plasmid or viral vector, or packaged into a liposome or cell, such as eukaryotic cell, prior to administration. The nucleic acid molecules can be administered to a patient in vivo, or can be used to treat a cell ex vivo (e.g., an antigen presenting cell, such as a dendritic cell or a CD40-activated B cell), which is then administered to the patient. Alternatively, RNA, e.g., mRNA, can be used in these methods (see, e.g., Boczkowski et al., J. Exp. Med. 184:465-472, 1996; J. Exp. Med. 186:1177-1182, 1997).

For in vivo expression, a gene that encodes a polypeptide that includes a TAA or an MHC-binding peptide thereof must be delivered to cells in a form that can be taken up by the cells, in which a sufficient level of protein is expressed to induce an effective immune response. Retroviral, adenoviral, lentiviral, poxyiral, and other viral vectors are suited as nucleic acid expression vectors for in vivo delivery, because they show efficient infection and/or integration and expression; see, e.g., Cayouette et al., Hum. Gene Therapy, 8:423-430, 1997; Kido et al., Curr. Eye Res. 15:833-844, 1996; Bloomer et al., J. Virol. 71:6641-6649, 1997; Naldini et al., Science 272:263-267, 1996; Miyoshi et al., Proc. Nat. Acad. Sci., U.S.A., 94:10319-1032, 1997; *Vaccines: New Approaches to Immunological Problems*, R. W. Ellis (Ed.), Butterworth-Heinemann, Boston. For example, any DNA fragment that encodes a polypeptide that contains a TAA peptide can be cloned into a retroviral vector and transcribed via its endogenous promoter, via an exogenous promoter, via a promoter specific for the target cell type of interest, or, in the case of retroviral vectors, via the retroviral long terminal repeat. Other viral vectors that can be used include adenovirus, adeno-associated virus, poxviruses, such as vaccinia virus or bovine papilloma virus, or a herpes virus, such as Epstein-Barr Virus.

Gene transfer in vivo can also be achieved by non-viral means. For example, a plasmid vector that encodes a polypeptide that contains a TAA (e.g., hTERT) peptide can be injected directly into skeletal muscle or cardiac muscle by previously described methods (e.g., Wolff et al., Science, 247:1465-1468, 1990). Expression vectors injected into skeletal muscle in situ are taken up into muscle cell nuclei and used as templates for expression of their encoded proteins. TAA peptide-encoding genes that are engineered to contain a signal peptide are secreted from TAA peptide-expressing muscle cells, after which they induce an immune response. Gene transfer into cells within the tissues of a living animal also can be achieved by lipofection (Feigner et al., Proc. Natl. Acad. Sci. USA 84:7413, 1987; Ono et al., Neurosci. Lett. 117:259, 1990; Brigham et al., Am. J. Med. Sci. 298:278, 1989; Staubinger et al., Meth. Enz. 101:512, 1983), or asialoorosomucoid-polylysine conjugation (Wu et al., J. Biol. Chem. 263:14621, 1988; Wu et al., J. Biol. Chem. 264:16985, 1989), and analogous methods.

Retroviral vectors, adenoviral vectors, adenovirus-associated viral vectors, or other viral vectors also can be used to deliver genes encoding TAA (e.g., hTERT) peptides or polypeptides to cells ex vivo. Numerous vectors useful for this purpose are generally known (see, e.g., Miller, Human Gene Therapy 15-14, 1990; Friedman, Science 244:1275-1281, 1989; Eglitis et al., BioTechniques 6:608-614, 1988; Tolstoshev et al., Curr. Opin. Biotech. 1:55-61, 1990; Sharp, The Lancet 337:1277-1278, 1991; Cornetta et al., Nucl. Acid Res. and Mol. Biol. 36:311-322, 1987; Anderson, Science 226: 401-409, 1984; Moen, Blood Cells 17:407-416, 1991; Miller et al., Biotech. 7:980-990, 1989; Le Gal La Salle et al., Science 259:988-990, 1993; and Johnson, Chest 107:77 S-83S, 1995). Retroviral vectors are particularly well developed and have been used in clinical settings (Rosenberg et al., N. Engl. J. Med 323:370, 1990; Anderson et al., U.S. Pat. No. 5,399,346).

Gene transfer into cells ex vivo can also be achieved by delivery of non-viral vectors, such as expression plasmids, using methods such as calcium phosphate or DEAE dextran transfection, electroporation, and protoplast fusion. Liposomes can also be potentially beneficial for delivery of DNA into a cell.

Cells that are to be transduced or transfected ex vivo can be obtained from a patient (e.g., peripheral blood cells, such as B cells or dendritic cells, bone marrow stem cells, or cells from a tumor biopsy) prior to transfection, and re-introduced after transfection. However, the cells also can be derived from a source other than the patient undergoing gene transfer.

In the constructs described above, TAA peptide expression can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in skeletal muscle cells can be used to direct TAA peptide expression for vaccination in situ. The enhancers used can include, without limitation, those that are characterized as tissue- or cell-specific in their expression.

Conventional pharmaceutical practice can be employed to provide suitable formulations or compositions to administer TAA hTERT) peptide or nucleic acid vaccinations for treatment of, or prophylaxis against, cancer. TAA peptides, TAA polypeptides, and TAA nucleic acid molecules can be administered within a pharmaceutically-acceptable diluent, carrier, or excipient, in unit dosage form. Administration can begin before a patient is symptomatic. Any appropriate route of administration can be employed, for example, administration can be parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration. Therapeutic formulations can be in the form of liquid solutions or suspensions; for oral administration, formulations can be in the form of tablets or capsules; and for intranasal formulations, in the form of powders, nasal drops, or aerosols. An adjuvant, e.g., as listed above, can be included with the formulation.

Methods well known in the art for making formulations are found, for example, in *Remington's Pharmaceutical Sciences*, (18th edition), ed. A. Gennaro, 1990, Mack Publishing Company, Easton, Pa. Formulations for parenteral administration can, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers can be used to control the release of the compounds. Other potentially useful parenteral delivery systems for TAA peptides, polypeptides, and TAA nucleic acids include ethylene-vinyl acetate copolymer particles, osmotic pumps, implantable infusion systems, and liposomes. Formulations for inhalation can contain excipients, for example, lactose, or can be aqueous solutions containing, for example, polyoxyethylene-9-lauryl ether, glycocholate and deoxycholate, or can be oily solutions for administration in the form of nasal drops, or as a gel.

As is mentioned above, in addition to the vaccination methods described above, which result in the activation of antigen-specific, MHC-restricted CTLs in vivo, such cells (i.e., antigen-specific, MHC-restricted CTLs) can be generated in vitro, and then administered to patients. Any cell that expresses an endogenous or exogenously-introduced major histocompatibility antigen-encoding gene can be used to present a TAA (e.g., hTERT) peptide to generate TAA-specific CTLs in vitro. In one variation of this approach, a peptide-presenting cell expresses an endogenously or exogenously-introduced TAA polypeptide-encoding gene. Expression of endogenous TAA in antigen-presenting cells can be stimulated as described in Schultze et al., supra, by cytokines, such as IL-2, or by other molecules that are known to those of skill in this art to stimulate TAA expression. In another variation, the antigen presenting cells are pulsed with the universal TAA or MHC-binding peptide thereof, and the pulsed cells are then used to generate CTLs for administration to a patient. Preferably, the CTLs used in these methods are obtained from the patient to whom they are to ultimately be administered (i.e., the cells are autologous). As is described above, we have demonstrated that such cells can be obtained from cancer patients for use in this manner. Alternatively, donor cells (i.e., allogeneic cells) can be used in this method.

Finally, methods in which any of the above-described immunotherapeutic approaches are combined are included in the invention. For example, a patient may be treated with an ex vivo, TAA (e.g., hTERT)-activated CTL and/or an ex vivo, TAA (e.g., hTERT)-pulsed APC (e.g., a DC or CD40-activated B cell), and this treatment can be carried out before, during, or after a vaccination approach (see above). In addition to combining the approaches, each approach (or a combination thereof) can employ multiple peptides of a universal TAA (e.g., hTERT), peptides of multiple TAAs, or a combination thereof.

III. Measurement of TAA-Specific CTL Levels in Patients, CTL Donors, and TAA-Specific CTL Reparations Generated Ex Vivo Patients who have one or more tumors containing TAA-expressing tumor cells and patients who are at risk for developing such tumors can be vaccinated with compositions containing one or more TAA peptides, TAA polypeptides, TAA nucleic acid molecules, cells presenting a TAA peptide, or mixtures thereof. Subjects to be used as donors of TAA-specific CTLs for transfer into patients can be similarly vaccinated. Levels of TAA-specific CTLs that result from TAA-specific vaccination of patients or other subjects, or ex vivo generation of TAA specific CTLs, can be monitored using well-known methods. An increase in the level of TAA-specific CTLs in a test sample from a vaccinated subject or a CTL culture stimulated with TAA ex vivo, relative to a reference sample (e.g., a pre-vaccination or pre-stimulation sample), indicates that a TAA-specific CTL response has been stimulated in a vaccinated subject or TAA-stimulated CTL culture. Preferably the increase is by at least 50%, more preferably, at least 100%, still more preferably, at least 200%, and most preferably, at least 400%. In addition, the efficacy of non-antigen-specific immunotherapies (e.g., administration of IL-2 or interferon) against tumors containing TAA-expressing cells can be monitored using similar approaches.

Levels of TAA-specific CTLs can also be assessed in naive subjects who have not received TAA vaccinations or other treatment for the purpose of generating TAA-specific CTLs. Since some types of tumors (e.g., malignant melanoma, renal cell carcinoma, and non-Hodgkin's lymphoma) themselves elicit immune responses in their hosts, an increase in the level of TAA-specific CTLs cells in a patient sample, compared to the level in a reference sample from a normal subject who does not have a tumor, or in a reference sample that was previously obtained from the patient, can indicate the development of a tumor in a patient not known to have a tumor or an increase in tumor burden (e.g., increased tumor size, or the development or increase in metastatic tumors) in a patient known to have a tumor.

One approach by which the level of TAA-specific CTLs can be measured is using standard cytotoxicity assays, such as the $Cr^{51}$ release assay (Schultze et al., J. Clin. Invest. 100: 2757, 1997), which is described above, and also further below. Another approach for measuring the level of TAA-specific CTLs involves measuring the binding of peptide-specific CTLs to a tetrameric peptide/MHC complex in vitro, as is described by Altman et al. (Science 274:94-96, 1996). Briefly, a fusion protein containing an HLA heavy chain molecule, such as HLA-A*0201, plus a peptide that is a substrate for biotinylation at the C-terminus of the HLA polypeptide, is produced. The fusion protein is folded in vitro in the presence β2-microglobulin and a TAA peptide ligand. The purified MHC/TAA peptide complexes are then biotinylated at the C-terminus of the HLA heavy chain, and tetramers are produced by mixing the biotinylated MHC/TAA peptide complexes with phycoerythrin-labeled deglycosylated avidin at a molar ratio of 4:1. Samples that contain CTLs (such as blood samples or ex vivo cultures) are mixed with the TAA peptide/MHC tetrameric complexes and the relative amount of TAA-specific CTLs that bind to the TAA peptide/MHC tetrameric complexes can be measured for each sample by flow cytometry, using methods described by Altman et al., supra, and by other methods known to those of skill in this art. Another method that can be used is ELISPOT, which is described in detail above.

Characterization of one universal TAA identified using the methods described above, hTERT, is described as follows.

It is important to evaluate patients treated with hTERT-specific immunotherapies for evidence of immune responses. From patients in a Phase I adoptive T cell trial, the goals are to (1) evaluate patient peripheral blood before and after treatment for direct evidence of hTERT-specific CTL, and (2) evaluate CTL for functional hTERT-reactivity in cytotoxic and cytokine-release assays.

Direct evaluation of hTERT-specific CTL can be accomplished by using hTERT peptide-MHC class I "tetramers" suitable for flow cytometry. Tetramers of the I540 hTERT peptide with HLA-A*0201 are generated according to published methods (Altman et al., Science 274:94-96, 1996). Using hTERT tetramers, patient peripheral blood or available tumor suspensions can be assessed for the presence of hTERT-specific CD8 cells before, during, and after treatment. Although it is expected that prior to treatment, the percentage of hTERT-reactive T cells will be low or zero, the tetramer technology has revealed a surprising high percentage of reactive T cells in sensitized individuals, although mostly to viral antigens such as EBV (Callan et al., J. Exp. Med. 187:1395-1402, 1998). Direct identification of hTERT-specific CTL after infusion allows (1) determination of the circulating time span of infused cells in the peripheral blood, (2) refinement of the T cell dose used for infusion, and (3) evaluation of hTERT-specific infiltration in tumor tissue (similar to the recent evaluation of gag-specific adoptive T cell infiltration in HIV patient lymph nodes) (Brodie et al., Nat. Med. 3:1271, 1999). Tetramer technology abrogates the need for genetic marking of cells prior to infusion, which has complicated other studies of antigen-specific adoptive immunotherapy (Riddell et al., Nat. Med. 2:216-223, 1996).

Immune responses can also be measured functionally using patient peripheral blood in vitro assays for cytotoxicity and cytokine elaboration. If tetramer generation is successful, FACS sorting techniques based on these tetramers are used to isolate hTERT-specific T cells, thereby facilitating their ex vivo re-expansion for cytotoxicity and cytokine studies. If not successful, unsorted peripheral blood from patients can be used. In particular, patient T cells are tested in standard chromium release assays and their culture supernatants are for INFy and/or TNF elaboration, according to standard methods (Schultze et al., J. Clin. Invest. 100:2757-2765, 1997). In some studies, cytokine elaboration of specific CTL has a greater correlation with clinical effect than cytotoxicity assays (see, e.g., Aruga et al., Cancer Immunol. Immunother. 41:317-324, 1995). With appropriate protocols in place, patient-derived T cells pre- and post-treatment are obtained from peripheral blood as well as surgical and biopsy samples.

When available, tumor samples from patients are evaluated for hTERT expression and telomerase activity before, during, and after treatment; however, given that most primary tumors in nearly all cancers are telomerase-positive, demonstration of telomerase activity in the tumors of candidate patients is not an eligibility requirement in the Phase I trial. It is important to monitor whether immunotherapy leads to telomerase downregulation and/or antigen loss that limits clinical efficacy. Telomerase activity from frozen samples are measured by TRAP assay, and the presence of hTERT mRNA is measured using RNAse protection assays. In addition, tumor samples could also be evaluated for hTERT expression using an hTERT-specific antisera or monoclonal antibody suitable for Western blotting or, ideally, intracytoplasmic flow cytometry. In preliminary work, the sequence of hTERT has been analyzed for candidate peptides potential useful for immunization and screening. Four 15mer peptides have been selected for immunization of mice based on the following characteristics: (1) their lack of homology with mouse TERT, (2) high degree of hydrophilicity, and (3) flexibility and β-turn characteristics predicted by a computer-assisted analysis (Genosys Biotechnologies). Pending synthesis of these peptides and conjugation to KLH and OVA (Genosys Biotechnologies), immunization, screening, and hybridoma generation is carried out at the Dana-Farber Cancer Institute Hybridoma Core Facility. The immunogenic hTERT peptides are used in rabbits.

OTHER EMBODIMENTS

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications, and this application is intended to cover any variations, uses, or adaptations of the invention following, in general, the principles of the invention and including such departures from the present disclosure come within known or customary practice within the art to which the invention pertains and can be applied to the essential features hereinbefore set forth, and follows in the scope of the appended claims.

What is claimed is:

1. A peptide consisting of the amino acid sequence set forth in SEQ ID NO: 1, wherein said peptide binds to a human major histocompatibility complex class I A molecule.

\* \* \* \*

SEQUENCE LISTING

```
<160> NUMBER OF SEQ ID NOS: 73

<210> SEQ ID NO 1
<211> LENGTH: 9
<212> TYPE: PRT
<213> ORGANISM: Homo sapiens

<400> SEQUENCE: 1

Ile Leu Ala Lys Phe Leu His Trp Leu
1               5

<210> SEQ ID NO 2
<211> LENGTH: 9
<212> TYPE: PRT
<213> ORGANISM: Homo sapiens

<400> SEQUENCE: 2

Lys Leu Phe Gly Val Leu Arg Leu Lys
1               5

<210> SEQ ID NO 3
<211> LENGTH: 9
<212> TYPE: PRT
<213> ORGANISM: Homo sapiens

<400> SEQUENCE: 3

Glu Leu Leu Arg Ser Phe Phe Tyr Val
1               5

<210> SEQ ID NO 4
<211> LENGTH: 9
<212> TYPE: PRT
<213> ORGANISM: Homo sapiens
```

```
<400> SEQUENCE: 4

Arg Leu Val Asp Asp Phe Leu Leu Val
  1               5

<210> SEQ ID NO 5
<211> LENGTH: 9
<212> TYPE: PRT
<213> ORGANISM: Homo sapiens

<400> SEQUENCE: 5

Phe Leu Trp Gly Pro Arg Ala Leu Val
  1               5

<210> SEQ ID NO 6
<211> LENGTH: 9
<212> TYPE: PRT
<213> ORGANISM: Homo sapiens

<400> SEQUENCE: 6

His Phe Leu Leu Trp Lys Leu Ile Ala
  1               5

<210> SEQ ID NO 7
<211> LENGTH: 9
<212> TYPE: PRT
<213> ORGANISM: Homo sapiens

<400> SEQUENCE: 7

Ala His Thr Lys Asp Gly Phe Asn Phe
  1               5

<210> SEQ ID NO 8
<211> LENGTH: 10
<212> TYPE: PRT
<213> ORGANISM: Homo sapiens

<400> SEQUENCE: 8

Lys Leu Thr Arg His Arg Val Thr Tyr Val
  1               5                  10

<210> SEQ ID NO 9
<211> LENGTH: 10
<212> TYPE: PRT
<213> ORGANISM: Homo sapiens

<400> SEQUENCE: 9

Leu Leu Leu Asp Thr Arg Thr Leu Glu Val
  1               5                  10

<210> SEQ ID NO 10
<211> LENGTH: 10
<212> TYPE: PRT
<213> ORGANISM: Homo sapiens

<400> SEQUENCE: 10

Phe Leu His Trp Leu Met Ser Val Tyr Val
  1               5                  10

<210> SEQ ID NO 11
<211> LENGTH: 10
<212> TYPE: PRT
<213> ORGANISM: Homo sapiens

<400> SEQUENCE: 11
```

```
Phe Leu Leu Lys Leu Thr Arg His Arg Val
1               5                   10

<210> SEQ ID NO 12
<211> LENGTH: 10
<212> TYPE: PRT
<213> ORGANISM: Homo sapiens

<400> SEQUENCE: 12

Trp Leu Met Ser Val Tyr Val Val Glu Leu
1               5                   10

<210> SEQ ID NO 13
<211> LENGTH: 10
<212> TYPE: PRT
<213> ORGANISM: Homo sapiens

<400> SEQUENCE: 13

Gly Leu Phe Asp Val Phe Leu Arg Phe Met
1               5                   10

<210> SEQ ID NO 14
<211> LENGTH: 9
<212> TYPE: PRT
<213> ORGANISM: Homo sapiens

<400> SEQUENCE: 14

Leu Leu Ala Arg Cys Ala Leu Phe Val
1               5

<210> SEQ ID NO 15
<211> LENGTH: 9
<212> TYPE: PRT
<213> ORGANISM: Homo sapiens

<400> SEQUENCE: 15

Trp Leu Cys His Gln Ala Phe Leu Leu
1               5

<210> SEQ ID NO 16
<211> LENGTH: 10
<212> TYPE: PRT
<213> ORGANISM: Homo sapiens

<400> SEQUENCE: 16

Val Glu Leu Leu Arg Ser Phe Phe Tyr Val
1               5                   10

<210> SEQ ID NO 17
<211> LENGTH: 9
<212> TYPE: PRT
<213> ORGANISM: Homo sapiens

<400> SEQUENCE: 17

Phe Leu Trp Gly Pro Arg Ala Leu Val
1               5

<210> SEQ ID NO 18
<211> LENGTH: 9
<212> TYPE: PRT
<213> ORGANISM: Homo sapiens

<400> SEQUENCE: 18

Leu Leu Phe Gly Tyr Pro Val Tyr Val
```

```
<210> SEQ ID NO 19
<211> LENGTH: 9
<212> TYPE: PRT
<213> ORGANISM: Homo sapiens

<400> SEQUENCE: 19

Phe Leu Trp Gly Pro Arg Ala Leu Val
1               5

<210> SEQ ID NO 20
<211> LENGTH: 9
<212> TYPE: PRT
<213> ORGANISM: Homo sapiens

<400> SEQUENCE: 20

Gly Ile Leu Gly Phe Val Phe Thr Leu
1               5

<210> SEQ ID NO 21
<211> LENGTH: 9
<212> TYPE: PRT
<213> ORGANISM: Homo sapiens

<400> SEQUENCE: 21

Tyr Ala Glu Thr Lys His Phe Leu Tyr
1               5

<210> SEQ ID NO 22
<211> LENGTH: 10
<212> TYPE: PRT
<213> ORGANISM: Homo sapiens

<400> SEQUENCE: 22

Val Val Glu Leu Leu Arg Ser Phe Phe Tyr
1               5                   10

<210> SEQ ID NO 23
<211> LENGTH: 9
<212> TYPE: PRT
<213> ORGANISM: Homo sapiens

<400> SEQUENCE: 23

Ile Ser Asp Thr Ala Ser Leu Cys Tyr
1               5

<210> SEQ ID NO 24
<211> LENGTH: 9
<212> TYPE: PRT
<213> ORGANISM: Homo sapiens

<400> SEQUENCE: 24

Glu Val Asp Pro Ile Gly His Leu Tyr
1               5

<210> SEQ ID NO 25
<211> LENGTH: 9
<212> TYPE: PRT
<213> ORGANISM: Homo sapiens

<400> SEQUENCE: 25

Cys Thr Glu Leu Lys Leu Ser Asp Tyr
1               5
```

```
<210> SEQ ID NO 26
<211> LENGTH: 9
<212> TYPE: PRT
<213> ORGANISM: Homo sapiens

<400> SEQUENCE: 26

Gly Leu Phe Asp Val Phe Leu Arg Phe
 1               5

<210> SEQ ID NO 27
<211> LENGTH: 9
<212> TYPE: PRT
<213> ORGANISM: Homo sapiens

<400> SEQUENCE: 27

Arg Leu Arg Glu Glu Ile Leu Ala Lys
 1               5

<210> SEQ ID NO 28
<211> LENGTH: 9
<212> TYPE: PRT
<213> ORGANISM: Homo sapiens

<400> SEQUENCE: 28

Ile Leu Arg Gly Ser Val Ala His Lys
 1               5

<210> SEQ ID NO 29
<211> LENGTH: 9
<212> TYPE: PRT
<213> ORGANISM: Homo sapiens

<400> SEQUENCE: 29

Tyr Val Thr Glu Thr Thr Phe Gln Lys
 1               5

<210> SEQ ID NO 30
<211> LENGTH: 9
<212> TYPE: PRT
<213> ORGANISM: Homo sapiens

<400> SEQUENCE: 30

Gln Thr Val Cys Thr Asn Ile Tyr Lys
 1               5

<210> SEQ ID NO 31
<211> LENGTH: 9
<212> TYPE: PRT
<213> ORGANISM: Homo sapiens

<400> SEQUENCE: 31

Lys Thr Phe Leu Arg Thr Leu Val Arg
 1               5

<210> SEQ ID NO 32
<211> LENGTH: 9
<212> TYPE: PRT
<213> ORGANISM: Homo sapiens

<400> SEQUENCE: 32

Arg Leu Arg Glu Glu Ile Leu Ala Lys
 1               5

<210> SEQ ID NO 33
```

```
<211> LENGTH: 9
<212> TYPE: PRT
<213> ORGANISM: Homo sapiens

<400> SEQUENCE: 33

Gly Val Gly Gly Pro Gly Gly His Lys
1               5

<210> SEQ ID NO 34
<211> LENGTH: 9
<212> TYPE: PRT
<213> ORGANISM: Homo sapiens

<400> SEQUENCE: 34

Ile Val Thr Asp Phe Ser Val Ile Lys
1               5

<210> SEQ ID NO 35
<211> LENGTH: 9
<212> TYPE: PRT
<213> ORGANISM: Homo sapiens

<400> SEQUENCE: 35

Thr Tyr Val Pro Leu Leu Gly Ser Leu
1               5

<210> SEQ ID NO 36
<211> LENGTH: 9
<212> TYPE: PRT
<213> ORGANISM: Homo sapiens

<400> SEQUENCE: 36

Cys Tyr Gly Asp Met Glu Asn Lys Leu
1               5

<210> SEQ ID NO 37
<211> LENGTH: 10
<212> TYPE: PRT
<213> ORGANISM: Homo sapiens

<400> SEQUENCE: 37

Phe Tyr Arg Lys Ser Val Trp Ser Lys Leu
1               5                   10

<210> SEQ ID NO 38
<211> LENGTH: 9
<212> TYPE: PRT
<213> ORGANISM: Homo sapiens

<400> SEQUENCE: 38

Ala Tyr Gln Val Cys Gly Pro Pro Leu
1               5

<210> SEQ ID NO 39
<211> LENGTH: 9
<212> TYPE: PRT
<213> ORGANISM: Homo sapiens

<400> SEQUENCE: 39

Arg Tyr Leu Lys Asp Gln Gln Leu Leu
1               5

<210> SEQ ID NO 40
<211> LENGTH: 9
<212> TYPE: PRT
```

-continued

<213> ORGANISM: Homo sapiens

<400> SEQUENCE: 40

Ala Tyr Gly Leu Asp Phe Tyr Ile Leu
1               5

<210> SEQ ID NO 41
<211> LENGTH: 9
<212> TYPE: PRT
<213> ORGANISM: Homo sapiens

<400> SEQUENCE: 41

Arg Leu Phe Phe Tyr Arg Lys Ser Val
1               5

<210> SEQ ID NO 42
<211> LENGTH: 9
<212> TYPE: PRT
<213> ORGANISM: Homo sapiens

<400> SEQUENCE: 42

Leu Gln Leu Pro Pro His Gln Gln Val
1               5

<210> SEQ ID NO 43
<211> LENGTH: 9
<212> TYPE: PRT
<213> ORGANISM: Homo sapiens

<400> SEQUENCE: 43

Arg Leu Gly Pro Gln Gly Trp Arg Leu
1               5

<210> SEQ ID NO 44
<211> LENGTH: 9
<212> TYPE: PRT
<213> ORGANISM: Homo sapiens

<400> SEQUENCE: 44

Ser Leu Gln Glu Leu Thr Trp Lys Met
1               5

<210> SEQ ID NO 45
<211> LENGTH: 9
<212> TYPE: PRT
<213> ORGANISM: Homo sapiens

<400> SEQUENCE: 45

Asn Val Leu Ala Phe Gly Phe Ala Leu
1               5

<210> SEQ ID NO 46
<211> LENGTH: 9
<212> TYPE: PRT
<213> ORGANISM: Homo sapiens

<400> SEQUENCE: 46

Val Leu Leu Lys Thr His Cys Pro Leu
1               5

<210> SEQ ID NO 47
<211> LENGTH: 9
<212> TYPE: PRT
<213> ORGANISM: Homo sapiens

```
<400> SEQUENCE: 47

Phe Leu Leu Val Thr Pro His Leu Thr
 1               5

<210> SEQ ID NO 48
<211> LENGTH: 9
<212> TYPE: PRT
<213> ORGANISM: Homo sapiens

<400> SEQUENCE: 48

Thr Leu Thr Asp Leu Gln Pro Tyr Met
 1               5

<210> SEQ ID NO 49
<211> LENGTH: 9
<212> TYPE: PRT
<213> ORGANISM: Homo sapiens

<400> SEQUENCE: 49

Ile Leu Ser Thr Leu Leu Cys Ser Leu
 1               5

<210> SEQ ID NO 50
<211> LENGTH: 9
<212> TYPE: PRT
<213> ORGANISM: Homo sapiens

<400> SEQUENCE: 50

Leu Met Ser Val Tyr Val Val Glu Leu
 1               5

<210> SEQ ID NO 51
<211> LENGTH: 9
<212> TYPE: PRT
<213> ORGANISM: Homo sapiens

<400> SEQUENCE: 51

Phe Leu Asp Leu Gln Val Asn Ser Leu
 1               5

<210> SEQ ID NO 52
<211> LENGTH: 9
<212> TYPE: PRT
<213> ORGANISM: Homo sapiens

<400> SEQUENCE: 52

Leu Leu Gly Ala Ser Val Leu Gly Leu
 1               5

<210> SEQ ID NO 53
<211> LENGTH: 9
<212> TYPE: PRT
<213> ORGANISM: Homo sapiens

<400> SEQUENCE: 53

Cys Leu Lys Glu Leu Val Ala Arg Val
 1               5

<210> SEQ ID NO 54
<211> LENGTH: 9
<212> TYPE: PRT
<213> ORGANISM: Homo sapiens

<400> SEQUENCE: 54
```

```
Leu Leu Asp Thr Arg Thr Leu Glu Val
1               5
```

<210> SEQ ID NO 55
<211> LENGTH: 9
<212> TYPE: PRT
<213> ORGANISM: Homo sapiens

<400> SEQUENCE: 55

```
Gly Leu Leu Leu Asp Thr Arg Thr Leu
1               5
```

<210> SEQ ID NO 56
<211> LENGTH: 9
<212> TYPE: PRT
<213> ORGANISM: Homo sapiens

<400> SEQUENCE: 56

```
Phe Leu Arg Thr Leu Val Arg Gly Val
1               5
```

<210> SEQ ID NO 57
<211> LENGTH: 9
<212> TYPE: PRT
<213> ORGANISM: Homo sapiens

<400> SEQUENCE: 57

```
Tyr Met Arg Gln Phe Val Ala His Leu
1               5
```

<210> SEQ ID NO 58
<211> LENGTH: 9
<212> TYPE: PRT
<213> ORGANISM: Homo sapiens

<400> SEQUENCE: 58

```
Arg Leu Thr Glu Val Ile Ala Ser Ile
1               5
```

<210> SEQ ID NO 59
<211> LENGTH: 10
<212> TYPE: PRT
<213> ORGANISM: Homo sapiens

<400> SEQUENCE: 59

```
Gln Val Trp Lys Asn Pro Thr Phe Phe Leu
1               5                   10
```

<210> SEQ ID NO 60
<211> LENGTH: 10
<212> TYPE: PRT
<213> ORGANISM: Homo sapiens

<400> SEQUENCE: 60

```
Val Leu Gln Leu Pro Phe His Gln Gln Val
1               5                   10
```

<210> SEQ ID NO 61
<211> LENGTH: 10
<212> TYPE: PRT
<213> ORGANISM: Homo sapiens

<400> SEQUENCE: 61

```
Phe Leu Leu Ser Ser Leu Arg Pro Ser Leu
1               5                   10
```

```
<210> SEQ ID NO 62
<211> LENGTH: 10
<212> TYPE: PRT
<213> ORGANISM: Homo sapiens

<400> SEQUENCE: 62

Leu Leu Leu Arg Leu Val Asp Asp Phe Leu
 1               5                  10

<210> SEQ ID NO 63
<211> LENGTH: 10
<212> TYPE: PRT
<213> ORGANISM: Homo sapiens

<400> SEQUENCE: 63

Lys Met Ser Val Arg Gly Cys Ala Trp Leu
 1               5                  10

<210> SEQ ID NO 64
<211> LENGTH: 10
<212> TYPE: PRT
<213> ORGANISM: Homo sapiens

<400> SEQUENCE: 64

Arg Leu Cys Glu Arg Gly Ala Lys Asn Val
 1               5                  10

<210> SEQ ID NO 65
<211> LENGTH: 10
<212> TYPE: PRT
<213> ORGANISM: Homo sapiens

<400> SEQUENCE: 65

Leu Leu Leu Arg Arg Val Gly Asp Asp Val
 1               5                  10

<210> SEQ ID NO 66
<211> LENGTH: 10
<212> TYPE: PRT
<213> ORGANISM: Homo sapiens

<400> SEQUENCE: 66

Gly Leu Leu Gly Ala Ser Val Leu Gly Leu
 1               5                  10

<210> SEQ ID NO 67
<211> LENGTH: 10
<212> TYPE: PRT
<213> ORGANISM: Homo sapiens

<400> SEQUENCE: 67

Leu Leu Leu Gln Ala Tyr Arg Phe His Ala
 1               5                  10

<210> SEQ ID NO 68
<211> LENGTH: 10
<212> TYPE: PRT
<213> ORGANISM: Homo sapiens

<400> SEQUENCE: 68

Lys Leu Pro Gly Thr Thr Leu Thr Ala Leu
 1               5                  10
```

```
<210> SEQ ID NO 69
<211> LENGTH: 10
<212> TYPE: PRT
<213> ORGANISM: Homo sapiens

<400> SEQUENCE: 69

Val Gln Trp Leu Cys His Gln Ala Phe Leu
1               5                   10

<210> SEQ ID NO 70
<211> LENGTH: 10
<212> TYPE: PRT
<213> ORGANISM: Homo sapiens

<400> SEQUENCE: 70

Ala Leu Val Ala Gln Cys Leu Val Cys Val
1               5                   10

<210> SEQ ID NO 71
<211> LENGTH: 10
<212> TYPE: PRT
<213> ORGANISM: Homo sapiens

<400> SEQUENCE: 71

Arg Leu Val Asp Asp Phe Leu Leu Val Thr
1               5                   10

<210> SEQ ID NO 72
<211> LENGTH: 10
<212> TYPE: PRT
<213> ORGANISM: Homo sapiens

<400> SEQUENCE: 72

Ser Ile Leu Ser Thr Leu Leu Cys Ser Leu
1               5                   10

<210> SEQ ID NO 73
<211> LENGTH: 10
<212> TYPE: PRT
<213> ORGANISM: Influenza A virus

<400> SEQUENCE: 73

Phe Leu Pro Ser Asp Cys Phe Pro Ser Val
1               5                   10
```